(12) United States Patent
Moshiri et al.

(10) Patent No.: US 7,297,541 B2
(45) Date of Patent: Nov. 20, 2007

(54) GENES ENCODING 4-HYDROXYPHENYLPYRUVATE DIOXYGENASE (HPPD) ENZYMES FOR PLANT METABOLIC ENGINEERING

(75) Inventors: Farhad Moshiri, Chesterfield, MO (US); Ming Hao, Wildwood, MO (US); Balasulojini Karunanandaa, Creve Coeur, MO (US); Henry E. Valentin, Wildwood, MO (US); Tyamagondlu V. Venkatesh, St. Louis, MO (US); Yun-Hua Huang Wong, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 26 days.

(21) Appl. No.: 11/043,542

(22) Filed: Jan. 26, 2005

(65) Prior Publication Data
US 2005/0289664 A1    Dec. 29, 2005

Related U.S. Application Data

(60) Provisional application No. 60/539,309, filed on Jan. 26, 2004.

(51) Int. Cl.
C07H 21/04 (2006.01)
C12N 9/02 (2006.01)
C12N 5/04 (2006.01)
C12N 15/82 (2006.01)

(52) U.S. Cl. ............ 435/419; 535/189; 535/410; 535/320.1; 535/468; 536/23.2

(58) Field of Classification Search .......... None
See application file for complete search history.

(56) References Cited

U.S. PATENT DOCUMENTS

| | | | |
|---|---|---|---|
| 5,759,538 A | 6/1998 | Donovan et al. | 424/93.461 |
| 5,786,513 A | 7/1998 | Schulz | 424/725 |
| 5,962,264 A | 10/1999 | Donovan et al. | 435/69.1 |
| 6,245,968 B1 | 6/2001 | Boudec et al. | 800/278 |
| 6,384,301 B1 | 5/2002 | Martinell et al. | 800/294 |
| 6,555,714 B1 | 4/2003 | Schulz | 568/333 |
| 6,768,044 B1 * | 7/2004 | Boudec et al. | 800/300 |
| 6,822,142 B2 | 11/2004 | Karunanandaa et al. | 800/298 |
| 6,825,398 B2 | 11/2004 | Wang et al. | 800/287 |
| 7,112,717 B2 | 9/2006 | Valentin et al. | 800/278 |
| 2003/0125725 A1 | 7/2003 | Millis et al. | 549/411 |
| 2003/0148300 A1 | 8/2003 | Valentin et al. | 435/6 |
| 2003/0150015 A1 | 8/2003 | Norris et al. | 800/278 |
| 2003/0154513 A1 | 8/2003 | Eenennaam et al. | 800/281 |
| 2003/0176675 A1 | 9/2003 | Valentin et al. | 536/23.1 |
| 2004/0045051 A1 | 3/2004 | Norris et al. | 800/278 |

FOREIGN PATENT DOCUMENTS

| | | |
|---|---|---|
| EP | 293356 | 11/1988 |
| WO | WO97/27285 | 7/1997 |
| WO | WO97/49816 | 12/1997 |

OTHER PUBLICATIONS

Dahnhart et al. "The hydroxyphenylpyruvate dioxygenase from synechocytis sp. pcc6803 is not required for plastoquinon biosynthesis," *FEBS Lett.*, 523:177-181, 2002.

Denoya et al., "A *Streptomyces avermitilis* gene encoding a 4-hydroxyphenylpyruvic acid dioxygenase-like protein that directs the production of homogentisic acid and an ochronotic pigment in *Escherichia coli*," *J. Bacteriol.*, 176:5312-5319, 1994.

Emanuelson et al., "ChloroP, a neural network-based method for predicting chloroplast transit peptides and their cleavage sites," *Protein Sci.*, 8:978-984, 1999.

Fiedler et al., "The formation of homogentisate in the biosynthesis of tocopherol and plastoquinone in spinach chloroplasts," *Planta*, 155:511-515, 1982.

Garcia et al., "Characterization and subcellular compartmentation of recombinant 4-hydroxyphenylpyruvate dioxygenase from arabidopsis in transgenic tobacco," *Plant Phys.* 119:1507-1516, 1999.

Garcia et al., "Subcellular localization and purification of a p-hydroxyphenylpyruvate dioxygenase from culture carrot cells and characterization of the corresponding cDNA," *Biochem. J.*, 325:761-769, 1997.

GenBank Accession No. AAB70025.1 GI:2392518.
GenBank Accession No. BAA10536.1 GI:1001726.

Marshall et al., "Biosynthesis of tocopherols: A re-examination of the biosynthesis and metabolism of 2-methyl-6-phytyl-1,4-benzoquinol," *Phytochem.*, 24:1705-1711, 1985.

Norris et al., "Genetic dissection of carotenoid synthesis in arabidopsis defines plastoquinone as an essential component of phytoene desaturation," *The Plant Cell*, 7:2139-2149, 1995.

Padgette et al., "Site-directed mutagenesis of a conserved region of the 5-enolpyruvylshikimate-3-phosphate synthase active site," *J. Biol. Chem.*, 266:22364-22369, 1991.

Ryle and Hausinger, "Non-heme iron oxygenases," *Curr. Opin. Chem. Biol.*, 6:193-201, 2002.

Soll et al., "Tocopherol and plastoquinone synthesis in spinach chloroplasts subfractions," *Arch. Biochem. Biophys.*, 204:544-550, 1980.

U.S. Appl. No. 11/049,404, filed Feb. 2, 2002, Corbin.

* cited by examiner

*Primary Examiner*—Rebecca Prouty
*Assistant Examiner*—M. Y. Meah
(74) *Attorney, Agent, or Firm*—Fulbright & Jaworski L.L.P.

(57) ABSTRACT

The present invention is in the field of plant genetics and biochemistry. More specifically, the present invention relates to genes and polypeptides associated with the tocopherol biosynthesis pathway, namely those encoding 4-Hydroxyphenylpyruvate Dioxygenase activity, and uses thereof.

18 Claims, 13 Drawing Sheets

SEQ ID NO: 28 represents a Bt Bt-HX-1-f PCR primer sequence.
5'- GCGCAG CCATG GCG AAA CAA AAA TCT ATG GAT ACG -3'

SEQ ID NO: 29 SEQ ID NO: 29 represents a Bt Bt-HX-2-f PCR primer sequence.
5'- GCGCAG CCATG GAG GAC TTT TTC CAG TAC -3'

SEQ ID NO: 30 SEQ ID NO: 30 represents a Bt Bt-HX-3-r PCR primer sequence.
5'- GCGCAG CTCGAG TCA TAA GTT TCC GCG ACG CTC -3'

SEQ ID NO: 31 represents a cotton Gh-1-f PCR primer sequence.
5'- GCGCAG CC ATG GCC AAT CCG AAA TCC GAT CGG TTC AC -3'

SEQ ID NO: 32 represents a cotton Gh-2-r PCR primer sequence.
5'- GCGCAG CTCGAG TCA TGG ATT CTG GGA CTG TTT GG -3'

SEQ ID NO: 33 represents a *Brassica* Bn-1-f PCR primer sequence.
5'- GGAGCT CCATG GGG CAC GAA AAC GCC GC -3'

SEQ ID NO: 34 represents a *Brassica* Bn-2-r PCR primer sequence.
5'- GGAGCT CTCGAG TCA ACC CAC AAG CTG TTT GGC -3'

SEQ ID NO: 35 represents a tomato PCR primer sequence.
5'- GGAGCTCATATGGCTAATCCCCGTTCCGATTTC -3'

SEQ ID NO: 36 represents a tomato PCR primer sequence.
5'- GGAGCTCTCGAGTCATTCGACAGCAGCTACTTG -3'

Figure 2

GENES ENCODING 4-HYDROXYPHENYLPYRUVATE DIOXYGENASE (HPPD) ENZYMES FOR PLANT METABOLIC ENGINEERING

This application claims priority to U.S. Provisional Application No. 60/539,309 filed Jan. 26, 2004, the disclosure of which is incorporated herein by reference in its entirety.

The present invention is in the field of plant genetics and biochemistry. More specifically, the present invention relates to genes and polypeptides associated with the tocopherol biosynthesis pathway, namely those encoding 4-Hydroxyphenylpyruvate Dioxygenase (HPPD) activity, and uses thereof.

Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.*, 16:321–347, 1996). Tocopherol functions, in part, by stabilizing the lipid bilayer of biological membranes (Skrypin and Kagan, *Biochim. Biophys. Acta.*, 815: 209, 1995; Kagan, *N.Y. Acad. Sci.*, p. 121, 1989; Gomez-Fernandez et al., *Ann. N.Y. Acad. Sci.*, p. 109, 1989), reducing polyunsaturated fatty acid (PUFA) free radicals generated by lipid oxidation (Fukuzawa et al., *Lipids*, 17:511–513, 1982), and scavenging oxygen free radicals, lipid peroxy radicals and singlet oxygen species (Diplock et al., *Ann. N.Y. Acad. Sci.*, 570:72, 1989; Fryer, *Plant Cell Environ.*, 15(4):381–392, 1992).

The compound α-tocopherol, which is often referred to as vitamin E, belongs to a class of lipid-soluble antioxidants that includes α, β, γ, and δ-tocopherols and α, β, γ, and δ-tocotrienols. α, β, γ, and δ-tocopherols and α, β, γ, and δ-tocotrienols are sometimes referred to collectively as "vitamin E". Vitamin E is more appropriately defined chemically as the beneficial activity for animals and humans which can be e.g., determined in the rat fetal absorption and hemolysis assays (Chow, *Vitamin E*, In: Handbook of Vitamins ISBN:0–8247–0428–2). α-Tocopherol has the highest vitamin E activity, in part because it is readily absorbed and retained by the body (Traber and Sies, *Annu. Rev. Nutr.*, 16:321–347, 1996). However, other tocopherols and tocotrienols such as β, γ, δ-tocopherols and α, β, γ, δ-tocotrienols also have significant health and nutritional benefits.

Only plants and certain other photosynthetic organisms, including cyanobacteria, synthesize tocopherols. As a result, mammalian dietary tocopherols are obtained almost exclusively from these sources. Plant tissues vary considerably in total tocopherol content and tocopherol composition but α-tocopherol is the predominant tocopherol species found in green, photosynthetic plant tissues. Leaf tissue can contain from 10–50 μg of total tocopherols per gram fresh weight, but the edible parts of most of the world's major staple crops (e.g., rice, corn, wheat, potato) produce low to extremely low levels of total tocopherols, of which only a small percentage is α-tocopherol (Hess, Vitamin E, α-tocopherol, In: Antioxidants in Higher Plants, R. Alscher and J. Hess, Eds., CRC Press, Boca Raton, Fla., pp. 111–134, 1993). Oil seed crops generally contain much higher levels of total tocopherols, but α-tocopherol is present only as a minor component in most oilseeds (Taylor and Barnes, *Chemy Ind.*, 722–726, 1981).

The recommended daily dietary intake of 15–30 IU of vitamin E is quite difficult to achieve from the average American diet. For example, it would take over 750 grams of spinach leaves, in which α-tocopherol comprises 60% of total tocopherols, or 200–400 grams of soybean oil to satisfy this recommended daily vitamin E intake. While it is possible to augment the diet with supplements, most of these supplements contain primarily synthetic vitamin E, having eight stereoisomers, whereas natural vitamin E is predominantly composed of only a single, more active, isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocopherols, increased tocopherol levels in crops have been associated with enhanced stability and extended shelf life of plant products (Peterson, *Cereal-Chem.*, 72(1):21–24, 1995; Ball, *Fat-soluble vitamin assays in food analysis. A comprehensive review*, London, Elsevier Science Publishers Ltd., 1988). Further, tocopherol supplementation of swine, beef, and poultry feeds has been shown to significantly increase meat quality and extend the shelf life of post-processed meat products by retarding post-processing lipid oxidation, which contributes to undesirable flavor components (Sante and Lacourt, *J. Sci. Food Agric.*, 65(4):503–507, 1994; Buckley et al., *J. of Animal Science*, 73:3122–3130, 1995).

The tocopherol biosynthetic pathway in higher plants involves several enzymes including HPPD (FIG. 1) (Fiedler et al., *Planta*, 155:511–515, 1982; Soll et al., *Arch. Biochem. Biophys.*, 204:544–550, 1980; Marshall et al., *Phytochem.*, 24:1705–1711, 1985). HPPD, also known as 4-HPPD, is a mononuclear, non-heme, iron-containing enzyme which is a member of the family of 2-oxoacid dependent dioxygenases (Ryle et al., *Curr. Opin. Chem. Biol.*, 6:193–201, 2002). HPPD catalyzes the conversion of 4-hydroxyphenylpyruvate to homogentisic acid and is a key enzyme involved in the synthesis of tocopherol and plastoquinone.

In plant tissues, HPPD is an enzyme central to the biosynthesis of the essential quinoid-compounds derived from the amino acid tyrosine, such as plastoquinones or tocopherols. Because plastoquinones and tocopherols are essential molecules for plants, inhibitors of HPPD are useful as herbicides (U.S. Pat. Nos. 5,786,513 and 6,555,714; PCT Publication WO 97/49816). HPPDs can also be used to make plants tolerant to certain herbicides by mutating the target enzyme into a functional enzyme that is less sensitive to the herbicide, or to its active metabolite, such as, for example, the enzymes for tolerance to glyphosate (EP 293356; S. R. Padgette et al., *J. Biol. Chem.*, 266:22364–22369, 1991). Another means of producing herbicide tolerant plants is by over-expression of an herbicide sensitive HPPD or polypeptide having HPPD activity in a transformed plant so as to produce quantities of the target HPPD enzyme in the plant which are sufficient, given the kinetic constants of HPPD, so as to have enough of the functional HPPD enzyme available despite the presence of its inhibitor (U.S. Pat. No. 6,245,968).

SUMMARY OF THE INVENTION

There is a need in the art for polynucleotide molecules encoding enzymes involved in tocopherol biosynthesis, as well as related enzymes for the enhancement or alteration of tocopherol production in plants. There is a further need for transgenic organisms expressing those polynucleotide molecules involved in tocopherol biosynthesis which are capable of nutritionally enhancing food and feed sources.

The present invention includes and provides a substantially purified polynucleotide molecule comprising:
(a) a polynucleotide molecule comprising a nucleotide sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, nucleotide sequences having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23;
(b) a polynucleotide molecule encoding a 4-hydroxyphenylpyruvate dioxygenase ("HPPD") polypeptide or polypeptide having HPPD activity comprising a sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23;
(c) a polynucleotide molecule comprising a polynucleotide sequence encoding a polypeptide comprising a sequence selected from the group consisting of: SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24; or
(d) a polynucleotide molecule comprising a polynucleotide sequence encoding a 4-hydroxyphenylpyruvate dioxygenase ("HPPD") polypeptide or polypeptide having HPPD activity comprising a sequence selected from the group consisting of: SEQ ID NO: 4, polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24.

In one embodiment, the substantially purified polynucleotide molecule of the present invention is operably linked to a heterologous promoter that functions in plants, including seed-preferred promoters, and including the napin, 7S alpha, 7S alpha' 7S beta, USP 88, enhanced USP 88, Arcelin 5, and oleosin promoters.

In one embodiment, a substantially purified polynucleotide molecule of the present invention is operably linked to a polynucleotide encoding a chloroplast transit peptide. In one embodiment, a plasmid comprises a substantially purified polynucleotide molecule of the present invention.

In one embodiment, a chimeric gene comprises a substantially purified polynucleotide molecule of the present invention operably linked to at least one regulatory sequence not associated in nature with the substantially purified polynucleotide molecule. In one embodiment, the present invention comprises a microbial host transformed with the chimeric gene. In one embodiment, the present invention comprises a plant host cell transformed with the chimeric gene.

The present invention includes and provides a substantially purified polypeptide comprising:
(a) SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24; or
(b) a 4-hydroxyphenylpyruvate dioxygenase ("HPPD") polypeptide or polypeptide having HPPD activity wherein the polypeptide comprises a sequence selected from the group consisting of: SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24.

The present invention includes and provides a method of producing a transformed plant cell, plant tissue, plant organ, or plant comprising at least one of an increased tocopherol level and increased tocotrienol level relative to a wild type plant cell, plant tissue, plant organ, or plant comprising:

(1) transforming a plant cell, plant tissue, plant organ, or plant with an introduced polynucleotide molecule comprising a polynucleotide sequence encoding a 4-hydroxyphenylpyruvate dioxygenase ("HPPD") polypeptide or polypeptide having HPPD activity comprising:

(a) a polynucleotide molecule comprising a polynucleotide sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 7, a nucleotide sequence having at least 80% identity to SEQ ID NO: 7, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23;

(b) a polynucleotide molecule comprising a polynucleotide sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 7, a nucleotide sequence having at least 80% identity to SEQ ID NO: 7, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23, wherein the substantially purified polynucleotide molecule is operably linked to a polynucleotide encoding a chloroplast transit peptide;

(c) a polynucleotide molecule comprising a polynucleotide sequence encoding a HPPD polypeptide or polypeptide having HPPD activity comprising a sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 7, a nucleotide sequence having at least 80% identity to SEQ ID NO: 7, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23;

(d) a polynucleotide molecule comprising a polynucleotide sequence encoding an HPPD polypeptide or polypeptide having HPPD activity comprising a sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 7, a nucleotide sequence having at least 80% identity to SEQ ID NO: 7, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23; wherein the substantially purified polynucleotide molecule is operably linked to a polynucleotide encoding a chloroplast transit peptide;

(e) a polynucleotide molecule comprising a polynucleotide sequence encoding a polypeptide sequence selected from the group consisting of: SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 8, a polypeptide sequence having at least 58% identity to SEQ ID NO: 8, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24; or (f) polynucleotide molecules comprising a polynucleotide sequence encoding a polypeptide sequence selected from the group consisting of: SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 8, a polypeptide sequence having at least 58% identity to SEQ ID NO: 8, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24, wherein the substantially purified polynucleotide molecule is operably linked to a polynucleotide encoding a chloroplast transit peptide;

(2) regenerating a plant from the cell, tissue, organ, or plant; and (3) growing the plant.

In one embodiment, at least one additional polynucleotide molecule encoding an enzyme selected from the group consisting of MT1, tMT2, GMT, tyrA, HPT, tocopherol cyclase, chlorophyllase, dxs, dxr, GGPPS, AANT1, LTT1, IDI, and GGH is introduced into the plant. In one embodiment the at least one additional polynucleotide molecule is selected from the group consisting of SEQ ID NOs: 25, 26, and 27.

In one embodiment, the method produces a transformed plant selected from the group consisting of alfalfa, *Arabidopsis thaliana*, barley, *Brassica campestris*, oilseed rape, broccoli, cabbage, citrus, canola, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, chick peas, corn, *Phaseolus*, crambe, mustard, castor bean, sesame, cottonseed, linseed, safflower, and oil palm. In one embodiment, the transformed plant is selected from the group consisting of canola, oilseed rape, and soybean.

The present invention includes and provides a method for producing a transformed plant which comprises tissue with at least one of increased α-tocopherol, α-tocotrienol, β-tocopherol, β-tocotrienol, γ-tocopherol, γ-tocotrienol, δ-tocopherol, and δ-tocotrienol levels relative to a plant with a similar genetic background but lacking said introduced polynucleotide molecule. In one method of the present invention, the introduced polynucleotide molecule is operably linked to a promoter, including a seed preferred promoter, including the napin, 7S alpha, 7S alpha', USP 88, enhanced USP 88, Arcelin 5, and Oleosin promoters.

In one method of the present invention, the tissue comprises a seed.

The present invention includes and provides a method for increasing the ability of a plant to withstand a stress, the method comprising incorporating into one or more cells of the plant a DNA construct comprising:

(a) an heterologous promoter;

(b) a DNA encoding an HPPD; and (c) a 3' untranslated region containing a functional polyadenylation signal wherein expression of the DNA construct increases the ability of the plant to withstand the stress.

In one embodiment, the DNA encoding an HPPD is selected from the group consisting of SEQ ID NOs: 3, 5, 7, 9, 11, 13, 15, 17, 19, 21, and 23. The present invention includes and provides a plant cell transformed with a DNA construct encoding an HPPD that confers stress tolerance to a plant regenerated from said plant cell as well as a transgenic plant regenerated from such plant cell.

Also encompassed within the present invention are the transformed plants produced by the methods of the present invention, seed from the transformed plants, oil from the seeds of the transformed plants, and meal from the seed of the transformed plants.

The present invention includes and provides an antibody capable of binding a polypeptide comprising a polypeptide sequence selected from the group consisting of SEQ ID NOs: 4, 6, 8, 10, 12, 16, 18, 20, 22, and 24.

The present invention includes and provides a method for screening for agents that alter tocopherol levels in a plant comprising: (a) providing a plant lacking a polypeptide comprising a polypeptide sequence selected from the group consisting of SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 8, a polypeptide sequence having at least 58% identity to SEQ ID NO: 8, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24; (b) exposing the plant to a test agent; and (c) assaying tocopherol levels in the plant. The agents include, e.g., polynucleotide primers, polynucleotide fragments, and antibodies.

The present invention includes isolated nucleic acid primer sequences comprising one or more of SEQ ID NOs: 28–36, or the complement thereof.

The present invention includes a method to detect or identify, in the genome of a transformed plant or progeny thereof, a heterologous polynucleotide molecule encoding a plant HPPD polypeptide, or a plant polypeptide having HPPD activity of the present invention, comprising a polynucleotide molecule selected from the group consisting of SEQ ID NOs: 28–36, wherein said polynucleotide molecule is used as a DNA primer in a DNA amplification method.

BRIEF DESCRIPTION OF THE FIGURES

FIG. 2 illustrates polynucleotide primer sequences.

DESCRIPTION OF THE NUCLEIC ACID AND POLYPEPTIDE SEQUENCES

Figure 1:
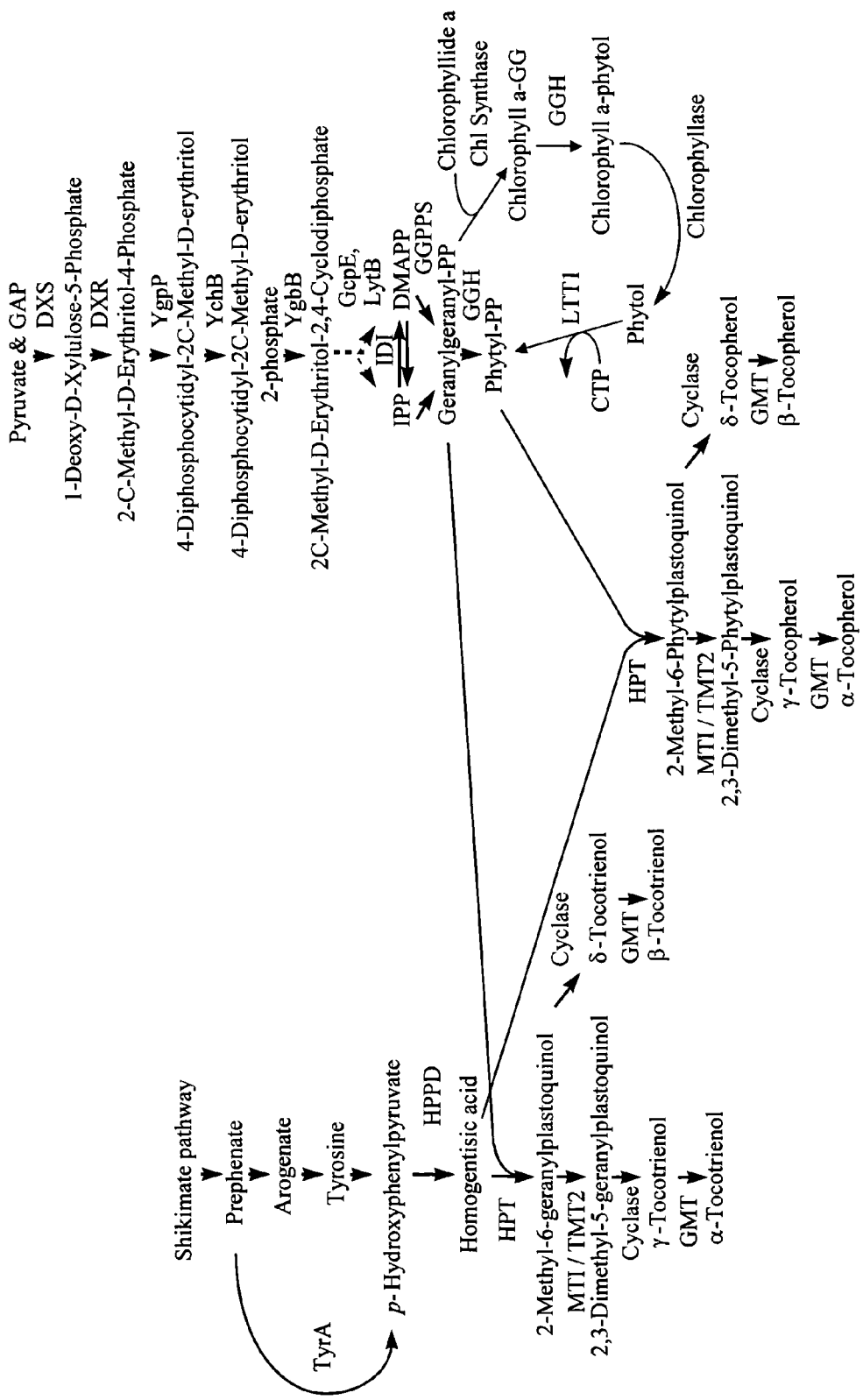
FIG. 1 illustrates a schematic representation of the tocopherol biosynthesis pathway.

SEQ ID NO: 1 represents a polynucleotide sequence encoding a *Synechocystis* sp. PCC6803 HPPD.

SEQ ID NO: 2 represents a polynucleotide sequence encoding an *Arabidopsis thaliana* HPPD.

SEQ ID NO: 3 represents a polynucleotide sequence encoding a *Bacillus thuringiensis* HPPD.

SEQ ID NO: 4 represents a *Bacillus thuringiensis* HPPD polypeptide.

SEQ ID NO: 5 represents a polynucleotide sequence encoding a *Bacillus thuringiensis*.

SEQ ID NO: 6 represents a *Bacillus thuringiensis* HPPD polypeptide.

SEQ ID NO: 7 represents a polynucleotide sequence encoding a *Bacillus thuringiensis* HPPD.

SEQ ID NO: 8 represents a *Bacillus thuringiensis* HPPD polypeptide.

SEQ ID NO: 9 represents a polynucleotide sequence encoding a *Bacillus thuringiensis* HPPD.

SEQ ID NO: 10 represents a *Bacillus thuringiensis* HPPD polypeptide.

SEQ ID NO: 11 represents a polynucleotide sequence encoding a *Bacillus thuringiensis* HPPD.

SEQ ID NO: 12 represents a *Bacillus thuringiensis* HPPD polypeptide.

SEQ ID NO: 13 represents a polynucleotide sequence encoding a modified *Bacillus thuringiensis* HPPD.

SEQ ID NO: 14 represents a modified *Bacillus thuringiensis* HPPD polypeptide.

SEQ ID NO: 15 represents a polynucleotide sequence encoding a *Gossypium hirsutum* HPPD.

SEQ ID NO: 16 represents a *Gossypium hirsutum* HPPD polypeptide.

SEQ ID NO: 17 represents a polynucleotide sequence encoding a *Gossypium hirsutum* HPPD.

SEQ ID NO: 18 represents a *Gossypium hirsutum* HPPD polypeptide.

SEQ ID NO: 19 represents a polynucleotide molecule sequence encoding a *Brassica napus* HPPD.

SEQ ID NO: 20 represents a *Brassica napus* HPPD polypeptide.

SEQ ID NO: 21 represents a polynucleotide sequence encoding a *Lycopersicon esculentum* HPPD.

SEQ ID NO: 22 represents a *Lycopersicon esculentum* HPPD polypeptide.

SEQ ID NO: 23 represents a polynucleotide sequence encoding a *Sphingomonas elodea* HPPD.

SEQ ID NO: 24 represents a *Sphingomonas elodea* HPPD polypeptide.

SEQ ID NO: 25 represents a polynucleotide sequence of an *Erwinia herbicola* tyrA.

SEQ ID NO: 26 represents a polynucleotide sequence of an *Arabidopsis thaliana* HPT.

SEQ ID NO: 27 represents a polynucleotide sequence of an *Arabidopsis thaliana* GGH.

SEQ ID NO: 28 represents a Bt forward (f) Bt-HX-1-f PCR primer sequence.

SEQ ID NO: 29 represents a Bt forward (f) Bt-HX-2-f PCR primer sequence.

SEQ ID NO: 30 represents a Bt reverse (r) Bt-HX-3-r PCR primer sequence.

SEQ ID NO: 31 represents a cotton forward (f) Gh-1-f PCR primer sequence.

SEQ ID NO: 32 represents a cotton reverse (r) Gh-1-r PCR primer sequence.

SEQ ID NO: 33 represents a *Brassica* forward (f) Bn-1-f PCR primer sequence.

SEQ ID NO: 34 represents a *Brassica* reverse (r) Bn-2-r PCR primer sequence.

SEQ ID NO: 35 represents a tomato forward (f) PCR primer sequence.

SEQ ID NO: 36 represents a tomato reverse (r) PCR primer sequence.

SEQ ID NO: 37 represents an *Arabidopsis thaliana* HPPD polypeptide.

SEQ ID NO: 38 represents an *Arabidopsis thaliana* HPPD polypeptide antigen.

SEQ ID NO: 39 represents an *Arabidopsis thaliana* HPPD polypeptide antigen.

SEQ ID NO: 40 represents a *Synechocystis* sp. HPPD polypeptide.

SEQ ID NO: 41 represents a *Synechocystis* sp. HPPD polypeptide antigen.

SEQ ID NO: 42 represents a *Bacillus thuringiensis* HPPD polypeptide antigen.

SEQ ID NO: 43 represents a Uni-HPPD polypeptide antigen.

SEQ ID NO: 44 represents a *Bacillus thuringiensis* HPPD polynucleotide sequence.

DETAILED DESCRIPTION OF THE INVENTION

The present invention provides a number of agents, for example, polynucleotide molecules and polypeptides associated with the synthesis of tocopherol and tocotrienol, and provides uses of such agents.

Tocopherol Biosynthesis

The tocopherol biosynthetic pathway in higher plants involves several enzymes (Fiedler et al., *Planta*, 155:511–515, 1982; Soll et al., *Arch. Biochem. Biophys.*, 204:544–550, 1980; Marshall et al., *Phytochem.*, 24:1705–1711, 1985) including HPPDs of the present invention. As used herein, an HPPD is a mononuclear, non-heme, iron containing enzyme that is a member of the family of 2-oxoacid dependent dioxygenases. HPPD catalyzes the conversion of 4-hydroxphenylpyruvate to homogentisic acid and is a key enzyme involved in the synthesis of α-tocopherol and plastoquinone. "Having HPPD activity" means that the HPPD enzyme (EC 1.13.11.27) uses molecular oxygen to oxygenate 4-hydroxyphenylpyruvate to yield $CO_2$ and homogentisic acid.

The present invention is useful for: 1) increasing tocopherol and tocotrienol production in plants; 2) enhancing the nutritional quality of human food and animal feed; 3) enhancing tolerance in plants to abiotic stresses such as heat and drought; and 4) increasing the tolerance of plants to certain classes of herbicides.

Tocopherols are involved in the response of plants to oxidative stresses (Porfirova et al., *PNAS*, 99(19):12495–12500, 2002). Therefore, expression or overexpression in a transformed plant of an HPPD or polypeptide having HPPD activity of the present invention, in combination with other tocopherol pathway enzymes, may provide tolerance to a variety of stresses, e.g., oxidative stress tolerance such as to drought, oxygen or ozone, UV tolerance, cold tolerance, or fungal/microbial pathogen tolerance. Environmental stresses, such as drought, increased salinity of soil, and extreme temperature, are major factors in limiting plant growth and productivity. The worldwide loss in yield of three major cereal crops, rice, maize (corn), and wheat due to water stress (drought) has been estimated to be over ten billion dollars annually. However, conventional breeding is a slow process for generating crop varieties with improved tolerance to stress conditions. Limited germplasm resources for stress tolerance and incompatibility in crosses between distantly related plant species are additional problems encountered in conventional breeding. Recent progress in plant genetic transformation and availability of potentially useful genes characterized from different sources make it possible to generate stress-tolerant crops using transgenic approaches (U.S. Pat. No. 5,981,842). Since HPPD plays a key role in the production of plant tocopherols, compositions of the present invention can be used to produce plants that are more tolerant of abiotic stresses.

The plastids of higher plants exhibit interconnected biochemical pathways leading to secondary metabolites including tocopherols as illustrated in FIG. 1. The various genes and their encoded proteins involved in tocopherol biosynthesis are listed in Table 1 below.

TABLE 1

Tocopherol biosynthetic coding regions and enzymes

| Coding region or Enzyme Abbreviation | Enzyme name |
|---|---|
| tyrA | Mono or bifunctional prephenate dehydrogenase |
| HPT | Homogentisate prenyl transferase |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| IDI | Isopentenyl diphosphate isomerase |
| MT1 | Bacterial 2-methylphytylplastoquinol methyltransferase |
| tMT2 | Plant 2-methylphytylplastoquinol methyltransferase |
| GGH | Geranylgeranyl diphosphate reductase |
| slr1737 | Tocopherol cyclase |
| GMT | Tocopherol gamma methyl transferase |
| LTT1 | Phytol kinase |
| Chl1 and Chl2 | Chlorophyllase 1 and 2 |

The tocopherol biosynthetic pathway in higher plants involves condensation of homogentisic acid and phytylpyrophosphate to form 2-methylphytylplastoquinol (Fiedler et al., Planta, 155:511–515, 1982; Soll et al., Arch. Biochem. Biophys., 204:544–550, 1980; Marshall et al., Phytochem., 24:1705–1711, 1985). This plant tocopherol pathway can be divided into four parts: 1) synthesis of homogentisic acid (HGA), which contributes to the aromatic ring of tocopherol; 2) synthesis of phytylpyrophosphate, which contributes to the side chain of tocopherol; 3) joining of HGA and phytylpyrophosphate via a prenyltransferase followed by a methylation reaction, and a subsequent cyclization; and 4) another S-adenosyl methionine dependent methylation of an aromatic ring, which affects the relative abundance of each of the tocopherol species.

Synthesis of Homogentisic Acid

Homogentisic acid is the common precursor to both tocopherols and plastoquinones (FIG. 1). In at least some bacteria, the synthesis of homogentisic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include, for example, the proteins encoded by the tyrA genes of Erwinia herbicola (SEQ ID NO: 25) and Escherichia coli. The tyrA gene product catalyzes the production of prephenate from chorismate, as well as the subsequent dehydrogenation of prephenate to form p-hydroxyphenylpyruvate (p-HPP), the immediate precursor to homogentisic acid. p-HPP is then converted to homogentisic acid by p-hydroxyphenylpyruvate dioxygenase (HPPD). In contrast, plants are believed to lack prephenate dehydrogenase activity, and it is generally believed that the synthesis of homogentisic acid from chorismate occurs via the synthesis and conversion of the intermediates arogenate, tyrosine, and p-hydroxyphenylpyruvate. Since pathways involved in homogentisic acid synthesis are also responsible for tyrosine formation, any alterations in these pathways can also result in the alteration in tyrosine synthesis and the synthesis of other aromatic amino acids. Therefore, it is useful for the enhancement of tocopherol production to combine the expression of genes encoding HPPD and tyrA.

Synthesis of Phytylpyrophosphate

Tocopherols are a member of the class of compounds referred to as the isoprenoids. Other isoprenoids include carotenoids, gibberellins, terpenes, chlorophyll, and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., Chem. Bio., 5:R221–R233, 1998; Rohmer, Prog. Drug. Res., 50:135–154, 1998; Rohmer, Comprehensive Natural Products Chemistry, 2:45–68, Barton and Nakanishi Eds., Pergamon Press, Oxford, England, 1999), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the Methylerythritol phosphate (MEP) pathway (Rohmer et al., Biochem. J., 295:517–524, 1993; Schwarz, Ph.D. thesis, Eidgenössiche Technische Hochschule, Zurich, Switzerland, 1994). Recent studies showed the formation of 1-deoxyxylulose 5-phosphate and pyruvate (Broers, Ph.D. thesis, Eidgenössiche Technische Hochschule, Zurich, Switzerland, 1994) from one molecule each of glyceraldehyde 3-phosphate and pyruvate (Rohmer, Comprehensive Natural Products Chemistry, 2:45–68; Barton and Nakanishi, Eds., Pergamon Press, Oxford, England, 1999; Eisenreich et al., Chem. Biol., 5:R223–R233, 1998; Schwarz supra; Rohmer et al., J. Am. Chem. Soc., 118: 2564–2566, 1996; Sprenger et al., Proc. Natl. Acad. Sci. (U.S.A.), 94:12857–12862, 1997) by an enzyme encoded by the dxs gene (Lois et al., Proc. Natl. Acad. Sci. (U.S.A.), 95:2105–2110, 1997; U.S. Publication 2003/0125573; Lange et al., Proc. Natl. Acad. Sci. (U.S.A.), 95:2100–2104, 1998). 1-Deoxyxylulose 5-phosphate can be further converted into 2-C-methylerythritol 4-phosphate (Arigoni et al.,

*Proc. Natl. Acad. Sci. (U.S.A.)*, 94:10600–10605, 1997) by a reductoisomerase encoded by the dxr gene (Bouvier et al., *Plant Physiol.*, 117:1421–1431, 1998; Rohdich et al., *Proc. Natl. Acad. Sci. (U.S.A.)*, 96:11758–11763, 1999).

Genes reported to be in the MEP pathway also include ygbP, which catalyzes the conversion of 2-C-methyl-D-erythritol 4-phosphate into its respective cytidyl pyrophosphate derivative. The translation product of ychB, in turn catalyzes the conversion of 4-phosphocytidyl-2-C-methyl-D-erythritol into 4-diphosphocytidyl-2-C-methyl-D-erythritol-2 phosphate. The latter compound is converted by the action of the translation product of ygbB into 2-C-methyl-D-erythritol,2,4-cyclodiphosphate. Subsequently, 2-C-methyl-D-erythritol-2,4-cyclodiphosphate is converted by the translation product of gcpE to (E)-1-(4-hydroxy-3-methyl-but-2-enyl) diphosphate. The latter compound is converted by the action of LytB to IPP and DMAPP (Herz et al., *Proc. Natl. Acad. Sci. (U.S.A.)*, 97(6):2485–2490, 2000).

Once IPP is formed by the MEP pathway, it is converted to GGDP by GGPPS synthase, and then to phytylpyrophosphate (Phytyl-PP), which is the central constituent of the tocopherol side chain. Phytyl-PP is a substrate for HPT, the enzyme immediately succeeding HPPD in the tocopherol biosynthectic pathway. Therefore, it is useful to combine the expression of genes encoding HPT and HPPD to enhanced production of tocopherol.

Combination and Cyclization

HPPD enzymatic activity provides Homogentisic acid, which is combined with either phytylpyrophosphate or solanyl-pyrophosphate by homogentisate prenyl transferase forming 2-methylphytyl plastoquinol or 2-methylsolanyl plastoquinol, respectively. 2-Methylsolanyl plastoquinol is a precursor to the biosynthesis of plastoquinones, while 2-methylphytyl plastoquinol is ultimately converted to tocopherol. It has been suggested that homogentisic acid, when combined with geranylgeranylpyrophosphate, will lead to the formation of tocotrienols.

Methylation of the Aromatic Ring

The substrates for the completion of tocopherol biosynthesis are produced by the enzymatic activities of GGH, LTT1, HPPD, and HPT. The major structural differences between each of the tocopherol subtypes are then determined by the position of the methyl groups around the phenyl ring. Both 2-methylphytyl plastoquinol and 2-methylsolanyl plastoquinol serve as substrates for the plant enzyme 2-methylphytylplastoquinol/2-methylsolanylplastoquinol methyltransferase (2-methylphytylplastoquinol methyltransferase; methylphytylplastoquinol methyltransferase; MT2; tMT2), which is capable of methylating a tocopherol precursor to form 2,3-dimethyl-5-phytylplastoquinol, the cyclization of which by tocopherol cyclase yields γ-tocopherol (Cheng et al., *Plant Cell*, 15:2343–2356, 1983). Subsequent methylation of γ-tocopherol by γ-tocopherol methyl-transferase (GMT) generates α-tocopherol (Shintani et al., *Science*, 282:2098–2100, 1998).

A possible alternate pathway for the generation of α-tocopherol involves the generation of δ-tocopherol via the cyclization of 2-methylphytylplastoquinol by tocopherol cyclase. δ-tocopherol is then converted to β-tocopherol via the methylation of the 5 position by GMT. δ-tocopherol can be converted to α-tocopherol via the methylation of the 3 position by tMT2, followed by methylation of the 5 position by GMT. In a possible alternative pathway, β-tocopherol is directly converted to α-tocopherol by tMT2 via the methylation of the 3 position (see, for example, *Biochemical Society Transactions*, 11:504–510, 1983; Introduction to *Plant Biochemistry*, 2$^{nd}$ edition, Chapter 11, 1983; *Vitamin Hormone*, 29:153–200, 1971; *Biochemical Journal*, 109: 577, 1968; *Biochemical and Biophysical Research Communication*, 28(3):295, 1967). Since all potential mechanisms for the generation of α-tocopherol involve catalysis by tMT2, plants that are deficient in this activity accumulate δ-tocopherol and β-tocopherol. Plants that have increased tMT2 activity tend to accumulate γ-tocopherol and α-tocopherol. Since there is a low level of GMT activity in the seeds of many plants, these plants tend to accumulate γ-tocopherol.

The agents of the present invention will preferably be "biologically active" with respect to either a structural attribute, such as the capacity of a polynucleotide to hybridize to another polynucleotide molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The term "substantially purified" is not intended to encompass molecules present in their native environmental conditions.

The agents of the present invention may also be recombinant. As used herein, the term recombinant means any agent (e.g., DNA, peptide, etc.), that is, or results, however indirectly, from human manipulation of a polynucleotide molecule.

The agents of the present invention may also contain native or heterologous chloroplast transit peptides (CTP). Many chloroplast-localized proteins are expressed from nuclear genes as precursors and are targeted to the chloroplast by a chloroplast transit peptide (CTP) that is removed during the import steps. Examples of such chloroplast proteins include the small subunit (SSU) of Ribulose-1,5,-bisphosphate carboxylase (rubisco), Ferredoxin, Ferredoxin oxidoreductase, the light-harvesting complex protein I and protein II, and Thioredoxin F. It has been demonstrated in vivo and in vitro that non-chloroplast proteins may be targeted to plastids, e.g., chloroplasts, by use of protein fusions with a CTP and that a CTP sequence is sufficient to target a protein to the chloroplast. Chloroplast transit peptides can also be engineered to be fused to the N terminus of a HPPD molecule to direct HPPD enzymes into the plant chloroplast. The native CTP may be substituted with a heterologous CTP during construction of a transgene plant expression cassette. For example, incorporation of a suitable chloroplast transit peptide, such as, the *Arabidopsis thaliana* EPSPS CTP (CTP2, Klee et al., *Mol. Gen. Genet.*, 210: 437–442, 1987), or the *Petunia hybrida* EPSPS CTP (CTP1, della-Cioppa et al., *Proc. Natl. Acad. Sci. (U.S.A.)*, 83:6873–6877, 1986) has been shown to target heterologous EPSPS protein sequences to chloroplasts in transgenic plants. Those skilled in the art will recognize that various chimeric constructs can be made that utilize the functionality of a particular CTP to import HPPD enzymes into the plant cell chloroplast.

It is understood that the agents of the present invention may be labeled with reagents that facilitate detection of the agent (e.g., fluorescent labels, Prober et al., *Science*, 238: 336–340, 1987; Albarella et al., European Patent 144914; chemical labels, Sheldon et al., U.S. Pat. No. 4,582,789; Albarella et al., U.S. Pat. No. 4,563,417; modified bases, Miyoshi et al., European Patent 119448).

As used herein in a preferred aspect, a tolerance or resistance to stress is determined by the ability of a plant, when challenged by a stress such as drought, to produce a plant having a higher yield or to a plant being less susceptible to an environmentally induced phenotype such as wilting, than one without such tolerance or resistance to stress. In a particularly preferred aspect of the present invention, the tolerance or resistance to stress is measured relative to a plant with a similar genetic background to the tolerant or resistance plant except that the plant expresses or over expresses a protein or fragment thereof of the present invention.

Polynucleotide Molecules

The present invention includes and provides polynucleotide molecules encoding a polypeptide comprising a sequence selected from the group consisting of SEQ ID NOs: 4, 6, 10, 12, 16, 18, 20, 22, and 24.

The present invention includes and provides a polynucleotide molecule encoding an HPPD polypeptide, or a polypeptide having HPPD activity, comprising a polypeptide sequence having at least 58%, 60%, 65%, 70%, 75%, 80%, 85%, 90%, 95%, or 99% identity to SEQ ID NO: 4, 6, 10, or 12.

The present invention includes and provides a polynucleotide molecule encoding an HPPD polypeptide, or a polypeptide having HPPD activity, comprising a polypeptide sequence having at least 80%, 85%, 90%, 95%, or 99% identity to SEQ ID NO: 16.

The present invention includes and provides a polynucleotide molecule encoding an HPPD polypeptide, or a polypeptide having HPPD activity, comprising a polypeptide sequence having at least 80%, 85%, 90%, 95%, or 99% identity to SEQ ID NO: 18.

The present invention includes and provides a polynucleotide molecule encoding an HPPD polypeptide, or a polypeptide having HPPD activity, comprising a polypeptide sequence having at least 93%, 95%, or 99% identity to SEQ ID NO: 20.

The present invention includes and provides a polynucleotide molecule encoding an HPPD polypeptide, or a polypeptide having HPPD activity, comprising a polypeptide sequence having at least 79%, 80%, 85%, 90%, 95%, or 99% identity to SEQ ID NO: 22.

The present invention includes and provides a polynucleotide molecule encoding an HPPD polypeptide, or a polypeptide having HPPD activity, comprising a polypeptide sequence having at least 54%, 55%, 60%, 65%, 70%, 75%, 80%, 85%, 90%, 95%, or 99% identity to SEQ ID NO: 24.

The present invention includes and provides polynucleotide molecules comprising SEQ ID NO: 3, 5, 9, 11, or 13 and sequences having at least 80%, 85%, 90%, 95%, or 99% identity to such sequences.

The present invention includes and provides polynucleotide molecules comprising SEQ ID NO: 15 and sequences having at least 87%, 90%, 95%, or 99% identity to SEQ ID NO: 15.

The present invention includes and provides polynucleotide molecules comprising SEQ ID NO: 17 and sequences having at least 87%, 90%, 95%, or 99% identity to SEQ ID NO: 17.

The present invention includes and provides polynucleotide molecules comprising SEQ ID NO: 19 and sequences having at least 91%, 95%, or 99% identity to SEQ ID NO: 19.

The present invention includes and provides polynucleotide molecules comprising SEQ ID NO: 21 and sequences having at least 91%, 95%, or 99% identity to SEQ ID NO: 21.

The present invention includes and provides polynucleotide molecules comprising SEQ ID NO: 23 and sequences having at least 90%, 95%, or 99% identity to SEQ ID NO: 23.

The present invention includes and provides polynucleotide molecules described above and further comprising a nucleotide sequence selected from the group consisting of SEQ ID NOs: 25, 26, and 27.

In another preferred aspect of the present invention a polynucleotide molecule comprises nucleotide sequences encoding a plastid transit peptide operably fused to a polynucleotide molecule that encodes a protein or fragment of the present invention.

It is understood that in a further aspect of polynucleotide sequences of the present invention, the polynucleotides can encode a protein that differs from any of the proteins in that one or more amino acids have been deleted, substituted, or added without altering the function. For example, it is understood that codons capable of coding for such conservative amino acid substitutions are known in the art.

In one aspect of the present invention the polynucleotide of the present invention are said to be introduced polynucleotide molecules. A polynucleotide molecule is said to be "introduced" if it is inserted into a cell or organism as a result of human manipulation, no matter how indirect. Examples of introduced polynucleotide molecules include, without limitation, polynucleotides that have been introduced into cells via transformation, transfection, injection, and projection, and those that have been introduced into an organism via conjugation, endocytosis, phagocytosis, etc.

One subset of the polynucleotide molecules of the present invention is fragment polynucleotide molecules. Fragment polynucleotide molecules may consist of significant portion(s) of, or indeed most of, the polynucleotide molecules of the present invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the polynucleotide molecules of the present invention may be a probe and specifically a PCR probe. A PCR probe is a polynucleotide molecule capable of initiating a polymerase activity while in a double-stranded structure with another polynucleotide. Various methods for determining the structure of PCR probes and PCR techniques exist in the art.

Polynucleotide molecules or fragments thereof of the present invention are capable of specifically hybridizing to other polynucleotide molecules under certain circumstances. Polynucleotide molecules of the present invention include those that specifically hybridize to polynucleotide molecules having a polynucleotide sequence selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23, and complements thereof. Polynucleotide molecules of the present invention also include those that specifically hybridize to polynucleotide molecules encoding a polypeptide sequence selected from the group consisting of: SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24, and fragments thereof.

As used herein, two polynucleotide molecules are said to be capable of specifically hybridizing to one another if the two molecules are capable of forming an anti-parallel, double-stranded polynucleotide structure.

A polynucleotide molecule is said to be the "complement" of another polynucleotide molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y., 2001, and by Haymes et al., *Nucleic Acid Hybridization, A Practical Approach*, IRL Press, Washington, D.C., 1985. Departures from complete complementarity are therefore permissible, as long as such departures do not completely preclude the capacity of the molecules to form a double-stranded structure. Thus, in order for a polynucleotide molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 20–25° C., are known to those skilled in the art or can be found in *Current Protocols in Molecular Biology*, John Wiley & Sons, New York, 1989, 6.3.1–6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a polynucleotide of the present invention will specifically hybridize to one or more of the polynucleotide molecules set forth in: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23, and complements thereof, under moderately stringent conditions, for example at about 2.0×SSC and about 65° C.

In a particularly preferred embodiment, a polynucleotide of the present invention will include those polynucleotide molecules that specifically hybridize to one or more of the polynucleotide molecules set forth in: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, a nucleotide sequence having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23, and complements thereof, under high stringency conditions such as 0.2×SSC and about 65° C.

In one embodiment of a method of the present invention, any of the polynucleotide sequences or polypeptide sequences, or fragments of either, of the present invention can be used to search for related sequences. As used herein, "search for related sequences" means any method of determining relatedness between two sequences, including, but not limited to, searches that compare sequence homology: for example, a PBLAST search of a database for relatedness to a single polypeptide sequence. Other searches may be conducted using profile based methods, such as the HMM (Hidden Markov model) META-MEME, which is maintained by South Dakota State University, SD, and PSI-BLAST, which is maintained by the National Center for Biotechnology Information, National Library of Medicine, National Institutes of Health (NCBI).

A polynucleotide molecule can encode for a substantially identical or substantially homologous polypeptide molecule. The degree of identity or homology is determined by use of computer software such as the WISCONSIN PACKAGE Gap Program. The Gap program in the WISCONSIN PACKAGE version 10.0-UNIX from Genetics Computer Group, Inc. is based on the method of Needleman and Wunsch, *J. Mol. Biol.*, 48:443–453, 1970. For comparisons described herein, the following sets of default parameters for pairwise comparisons were used: for amino acid sequence comparisons the Gap Creation Penalty=8 and the Gap Extension Penalty=2; for nucleotide sequence comparisons the Gap Creation Penalty=50 and the Gap Extension Penalty=3. Using the TBLASTN program in the BLAST 2.2.1 software suite (Altschul et al., *Nucleic Acids Res.*, 25:3389–3402, 1997), or using BLOSUM62 matrix (Henikoff and Henikoff, *Proc. Natl. Acad. Sci. (U.S.A.)*, 89:10915–10919, 1992), the set of default parameters for pairwise comparisons were: the gap creation cost=11 and the gap extension cost=1. In BLAST, the E-value, or expectation value, represents the number of different alignments with scores equivalent to or better than the raw alignment score, S, that are expected to occur in a database search by chance. The lower the E-value, the more significant the match. Because database size is an element in E-value calculations, E-values obtained by "BLASTing" against public databases, such as GenBank, have generally increased over time for any given query/entry match. "Percent identity" refers to the percentage of identically matched amino acid residues that exist along the length of that portion of the sequences which is aligned by the BLAST algorithm. In a preferred embodiment the percent identity calculations are performed using BLASTN or BLASTP (default, parameters, version 2.0.8, Altschul et al., *Nucleic Acids Res.*, 25:3389–3402, 1997).

A polynucleotide molecule of the present invention can also encode a homolog polypeptide. As used herein, a homolog polypeptide molecule or fragment thereof is a counterpart protein molecule or fragment thereof in a second species (e.g., corn rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see, for example, U.S. Pat. No. 5,811,238).

Agents of the present invention include polynucleotide molecules that encode polypeptides having at least about a contiguous 10 amino acid region of a polypeptide of the present invention, more preferably having at least about a contiguous 25, 40, 50, 100, or 125 amino acid region of a polypeptide of the present invention, preferably a polypeptide comprising SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24.

In a preferred embodiment, any of the polynucleotide molecules of the present invention can be operably linked to a promoter region that functions in a plant cell to cause the production of an mRNA molecule, where the polynucleotide molecule that is linked to the promoter is heterologous with respect to that promoter. As used herein, "heterologous" means not naturally occurring together.

Protein and Peptide Molecules

A class of agents includes one or more of the polypeptide molecules encoded by a polynucleotide agent of the present invention. A particular preferred class of polypeptides is that having a polypeptide sequence of SEQ ID NO: 4, 6, 10, or 12, or a sequence having at least 58%, 60%, 65%, 70%, 75%, 80%, 85%, 90%, 95%, or 99% identity to such sequence, or fragments thereof. A particular preferred class of polypeptides are those having a polypeptide sequence of SEQ ID NO: 16 or a sequence having at least 80%, 85%, 90%, 95%, or 99% identity to such sequence, or fragments thereof, those having a polypeptide sequence of SEQ ID NO: 18 or a sequence having at least 80%, 85%, 90%, 95%, or 99% identity to such sequence, or fragments thereof, those having a polypeptide sequence of SEQ ID NO: 20 or a sequence having at least 93%, 95%, or 99% identity to such sequence, or fragments thereof, those having a polypeptide sequence of SEQ ID NO: 22 or a sequence having at least 79%, 80%, 85%, 90%, 95%, or 99% identity to such sequence, or fragments thereof, or those having a polypeptide sequence of SEQ ID NO: 24 or a sequence having at least 54%, 55%, 60%, 65%, 70%, 75%, 80%, 85%, 90%, 95%, or 99% identity to such sequence, or fragments thereof.

In another aspect of the present invention, the HPPD polypeptide, or a polypeptide having HPPD activity, comprises a polypeptide sequence selected from the group consisting of SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24.

Polypeptide agents may have C-terminal or N-terminal amino acid sequence extensions. One class of N-terminal extensions employed in a preferred embodiment are plastid transit peptides. When employed, plastid transit peptides can be operatively linked to the N-terminal sequence, thereby permitting the localization of the agent polypeptides to plastids. In an embodiment of the present invention, any suitable plastid targeting sequence can be used (see, e.g., U.S. Pat. Nos. 5,776,760; 6,489,542; and 5,717,084). Where suitable, a plastid targeting sequence can be substituted for a native plastid targeting sequence. In a further embodiment, any suitable, modified plastid targeting sequence can be used. In another embodiment, e.g., the plastid targeting sequence is a CTP1 sequence (U.S. Pat. No. 5,776,760) or a CTP2 sequence (U.S. Pat. No. 5,463,175).

As used herein, the terms "protein," "peptide molecule," or "polypeptide" includes any molecule that comprises five or more amino acids. It is well known in the art that protein, peptide, or polypeptide molecules may undergo modification, including post-translational modifications, such as, but not limited to, disulfide bond formation, glycosylation, phosphorylation, or oligomerization. Thus, as used herein, the terms "protein," "peptide molecule," or "polypeptide" includes any protein that is modified by any biological or non-biological process. The phrases "amino acid" and "amino acids" refer to all naturally occurring L-amino acids. This definition is meant to include norleucine, norvaline, ornithine, homocysteine, and homoserine.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the present invention are preferably produced via recombinant means.

Plant Constructs and Plant Transformants

One or more of the polynucleotide molecules of the present invention may be used in plant transformation or transfection. Exogenous genetic material may be transferred into a plant cell and the plant cell regenerated into a whole, fertile, or sterile plant. Exogenous genetic material is any genetic material, whether naturally occurring or otherwise, from any source that is capable of being inserted into any organism.

In an aspect of the present invention, the exogenous genetic material comprises a polynucleotide sequence selected from the group consisting of SEQ ID NOs: 3, 5, 9, 11, and 13, and sequences having at least 80%, 85%, 90%, 95%, or 99% identity to at least one of SEQ ID NOs: 3, 5, 9, 11, and 13, or complements thereof and fragments of either. In a further aspect of the present invention, the exogenous genetic material comprises a polynucleotide sequence encoding a polypeptide sequence of SEQ ID NO: 4, 6, 10, or 12, and sequences having at least 58%, 60%, 65%, 70%, 75%, 80%, 85%, 90%, 95%, or 99% identity to such sequence, or fragments thereof.

In a preferred aspect of the present invention, the exogenous genetic material comprises a polynucleotide sequence of SEQ ID NO: 15, or polynucleotide sequences having at least 87%, 90%, 95%, or 99% identity to such sequence, or complements thereof and fragments of either. In a further aspect of the present invention, the exogenous genetic material comprises a polynucleotide sequence encoding a polypeptide sequence of SEQ ID NO: 16, and sequences having at least 80%, 85%, 90%, 95%, or 99% identity to such sequence, or fragments thereof.

In a preferred aspect of the present invention, the exogenous genetic material comprises a polynucleotide sequence of SEQ ID NO: 17, or polynucleotide sequences having at least 87%, 90%, 95%, or 99% identity to such sequence, or complements thereof and fragments of either. In a further aspect of the present invention, the exogenous genetic material comprises a polynucleotide sequence encoding a polypeptide sequence of SEQ ID NO: 18, and sequences having at least 80%, 85%, 90%, 95%, or 99% identity to such sequence, or fragments thereof.

In a preferred aspect of the present invention, the exogenous genetic material comprises a polynucleotide sequence of SEQ ID NO: 19, or polynucleotide sequences having at least 91%, 95%, or 99% identity to such sequence, or complements thereof and fragments of either. In a further aspect of the present invention, the exogenous genetic material comprises a polynucleotide sequence encoding a polypeptide sequence of SEQ ID NO: 20, and sequences having a least 93%, 95%, or 99% identity to such sequence, or fragments thereof.

In a preferred aspect of the present invention, the exogenous genetic material comprises a polynucleotide sequence of SEQ ID NO: 21, or polynucleotide sequences having at least 91%, 95%, or 99% identity to such sequence, or complements thereof and fragments of either. In a further aspect of the present invention, the exogenous genetic material comprises a polynucleotide sequence encoding a polypeptide sequence of SEQ ID NO: 22, and sequences having at least 79%, 80%, 85%, 90%, 95%, or 99% identity to such sequence, or fragments thereof.

In a preferred aspect of the present invention, the exogenous genetic material comprises a polynucleotide sequence of SEQ ID NO: 23, or polynucleotide sequences having at least 90% identity to such sequence, or complements thereof and fragments of either. In a further aspect of the present invention, the exogenous genetic material comprises a polynucleotide sequence encoding a polypeptide sequence of SEQ ID NO: 24, and sequences having at least 54%, 55%, 60%, 65%, 70%, 75%, 80%, 85%, 90%, 95%, or 99% identity to such sequence, or fragments thereof.

In a further aspect of the present invention, the polynucleotide sequences of the present invention also encode peptides involved in intracellular localization, export, or post-translational modification.

As used herein, the term "gene" includes a nucleic acid molecule that provides regulation of transcription that includes a promoter that functions in plants, 5' untranslated molecules, e.g., introns and leader sequences, a transcribed nucleic acid molecule and a 3' transcriptional termination molecule.

As used herein, the term "construct" is a plant expression cassette that includes all of the DNA regulatory molecules operably linked to the target molecule to provide expression in plants.

In an embodiment of the present invention, exogenous genetic material encoding an HPPD or fragment thereof is introduced into a plant with one or more additional genes. In one embodiment, preferred combinations of genes include a polynucleotide molecule of the present invention and one or more of the following genes: tyrA (e.g., PCT Publication WO 02/089561 incorporated herein by reference; Xia et al., *J. Gen. Microbiol.*, 138:1309–1316, 1992), tocopherol cyclase (e.g., PCT Publication WO 01/79472, incorporated herein by reference; Cyanobase—the genome database for cyanobacteria, which is maintained by the Department of Plant Gene Research, Kazusa DNA Research Institute, Japan), dxs (e.g., Lois et al., *Proc. Natl. Acad. Sci. (U.S.A.)*, 95(5):2105–2110, 1998), dxr (e.g., U.S. Publication 2002/0108148A, incorporated herein by reference; Takahashi et al., *Proc. Natl. Acad. Sci. (U.S.A.)*, 95(17):9879–9884, 1998), *GGPPS* (e.g., Bartley and Scolnik, *Plant Physiol.*, 104:1469–1470, 1994), GMT (e.g., U.S. patent application Ser. No. 10/219,810, filed Aug. 16, 2002, incorporated herein by reference; PCT Publications WO 03/016482; WO 00/32757; and WO 00/10380), HPT (U.S. Pat. No. 6,541, 259, incorporated herein by reference; PCT Publications WO 00/68393 and WO 00/63391; Smith et al., *Plant J*, 11:83–92, 1997), tMT2 (e.g., U.S. patent application Ser. No. 10/279,029, filed Oct. 24, 2002, incorporated herein by reference; PCT Publication WO 03/034812), AANT1 (e.g., PCT Publication WO 02/090506, incorporated herein by reference; Saint Guily et al., *Plant Physiol.*, 100(2):1069–1071, 1992), IDI (E.C.:5.3.3.2; ExPASy Molecular Biology Server; Blanc et al., In: *Plant Gene Register*, PRG96-036; Sato et al., *DNA Res.*, 4:215–230, 1997), GGH (Grasses et al., *Planta*, 213:620–628, 2001), or a plant ortholog and an antisense construct for homogentisic acid dioxygenase (Kridl et al., *Seed Sci. Res.*, 1:209–219, 1991; Sato et al., *J. DNA Res.*, 7(1):31–63, 2000; Keegstra, *Cell*, 56(2):247–53, 1989; Nawrath et al., *Proc. Natl. Acad. Sci.* (*U.S.A.*), 91:12760–12764, 1994), MT1 (e.g., PCT Publication WO 00/10380), gcpE (e.g. PCT Publication WO 02/12478, incorporated herein by reference), Ltt1 (e.g., U.S. patent application Ser. No. 10/634,548, filed Aug. 5, 2003, incorporated herein by reference), and chlorophyllase (e.g., *Arabidopsis chlorophyllase* 1, gi:30912637 and *Arabidopsis chlorophyllase* 2, gi:6729677; U.S. patent application Ser. No. 10/634,548, incorporated herein by reference). In such combinations, in some crop plants, e.g., canola, a preferred promoter is a napin promoter and a plastid targeting sequence is a CTP1 or CTP2 sequence. Gene products may be targeted to the plastid. Alternatively, one or more of the gene products can be localized in the cytoplasm. In one embodiment, the gene products of tyrA and HPPD are targeted to the plastids. In a second embodiment, tyrA and HPPD are targeted to the cytoplasm. Such genes can be introduced, for example, on a single construct, introduced on different constructs but the same transformation event, or introduced into separate plants followed by one or more crosses to generate the desired combination of genes. In such combinations, a preferred promoter is a napin promoter (U.S. Pat. No. 5,420,034), a 7S alpha promoter (U.S. Publication 2003/0093828), the 7S beta promoter (Lessard et al., *Plant Molecular Biology*, 22(5):873–875, 1993), the Arcelin 5 promoter (PCT Publication WO 02/50295), the USP 88 promoter (U.S. patent application Ser. No. 10/429,516, filed May 6, 2003), and a preferred plastid targeting sequence is a CTP1 or CTP2 sequence. The seed-specific promoters that include the 5' regulatory regions of the napin gene provide expression of transgenes in seed tissues (U.S. Pat. Nos. 5,420,034 and 6,459,018, herein incorporated by reference). In soybean, 7S refers to β-conglycinin, a major class of seed storage proteins. The trimeric β-conglycinin is comprised of the α, α', and β subunits. Expression of 7Sα' has been well studied by many researchers over the years. The 7Sα' subunit is expressed at mid to late stages of seed development. A transgene encoding the α'-subunit of soybean β-conglycinin showed seed-specific expression in petunia (Beachy et al., *EMBO J.*, 4:3047–3053, 1985). Functional analysis of the regulatory elements indicated that a 900 bp upstream fragment of the 7Sα' promoter contains the necessary elements to produce seed-specific expression in transgenic petunia (Chen et al., *Proc. Natl. Acad. Sci.* (*U.S.A.*), 83:8560–8564, 1986). The sequences of the promoters disclosed in these referenced patents are herein incorporated by reference.

In a preferred combination, a polynucleotide molecule of the present invention and a polynucleotide molecule encoding any of the following enzymes: tyrA (SEQ ID NO: 25), HPT (SEQ ID NO: 26), tocopherol cyclase, chlorophyllase, LTT1, dxs, dxr, GGPPS, tMT2, AANT1, IDI, GMT, GGH (SEQ ID NO: 27), or a plant ortholog and an antisense construct for homogentisic acid dioxygenase are introduced into a plant.

In a preferred combination, a polynucleotide molecule of the present invention and a polynucleotide molecule encoding tyrA (SEQ ID NO: 25), HPT (SEQ ID NO: 26), GGH (SEQ ID NO: 27), GMT, and tMT2 are introduced into a plant.

Such genetic material may be transferred into either monocotyledons or dicotyledons including, but not limited to alfalfa, apple, *Arabidopsis*, banana, *Brassica campestris*, canola, castor bean, coffee, corn, cotton, cottonseed, chrysanthemum, crambe, cucumber, dendrobium, *dioscorea*, *eucalyptus*, fescue, flax, gladiolus, liliacea, linseed, millet, muskmelon, mustard, oat, oil palms, oilseed rape, peanut, perennial ryegrass, *Phaseolus*, rapeseed, rice, sorghum, soybean, rye, tritordeum, turfgrass, wheat, safflower, sesame, sugarbeet, sugarcane, cranberry, papaya, safflower, and sunflower (Christou, In: *Particle Bombardment for Genetic Engineering of Plants*, Biotechnology Intelligence Unit. Academic Press, San Diego, Calif., 1996). In a preferred embodiment, the genetic material is transferred into canola. In another more preferred embodiment, the genetic material is transferred into oilseed rape. In another particularly preferred embodiment, the genetic material is transferred into soybean.

Transfer of a polynucleotide molecule that encodes a protein can result in expression or overexpression of that polypeptide in a transformed cell or transgenic plant. One or more of the proteins or fragments thereof encoded by polynucleotide molecules of the present invention may be overexpressed in a transformed cell or transformed plant.

In a preferred embodiment, DNA constructs of the present invention comprising SEQ ID NO: 3, 5, 7, 9, 11, or 13, or sequences having at least 80%, 85%, 90%, 95%, or 99% identity to such sequence, provide in a transformed plant, relative to an untransformed plant with a similar genetic background, an increased level of tocopherols. In a preferred embodiment, DNA constructs of the present invention comprising SEQ ID NO: 15, or sequences having at least 87%, 90%, 95%, or 99% identity to SEQ ID NO: 15, provide in a transformed plant, relative to an untransformed plant with a similar genetic background, an increased level of tocopherols. In a preferred embodiment, DNA constructs of the present invention comprising SEQ ID NO: 17, or sequences having at least 87%, 90%, 95%, or 99% identity to SEQ ID NO: 17, provide in a transformed plant, relative to an untransformed plant with a similar genetic background, an increased level of tocopherols. In a preferred embodiment, DNA constructs of the present invention comprising SEQ ID NO: 19, or sequences having at least 91%, 95%, or 99% identity to SEQ ID NO: 19, provide in a transformed plant, relative to an untransformed plant with a similar genetic background, an increased level of tocopherols. In a preferred embodiment, DNA constructs of the present invention comprising SEQ ID NO: 21, or sequences having at least 91%, 95%, or 99% identity to SEQ ID NO: 21, provide in a transformed plant, relative to an untransformed plant with a similar genetic background, an increased level of tocopherols. In a preferred embodiment, DNA constructs of the present invention comprising SEQ ID NO: 23, or sequences having at least 90%, 95%, or 99% identity to SEQ ID NO: 23, provide in a transformed plant, relative to an untransformed plant with a similar genetic background, an increased level of tocopherols. As used in this paragraph, tocopherols include α-tocopherols, β-tocopherols, δ-tocopherols, and γ-tocopherols as well as α-tocotrienols, β-tocotrienols, δ-tocotrienols, and γ-tocotrienols.

In a preferred embodiment, DNA constructs of the present invention comprising SEQ ID NO: 3, 5, 7, 9, 11, or 13, or sequences having at least 80%, 85%, 90%, 95%, or 99% identity to such sequences provide in a transformed plant, relative to an untransformed plant with a similar genetic background, an increased level of plastoquinols.

In a preferred embodiment, DNA constructs of the present invention comprising SEQ ID NO: 15, or sequences having at least 87%, 90%, 95%, or 99% identity to SEQ ID NO: 15, provide in a transformed plant, relative to an untransformed plant with a similar genetic background, an increased level of plastoquinols.

In a preferred embodiment, DNA constructs of the present invention comprising SEQ ID NO: 17, or sequences having at least 87%, 90%, 95%, or 99% identity to SEQ ID NO: 17, provide in a transformed plant, relative to an untransformed plant with a similar genetic background, an increased level of plastoquinols.

In a preferred embodiment, DNA constructs of the present invention comprising SEQ ID NO: 19, or sequences having at least 91%, 95%, or 99% identity to SEQ ID NO: 19, provide in a transformed plant, relative to an untransformed plant with a similar genetic background, an increased level of plastoquinols.

In a preferred embodiment, DNA constructs of the present invention comprising SEQ ID NO: 21, or sequences having at least 91%, 95%, or 99% identity to SEQ ID NO: 21, provide in a transformed plant, relative to an untransformed plant with a similar genetic background, an increased level of plastoquinols.

In a preferred embodiment, DNA constructs of the present invention comprising SEQ ID NO: 23, or sequences having at least 90%, 95%, or 99% identity to SEQ ID NO: 23, provide in a transformed plant, relative to an untransformed plant with a similar genetic background, an increased level of plastoquinols.

In a preferred embodiment, DNA constructs of the present invention comprising polynucleotide molecules encoding a polypeptide comprising a polypeptide sequence selected from the group consisting of SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 8, a polypeptide sequence having at least 58% identity to SEQ ID NO: 8, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24; and provide in a transformed plant, relative to an untransformed plant with a similar genetic background, an increased level of tocopherols. As used in this paragraph, tocopherols include α-tocopherols, β-tocopherols, δ-tocopherols, and γ-tocopherols as well as α-tocotrienols, β-tocotrienols, δ-tocotrienols, and γ-tocotrienols.

In a preferred embodiment, DNA constructs of the present invention comprising polynucleotide molecules encoding polypeptides of the present invention provide in a transformed plant, relative to an untransformed plant with a similar genetic background, an increased level of plastoquinols.

In one embodiment, DNA constructs of the present invention comprising a polynucleotide selected from the group consisting of: SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 7, a nucleotide sequence having at least 80% identity to SEQ ID NO: 7, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, nucleotide sequences having at least 80% identity to SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23, provide in a transformed plant, relative to an untransformed plant with a similar genetic background, a decreased level of tocopherols, α-tocopherols, γ-tocopherols, δ-tocopherols, β-tocopherols, tocotrienols, α-tocotrienols, γ-tocotrienols, δ-tocotrienols, β-tocotrienols, and/or plastoquinols.

In any of the embodiments described herein, an increase in γ-tocopherol, α-tocopherol, or both can lead to a decrease in the relative proportion of β-tocopherol, δ-tocopherol, or both. Similarly, an increase in γ-tocotrienol, α-tocotrienol, or both can lead to a decrease in the relative proportion of β-tocotrienol, δ-tocotrienol, or both.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols are measurably increased. The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds, and flowers. A preferred organ is a seed. In a preferred embodiment, expression of enzymes involved in tocopherol, tocotrienol, or plastoquinol synthesis in the seed will result in an increase in γ-tocopherol levels due to the absence of significant levels of GMT activity in those tissues. In another preferred embodiment, expression of enzymes involved in tocopherol, tocotrienol, or plastoquinol synthesis in photosynthetic tissues will result in an increase in α-tocopherol due to the higher levels of GMT activity in those tissues relative to the same activity in seed tissue.

In another preferred embodiment, the expression of enzymes involved in tocopherol, tocotrienol, or plastoquinol synthesis in the seed will result in an increase in the total tocopherol, tocotrienol, or plastoquinol level in the plant.

In some embodiments, the levels of tocopherols or a species such as α-tocopherol may be altered. In some embodiments, the levels of tocotrienols may be altered. Such alteration can be compared to a plant with a similar genetic background but lacking the introduction of a polynucleotide sequence of the present invention.

In another embodiment, either the α-tocopherol level, α-tocotrienol level, or both of plants that natively produce high levels of either α-tocopherol, α-tocotrienol or both (e.g., sunflowers), can be increased by the introduction of a polynucleotide of the present invention.

As tocotrienols have their own health benefits, the nucleotide sequence of HPPD and nucleotide sequences encoding HPPD polypeptides and polypeptides having HPPD activity can also be used to obtain transgenic seed that predominantly accumulate tocotrienols. Tocotrienols can be obtained in dicotyledonous seed that carry seed-specific expression constructs for the prephenate dehydrogenase (tyrA) and the HPPD (PCT Publication WO 02/089561). A higher purity of tocotrienols may be obtained in such seed by reducing the production of tocopherols while increasing the production of tocotrienols.

Gene replacement technology can be used to increase expression of a given gene. Gene replacement technology is based upon homologous recombination (see, Schnable et al., *Curr. Opinions Plant Biol.*, 1:123, 1998). The polynucleotide of the enzyme of interest can be manipulated by mutagenesis (e.g., insertions, deletions, duplications, or replacements) to either increase or decrease enzymatic function. The altered sequence can be introduced into the genome to replace the existing, e.g., wild-type, gene via homologous recombination (Puchta and Hohn, *Trends Plant Sci.*, 1:340, 1996; Kempin et al., *Nature*, 389:802, 1997).

In a preferred aspect, a similar genetic background is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

Exogenous genetic material may be transferred into a host plant cell by the use of a DNA vector or construct designed for such a purpose. Design of such a vector is generally within the skill of the art (see, *Plant Molecular Biology: A Laboratory Manual*, Clark (ed.), Springer, New York, 1997).

A construct or vector may include a plant promoter to express an mRNA that is translated into the polypeptide of choice. In a preferred embodiment, any polynucleotide molecules described herein can be operably linked to a promoter region that functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter or a plant virus promoter.

A number of promoters that are active in plant cells have been described in the literature. These include the 7S alpha' promoter, the USP 88 promoter (U.S. patent application Ser. No. 10/429,516, filed May 5, 2003), the nopaline synthase (NOS) promoter (Ebert et al., *Proc. Natl. Acad. Sci. (U.S.A.)*, 84:5745–5749, 1987), the octopine synthase (OCS) promoter which is carried on tumor-inducing plasmids of *Agrobacterium tumefaciens*. Examples of constitutive promoters that are active in plant cells include, but are not limited to the nopaline synthase (P-NOS) promoters; the cauliflower mosaic virus (P-CaMV) 19S and 35S(P-CaMV35S, U.S. Pat. No. 5,858,642) and enhanced versions of the CaMV 35S promoter (P-CaMV35S-enh, U.S. Pat. No. 5,322,938); the figwort mosaic virus promoter (P-FMV35S, U.S. Pat. Nos. 6,051,753 and 6,018,100); actin promoters, such as the rice actin promoter (P-Os.Act1, U.S. Pat. No. 5,641,876), the Adh promoter (Walker et al., *Proc. Natl. Acad. Sci. (U.S.A.)*, 84:6624–6628, 1987), the sucrose synthase promoter (Yang et al., *Proc. Natl. Acad. Sci. (U.S.A.)*, 87:4144–4148, 1990), the R gene complex promoter (Chandler et al., *The Plant Cell*, 1:1175–1183, 1989); and the chlorophyll a/b binding protein gene promoter, etc. These promoters have been used to create DNA constructs that have been expressed in plants. Promoters known or found to cause transcription of DNA in plant cells can be used in the present invention. The sequences of the promoters disclosed in these referenced patents are herein incorporated by reference.

For the purpose of expression in source tissues of the plant, such as the leaf, seed, root, or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci. (U.S.A.)*, 87:3459–3463, 1990), the chloroplast fructose-1, 6-biphosphatase (FBPase) promoter from wheat (Lloyd et al., *Mol. Gen. Genet.*, 225:209–216, 1991), the nuclear photosynthetic ST-LS1 promoter from potato (Stockhaus et al., *EMBO J.*, 8:2445–2451, 1989), the serine/threonine kinase promoter (Hardie DG (1999), *Ann Rev Plant Physiol Plant Mol. Biol.*, 50:97–131; U.S. Pat. No. 6,653,533) and the glucoamylase promoter (Henricksen et al., Microbiology-UK, 145:729–734 Part 3 (1999). Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.*, 35:773–778, 1994), the promoter for the cab1 gene from wheat (Fejes et al., *Plant Mol. Biol.*, 15:921–932, 1990), the promoter for the cab1 gene from spinach (Lubberstedt et al., *Plant Physiol.*, 104:997–1006, 1994), the promoter for the cab1R gene from rice (Luan et al., *Plant Cell.*, 4:971–981, 1992), the pyruvate, orthophosphate dikinase (PPDK) promoter from corn (Matsuoka et al., *Proc. Natl. Acad. Sci. (U.S.A.)*, 90:9586–9590, 1993), the promoter for the tobacco Lhcb1*2 gene (Cerdan et al., *Plant Mol. Biol.*, 33:245–255, 1997), the *Arabidopsis thaliana* SUC2 sucrose-H+ symporter promoter (Truernit et al., *Planta.*, 196:564–570, 1995), and the promoter for the thylakoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (*Sinapis alba*; Kretsch et al., *Plant Mol. Biol.*, 28:219–229, 1995).

For the purpose of expression in sink tissues of the plant, such as the tuber of the potato plant, the fruit of tomato, or the seed of corn, wheat, rice, and barley, it is preferred that the promoters utilized in the present invention have relatively high expression in these specific tissues. A number of promoters for genes with tuber-specific or tuber-enhanced expression are known, including the class I patatin promoter (Bevan et al., *EMBO J.*, 8:1899–1906, 1986; Jefferson et al., *Plant Mol. Biol.*, 14:995–1006, 1990), the promoter for the potato tuber ADPGPP genes, both the large and small subunits, the sucrose synthase promoter (Salanoubat and Belliard, *Gene*, 60:47–56, 1987; Salanoubat and Belliard, *Gene*, 84:181–185, 1989), the promoter for the major tuber proteins including the 22 kd protein complexes and protease inhibitors (Hannapel, *Plant Physiol.*, 101:703–704, 1993), the promoter for the granule-bound starch synthase gene (GBSS) (Visser et al., *Plant Mol. Biol.*, 17:691–699, 1991), and other class I and II patatins promoters (Koster-Topfer et al., *Mol. Gen. Genet.*, 219:390–396, 1989; Mignery et al., *Gene*, 62:27–44, 1988).

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.*, 1:209–219, 1991), phaseolin (Bustos et al., *Plant Cell*, 1(9):839–853, 1989), soybean trypsin inhibitor (Riggs et al., *Plant Cell*, 1(6):609–621, 1989), ACP (Baerson et al., *Plant Mol. Biol.*, 22(2):255–267, 1993), stearoyl-ACP desaturase (Slocombe et al., *Plant Physiol.*, 104(4):167–176, 1994), soybean a' subunit of β-conglycinin (Chen et al., *Proc. Natl. Acad. Sci. (U.S.A.)*, 83:8560–8564, 1986), and oleosin (see, for example, Hong et al., *Plant Mol. Biol.*, 34(3):549–555, 1997). Further examples include the promoter for β-conglycinin (Chen et al., *Dev. Genet.*, 10:112–122, 1989). Also included are the zeins, which are a group of storage proteins, found in corn endosperm. Genomic clones for zein genes have been isolated (Pedersen et al., *Cell*, 29:1015–1026, 1982; Russell et al., *Transgenic Res.*, 6(2):157–168, 1997), and the promoters from these clones, including the 15 kD, 16 kD, 19 kD, 22 kD, 27 kD, and genes, could also be used. Other promoters known to function, for example, in corn include the promoters for the following genes: *waxy, Brittle, Shrunken 2*, Branching enzymes I and II, starch synthases, debranching enzymes, oleosins, glutelins, and sucrose synthases. A particularly preferred promoter for corn endosperm expression is the promoter for the glutelin gene from rice, more particularly the Osgt-1 promoter (Zheng et al., *Mol. Cell Biol.*, 13:5829–5842, 1993). Examples of promoters suitable for expression in wheat include those promoters for the ADP glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

The seed-specific promoters that include the 5' regulatory regions of the napin gene provide expression of transgenes in seed tissues (U.S. Pat. Nos. 5,420,034 and 6,459,018, herein incorporated by reference). In soybean, 7S refers to β-conglycinin, a major class of seed storage proteins. The trimeric β-conglycinin is comprised of the α, α', and β subunits. Expression of 7Sα' has been well studied by many researchers over the years. The 7Sα' subunit is expressed at mid to late stages of seed development. A transgene encoding the α'-subunit of soybean β-conglycinin showed seed-specific expression in petunia (Beachy et al., *EMBO J.*, 4:3047–3053, 1985). Functional analysis of the regulatory elements indicated that a 900 bp upstream fragment of the 7Sα' promoter contains the necessary elements to produce seed-specific expression in transgenic petunia (Chen et al., *Proc. Natl. Acad. Sci. (U.S.A.)*, 83:8560–8564, 1986). The ovule-specific promoter for BEL1 gene can also be used (Reiser et al., *Cell*, 83:735–742, 1995; GenBank No. U39944; Ray et al, *Proc. Natl. Acad. Sci. (U.S.A.)*, 91:5761–5765, 1994). The egg and central cell specific MEA (FIS1) and (FIS2) promoters are also useful reproductive tissue-specific promoters (Luo et al., *Proc. Natl. Acad. Sci. (U.S.A.)*, 97:10637–10642, 2000; Vielle-Calzada et al., *Genes Dev.*, 13:2971–2982, 1999). Additional promoters useful for driving expression of a transgene in seed tissues are described in numerous references, for example, U.S. Pat. Nos. 6,437,220; 6,426,447; 6,342,657; 6,410,828; 5,767,363; and 5,623,067, herein incorporated by reference.

A preferred promoter for expression in the seed is a napin promoter. Another preferred promoter for expression is an Arcelin5 promoter (U.S. Publication 2003/0046727). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

Constructs or vectors may also include, with the coding region of interest, a polynucleotide sequence that acts, in whole or in part, to terminate transcription of that region. A number of such sequences have been isolated, including the Tr7 3' sequence and the NOS 3' sequence (Ingelbrecht et al., *The Plant Cell*, 1:671–680, 1989; Bevan et al., *Nucleic Acids Res.*, 11:369–385, 1983). Regulatory transcript termination regions can be provided in plant expression constructs of this present invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention, e.g., TML 3' from *Agrobacterium tumefaciens* Ti plasmid.

A vector or construct may also include regulatory elements. Examples of such include the Adh intron 1 (Callis et al., *Genes and Develop.*, 1: 1183–1200, 1987), the sucrose synthase intron (Vasil et al., *Plant Physiol.*, 91:1575–1579, 1989), hsp70 (U.S. Pat. No. 5,859,347), and the TMV omega element (Gallie et al., *The Plant Cell*, 1:301–311, 1989). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.*, 199:183–188, 1985), which codes for kanamycin resistance and can be selected for using kanamycin, nptII, G418, hpt, etc.; a bar gene, which codes for bialaphos resistance; a mutant EPSP synthase gene (Hinchee et al., *Bio/Technology*, 6:915–922, 1988; Reynaerts et al., *Selectable and Screenable Markers*. In Gelvin and Schilperoort. *Plant Molecular Biology Manual*, Kluwer, Dordrecht, 1988; Jones et al., *Mol. Gen. Genet.*, 1987), which encodes glyphosate resistance; a nitrilase gene which confers resistance to bromoxynil (Stalker et al., *J. Biol. Chem.*, 263:6310–6314, 1988); a mutant acetolactate synthase gene (ALS) which confers imidazolinone or sulphonylurea resistance (EP 154204 (Sep. 11, 1985); D'Halluin et al., *Bio/Technology*, 10:309–314, 1992); and a methotrexate resistant DHFR gene (Thillet et al., *J. Biol. Chem.*, 263:12500–12508, 1988).

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.*, 5:387–405, 1987; Jefferson et al., *EMBO J*, 6:3901–3907, 1987); an R-locus gene, which encodes a product that regulates the production of anthocyanin pigments (red color) in plant tissues (Dellaporta et al., *Stadler Symposium*, 11:263–282, 1988); a β-lactamase gene (Sutcliffe et al., *Proc. Natl. Acad. Sci. (U.S.A.)*, 75:3737–3741, 1978); a gene which encodes an enzyme for which various chromogenic substrates are known (e.g., PADAC, a chromogenic cephalosporin); a luciferase gene (Ow et al., *Science,* 234:856–859, 1986); a xylE gene (Zukowsky et al., *Proc. Natl. Acad. Sci. (U.S.A.),* 80:1101–1105, 1983) which encodes a catechol dioxygenase that can convert chromogenic catechols; an α-amylase gene (Ikatu et al., *Bio/Technol.,* 8:241–242, 1990); a tyrosinase gene (Katz et al., *J. Gen. Microbiol.,* 129:2703–2714, 1983) which encodes an enzyme capable of oxidizing tyrosine to DOPA and dopaquinone which in turn condenses to melanin; an α-galactosidase, which will turn a chromogenic α-galactose substrate. Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art. In a preferred embodiment of the present invention, a transgenic plant expressing the desired protein is to be produced. Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Arabidopsis* embryos have been transformed by an *Agrobacterium* mediated vacuum infiltration method described by Bechtold, N. et al., *CR Acad Sci Paris Sciences di la vie/life sciences,* 316:1194–1199, 1993. This method has been modified for use with the constructs of the present invention to provide a rapid and efficient method to transform *Arabidopsis* and select for an herbicide tolerant phenotype. The methods for introducing transgenes into plants by *Agrobacterium*-mediated transformation utilize a T-DNA (transfer DNA) that incorporates the genetic elements of the transgene and transfers those genetic elements into the genome of a plant. Generally, the transgene(s) bordered by a right border DNA molecule (RB) and a left border DNA molecule (LB) is (are) transferred into the plant genome at a single locus.

"T-DNA molecule" refers to a DNA molecule that integrates into a plant genome via an *Agrobacterium* mediated transformation method. The ends of the T-DNA molecule are defined in the present invention as being flanked by the border regions of the T-DNA from *Agrobacterium* Ti plasmids. These border regions are generally referred to as the Right border (RB) and Left border (LB) regions and exist as variations in nucleotide sequence and length depending on whether they are derived from nopaline or octopine producing strains of *Agrobacterium*. The border regions commonly used in DNA constructs designed for transferring transgenes into plants are often several hundred polynucleotides in length and comprise a nick site where an endonuclease digests the DNA to provide a site for insertion into the genome of a plant. T-DNA molecules generally contain one or more plant expression cassettes.

An *Agrobacterium* strain ABI containing a DNA construct is prepared as inoculum by growing it in a culture tube containing 10 mls Luria Broth and antibiotics, for example, 1 ml/L each of spectinomycin (100 mg/ml), chloramphenicol (25 mg/ml), kanamycin (50 mg/ml), or the appropriate antibiotics as determined by those skilled in the art. The culture is shaken in the dark at 28° C. for approximately 16–20 hours.

The *Agrobacterium* inoculum is pelleted by centrifugation and resuspended in 25 ml Infiltration Medium (MS Basal Salts 0.5%, Gamborg's B-5 Vitamins 1%, Sucrose 5%, MES 0.5 g/L, pH 5.7) with 0.44 nM benzylaminopurine (10 ul of a 1.0 mg/L stock in DMSO per liter) and 0.02% Silwet L-77 to an $OD_{600}$ of 0.6.

Mature flowering *Arabidopsis* plants are vacuum infiltrated in a vacuum chamber with the *Agrobacterium* inoculum by inverting the pots containing the plants into the inoculum. The chamber is sealed, a vacuum is applied for several minutes, and released suddenly. The pots are blotted to remove excess inoculum, then covered with plastic domes and placed in a growth chamber at 21° C., 16 hours light, and 70% humidity. Approximately 2 weeks after vacuum infiltration of the inoculum, each plant is covered with a Lawson 511 pollination bag. Approximately 4 weeks post infiltration, water is withheld from the plants to permit dry down. The seed is harvested approximately 2 weeks after dry down.

With respect to microprojectile bombardment (U.S. Pat. Nos. 5,550,318; 5,538,880; and 5,610,042; each of which is specifically incorporated herein by reference in its entirety), particles are coated with polynucleotides and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication WO 95/06128), barley, wheat (U.S. Pat. No. 5,563,055, incorporated herein by reference in its entirety), rice, oat, rye, sugarcane, and sorghum; as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil-less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, *Physiol. Plant,* 15:473–497, 1962) or N6-based media (Chu et al., *Scientia Sinica,* 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

Any of the polynucleotide molecules of the present invention may be introduced into a plant cell in a permanent or transient manner in combination with other genetic elements such as vectors, promoters, enhancers, etc. Further, any of the polynucleotide molecules of the present invention may be introduced into a plant cell in a manner that allows for expression or overexpression of the protein or fragment thereof encoded by the polynucleotide molecule.

Antibodies have been expressed in plants (Hiatt et al., *Nature,* 342:76–78, 1989; Conrad and Fielder, *Plant Mol. Biol.,* 26:1023–1030, 1994). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.,* 16:4489–4496, 1997; Marion-Poll, *Trends in Plant Science,* 2:447–448, 1997). For example, expressed anti-abscisic antibodies have been reported to result in a general perturbation of seed development (Philips et al., *EMBO J.,* 16:4489–4496, 1997).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology,* 15:1313–1315, 1997; Baca et al., *Ann. Rev. Biophys. Biomol. Struct.,* 26:461–493, 1997). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289; and 5,194,585.

It is understood that any of the antibodies of the present invention may be expressed in plants and that such expression can result in a physiological effect. It is also understood that any of the expressed antibodies may be catalytic.

The present invention also provides for parts of the plants, particularly reproductive or storage parts, of the present invention. Plant parts, without limitation, include seed, endosperm, ovule, pollen, and tubers. In a particularly preferred embodiment of the present invention, the plant part is a seed. In one embodiment the seed (or grain) is a constituent of animal feed.

In another embodiment, the plant part is a fruit, more preferably a fruit with enhanced shelf life. In another preferred embodiment, the fruit has increased levels of a tocopherol. In another preferred embodiment, the fruit has increased levels of a tocotrienol.

Any of the plants or parts thereof of the present invention may be processed to produce a feed, meal, protein, or oil preparation, including oil preparations high in total tocopherol content and oil preparations high in any one or more of each tocopherol component listed herein. A particularly preferred plant part for this purpose is a seed. In a preferred embodiment the feed, meal, protein, or oil preparation is designed for livestock animals or humans, or both. Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than about 1, 5, 10, or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than about 0.5%, 1%, 5%, 10%, 25%, 50%, 75%, or 90% by volume or weight of the oil component of any product. In another embodiment, the oil preparation may be blended and can constitute greater than about 10%, 25%, 35%, 50%, or 75% of the blend by volume. Oil produced from a plant of the present invention can be admixed with one or more organic solvents or petroleum distillates.

Descriptions of breeding methods that are commonly used for different traits and crops can be found in one of several reference books (e.g., Hayward, *Plant Breeding: Principles and Prospects*, Vol. 1, Chapman & Hall, ISBN: 0412433907, 1993; Richards, A. J., *Plant Breeding Systems*, Stanley Thornes Pub Ltd; 2nd ed., ISBN: 0412574500, 1997; Allard, R. W., *Principles of Plant Breeding*, 2nd ed., John Wiley & Sons, ISBN: 0471023094, 1999).

A transgenic plant of the present invention may also be reproduced using apomixis. Apomixis is a genetically controlled method of reproduction in plants where the embryo is formed without union of an egg and a sperm. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art, e.g., U.S. Pat. No. 5,811,636.

Other Organisms

A polynucleotide of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Particularly preferred bacteria are *Agrobacteruim tumefaciens* and *E. coli*.

Methods to transform such cells or organisms are known in the art (EP 0 238 023; Yelton et al., *Proc. Natl. Acad. Sci. (U.S.A.)*, 81:1470–1474, 1984; Malardier et al., *Gene*, 78:147–156, 1989; Becker and Guarente, In: Abelson and Simon Eds., *Guide to Yeast Genetics and Molecular Biology, Method Enzymol.*, 194:182–187, Academic Press, Inc., New York; Ito et al., *J. Bacteriology*, 153:163, 1983; Hinnen et al., *Proc. Natl. Acad. Sci. (U.S.A.)*, 75:1920, 1978; Bennett and LaSure Eds., *More Gene Manipulations in Fungi*, Academic Press, California, 1991). Methods to produce proteins of the present invention are also known (Kudla et al., *EMBO*, 9:1355–1364, 1990; Jarai and Buxton, *Current Genetics*, 26:2238–2244, 1994; Verdier, *Yeast*, 6:271–297, 1990; MacKenzie et al., *Journal of Gen. Microbiol.*, 139: 2295–2307, 1993; Hartl et al., *TIBS*, 19:20–25, 1994; Bergenron et al., *TIBS*, 19:124–128, 1994; Demolder et al., *J. Biotechnology*, 32:179–189, 1994; Craig, *Science*, 260:1902–1903, 1993; Gething and Sambrook, *Nature*, 355: 33–45, 1992; Puig and Gilbert, *J. Biol. Chem.*, 269:7764–7771, 1994; Wang and Tsou, *FASEB Journal*, 7:1515–1517, 1993; Robinson et al., *Bio/Technology*, 1:381–384, 1994; Enderlin and Ogrydziak, *Yeast*, 10:67–79, 1994; Fuller et al., *Proc. Natl. Acad. Sci. (U.S.A.)*, 86:1434–1438, 1989; Julius et al., *Cell*, 37:1075–1089, 1984; Julius et al., *Cell*, 32:839–852, 1983).

In a preferred embodiment, DNA constructs of the present invention comprising SEQ ID NO: 3, 5, 7, 9, 11, or 13, or sequences having at least 80%, 85%, 90%, 95%, or 99% identity to such sequences, provide in a transformed cell, relative to an untransformed cell with a similar genetic background, an increased level of tocopherols. In a preferred embodiment, DNA constructs of the present invention comprising SEQ ID NO: 15, or sequences having at least 87%, 90%, 95%, or 99% identity to SEQ ID NO: 15, provide in a transformed cell, relative to an untransformed cell with a similar genetic background, an increased level of tocopherols. In a preferred embodiment, DNA constructs of the present invention comprising SEQ ID NO: 17, or sequences having at least 87%, 90%, 95%, or 99% identity to SEQ ID NO: 17, provide in a transformed cell, relative to an untransformed cell with a similar genetic background, an increased level of tocopherols. In a preferred embodiment, DNA constructs of the present invention comprising SEQ ID NO: 19, or sequences having at least 91%, 95%, or 99% identity to SEQ ID NO: 19, provide in a transformed cell, relative to an untransformed cell with a similar genetic background, an increased level of tocopherols. In a preferred embodiment, DNA constructs of the present invention comprising SEQ ID NO: 21, or sequences having at least 91%, 95%, or 99% identity to SEQ ID NO: 21, provide in a transformed cell, relative to an untransformed cell with a similar genetic background, an increased level of tocopherols. In a preferred embodiment, DNA constructs of the present invention comprising SEQ ID NO: 23, or sequences having at least 90%, 95%, or 99% identity to SEQ ID NO: 23, provide in a transformed cell, relative to an untransformed cell with a similar genetic background, an increased level of tocopherols. In a preferred embodiment, DNA constructs of the present invention comprising polynucleotide molecules encoding a polypeptide comprising a polypeptide sequence selected from the group consisting of SEQ ID NO: 4, a polypeptide sequence having at least 58% identity to SEQ ID NO: 4, SEQ ID NO: 6, a polypeptide sequence having at least 58% identity to SEQ ID NO: 6, SEQ ID NO: 8, a polypeptide sequence having at least 58% identity to SEQ ID NO: 8, SEQ ID NO: 10, a polypeptide sequence having at least 58% identity to SEQ ID NO: 10, SEQ ID NO: 12, a polypeptide sequence having at least 58% identity to SEQ ID NO: 12, SEQ ID NO: 16, a polypeptide sequence having at least 80% identity to SEQ ID NO: 16, SEQ ID NO: 18, a polypeptide sequence having at least 80% identity to SEQ ID NO: 18, SEQ ID NO: 20, a polypeptide sequence having at least 93% identity to SEQ ID NO: 20, SEQ ID NO: 22, a polypeptide sequence having at least 79% identity to SEQ ID NO: 22, SEQ ID NO: 24, and a polypeptide sequence having at least 54% identity to SEQ ID NO: 24; and provide in a transformed cell, relative to an untransformed cell with a similar genetic background, an increased level of tocopherols. As used in this paragraph, tocopherols include α-tocopherols, β-tocopherols, δ-tocopherols, and γ-tocopherols as well as α-tocotrienols, β-tocotrienols, δ-tocotrienols, and γ-tocotrienols.

In a preferred embodiment, DNA constructs of the present invention comprising polynucleotide molecules encoding polypeptides of the present invention provide in a transformed cell, relative to an untransformed cell with a similar genetic background, an increased level of plastoquinols.

Any of a variety of methods may be used to obtain one or more of the above-described polynucleotide molecules (Zamechik et al., *Proc. Natl. Acad. Sci. (U.S.A.)*, 83:4143–4146, 1986; Goodchild et al., *Proc. Natl. Acad. Sci. (U.S.A.)*, 85:5507–5511, 1988; Wickstrom et al., *Proc. Natl. Acad. Sci. (U.S.A.)*, 85:1028–1032, 1988; Holt et al., *Molec. Cell. Biol.*, 8:963–973, 1988; Gerwirtz et al., *Science*, 242:1303–1306, 1988; Anfossi et al., *Proc. Natl. Acad. Sci. (U.S.A.)*, 86:3379–3383, 1989; Becker et al., *EMBO J.*, 8:3685–3691, 1989). Automated polynucleotide synthesizers may be employed for this purpose. In lieu of such synthesis, the disclosed polynucleotide molecules may be used to define a pair of primers that can be used with the polymerase chain reaction (Mullis et al., *Cold Spring Har-* bor Symp. Quant. Biol., 51:263–273, 1986; Erlich et al., European Patents 50424; 84796; 258017; and 237362; Mullis, European Patent 201184; Mullis et al., U.S. Pat. No. 4,683,202; Erlich, U.S. Pat. No. 4,582,788; Saiki et al., U.S. Pat. No. 4,683,194) to amplify and obtain any desired polynucleotide molecule or fragment.

Promoter sequences and other genetic elements, including but not limited to transcriptional regulatory flanking sequences, associated with one or more of the disclosed polynucleotide sequences can also be obtained using the disclosed polynucleotide sequence provided herein. In one embodiment, such sequences are obtained by incubating polynucleotide molecules of the present invention with members of genomic libraries and recovering clones that hybridize to such polynucleotide molecules thereof. In a second embodiment, methods of "chromosome walking" or inverse PCR may be used to obtain such sequences (Frohman et al., Proc. Natl. Acad. Sci. (U.S.A.), 85:8998–9002, 1988; Ohara et al., Proc. Natl. Acad. Sci. (U.S.A.), 86:5673–5677, 1989; Pang et al., Biotechniques, 22:1046–1048, 1977; Huang et al., Methods Mol. Biol., 69:89–96, 1997; Huang et al., Method Mol. Biol., 67:287–294, 1997; Benkel et al., Genet. Anal., 13:123–127, 1996; Hartl et al., Methods Mol. Biol., 58:293–301, 1996). The phrase "chromosome walking" means a process of extending a genetic map by successive hybridization steps.

Another subset of the polynucleotide molecules of the present invention includes polynucleotide molecules that are markers. The markers can be used in a number of conventional ways in the field of molecular genetics. Such markers include polynucleotide molecules homologous or complementary to SEQ ID NO: 3, a nucleotide sequence having at least 80% identity to SEQ ID NO: 3, SEQ ID NO: 5, a nucleotide sequence having at least 80% identity to SEQ ID NO: 5, SEQ ID NO: 7, a nucleotide sequence having at least 80% identity to SEQ ID NO: 7, SEQ ID NO: 9, a nucleotide sequence having at least 80% identity to SEQ ID NO: 9, SEQ ID NO: 11, a nucleotide sequence having at least 80% identity to SEQ ID NO: 11, SEQ ID NO: 13, nucleotide sequences having at least 80% identity to f SEQ ID NO: 13, SEQ ID NO: 15, a nucleotide sequence having at least 87% identity to SEQ ID NO: 15, SEQ ID NO: 17, a nucleotide sequence having at least 87% identity to SEQ ID NO: 17, SEQ ID NO: 19, a nucleotide sequence having at least 91% identity to SEQ ID NO: 19, SEQ ID NO: 21, a nucleotide sequence having at least 91% identity to SEQ ID NO: 21, SEQ ID NO: 23, and a nucleotide sequence having at least 90% identity to SEQ ID NO: 23, and fragments thereof that can act as markers and other polynucleotide molecules of the present invention that can act as markers.

It is understood that one or more of the polynucleotide molecules of the present invention may be used as molecular markers. It is also understood that one or more of the protein molecules of the present invention may be used as molecular markers.

In an aspect of the present invention, one or more of the nucleic molecules of the present invention are used to determine the level of expression (i.e., the concentration of mRNA in a sample, etc.) in a plant (preferably canola, corn, Brassica campestris, oilseed rape, rapeseed, soybean, crambe, mustard, castor bean, peanut, sesame, cottonseed, linseed, safflower, oil palm, flax, or sunflower) or pattern (i.e., the kinetics of expression, rate of decomposition, stability profile, etc.) of the expression of a protein encoded in part or whole by one or more of the polynucleotide molecule of the present invention. A number of methods can be used to compare the expression between two or more samples of cells or tissue. These methods include hybridization assays, such as northerns, RNAse protection assays, and in situ hybridization. Alternatively, the methods include PCR-type assays. In a preferred method, the expression response is compared by hybridizing polynucleotides from the two or more samples to an array of polynucleotides. The array contains a plurality of suspected sequences known or suspected of being present in the cells or tissue of the samples.

Antibodies

One aspect of the present invention concerns antibodies, single-chain antigen binding molecules, or other proteins that specifically bind to one or more of the protein or peptide molecules of the present invention and their homologs, fusions, or fragments. In a particularly preferred embodiment, the antibody specifically binds to a polypeptide comprising a polypeptide sequence set forth in SEQ ID NO: 4, 6, 8, 10, 12, 16, 18, 20, 22, or 24, or fragments thereof. Antibodies of the present invention may be used to quantitatively or qualitatively detect the protein or peptide molecules of the present invention, or to detect post translational modifications of the proteins. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials that describe specific conditions and procedures for the construction, manipulation, and isolation of antibodies (see, for example, Harlow and Lane, In: Antibodies: A Laboratory Manual, Cold Spring Harbor Press, Cold Spring Harbor, N.Y., 1988).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope, or an enzyme).

The ability to produce antibodies that bind the protein or peptide molecules of the present invention permits the identification of mimetic compounds derived from those molecules. These mimetic compounds may contain a fragment of the protein or peptide or merely a structurally similar region and nonetheless exhibits an ability to specifically bind to antibodies directed against that compound. Having now generally described the present invention, the same will be more readily understood through reference to the following examples that are provided by way of illustration, and are not intended to be limiting of the present invention, unless specified.

EXAMPLES

Example 1

This example sets forth the isolation of HPPD DNA coding region sequences. Using the BlastN protocol (Altschul et al., *J. Mol. Biol.*, 403–410, 1990; National Center Biotechnology Information), the HPPD DNA sequences from *Synechocystis* sp. PCC6803 (SEQ ID NO: 1), and *Arabidopsis thaliana* (SEQ ID NO: 2) were used as search queries against bacterial and plant polynucleotide databases. Candidate gene sequences with an E-value score of $1e^{-8}$ or lower were obtained from a cotton 'seed coat' cDNA library, a cotton leaf cDNA library, a *Brassica napus* silique cDNA library (as used herein, a silique is a slender elongated two-valved dehiscent many-seeded fruit capsule that is characteristic of the mustard family, which opens by sutures at either margin, and has two parietal placentas), a soybean seed cDNA library, a tomato cDNA library, a *Bacillus thuringiensis* (Bt) genomic DNA library, and a *Sphingomonas elodea* genomic DNA library.

The cotton 'seed coat' cDNA library was constructed from seed coats isolated from cotton bolls 15–16 days post anthesis. No attempt was made to separate the fiber from the coat tissue. The cotton leaf cDNA library was made from leaf tissue isolated from the eighth cotton node from plants at full flower 2 months after planting. The *Brassica napus* cDNA library was made from silique tissue isolated 40 days after pollination. The soybean seed cDNA library was made from developing embryos isolated 16–18 days after flowering. The tomato flower cDNA library was made from tissue isolated from flowering tomato plants.

The plant cDNA libraries and bacterial genomic DNA libraries were constructed using isolated mRNA or total genomic DNA, respectively, by methods well known in the art (Sambrook et al., 2001). The plant cDNA library clones were sequenced to yield full-length or partial 'expressed sequenced tags' (ESTs). Where applicable, bacterial genomic DNA sequences were electronically and manually assembled into longer sequences ('contigs'). Design of polymerase chain reaction (PCR) polynucleotide primer molecules for isolating polynucleotide sequences of the present invention was based on the polynucleotide sequence information provided in the sequence listing for each of the respective polynucleotides described below. Reaction conditions were determined as described in the art (PCR Strategies, Innis et al., 1995; PCR Protocols, Innis et al, 1990). All reagents for isolating polynucleotide molecules of the present invention were obtained from Gibco BRL Life Technologies, Gaithersburg, Md.

Using the GCG Wisconsin Package® (Accelrys Inc., San Diego, Calif.) a large DNA segment of 1686 nucleotides (SEQ ID NO: 3) that contained several putative HPPD open reading frames (ORF) was identified from a Bt genomic library constructed from Bt strain EG10650. Bt Strain EG10650 is a derivative of Bt strain EG10368 (U.S. Pat. Nos. 5,759,538 and 5,962,264, herein incorporated by reference) that is deficient in neutral and alkaline protease activities and contains only one known extrachromosomal plasmid element of 7.5 kb. This nucleotide sequence (SEQ ID NO: 3) contained 4 methionine-encoding ATG potential start codons located within 78 nucleotides of each other. The potential start codons encoding methionine (Met) were located at polynucleotide positions 232–234 (Met 1), 274–276 (Met 14), 286–288 (Met 19), and 307–309 (Met 26). The largest ORF identified (SEQ ID NO: 5), starting at polynucleotide position 232–234 (Met 1), was determined to encode a protein of 385 amino acids (SEQ ID NOs: 4 and 6). An open reading frame starting at Met-14 (SEQ ID NO: 7), encoding a polypeptide of 372 amino acids (SEQ ID NO: 8), another starting at Met-19 (SEQ ID NO: 9), encoding a polypeptide of 367 amino acids (SEQ ID NO: 10), and another starting at Met-26 (SEQ ID NO: 11), encoding a polypeptide of 360 amino acids (SEQ ID NO: 12) were identified in this genomic region. The ORF encoding SEQ ID NO: 7 was identified with the aid of the GeneMark gene recognition program (Borodovsky et al., *Computers and Chemistry*, 17(19):123–133, 1993), as containing the likely initiator methionine in the native Bt strain.

Primers SEQ ID NOs: 28 and 30, were designed to amplify, by PCR, the Met 14 Bt HPPD sequence (SEQ ID NO: 7, Bt.Met14.HPPD). The SEQ ID NO: 28 primer was designed to add a NcoI site to the resulting PCR product by the addition of a GCG codon 3' to the native ATG start codon, causing the addition of an alanine following the initiator methionine of the encoded polypeptide. The SEQ ID NO: 30 primer was modified to replace the TAA stop codon with a TGA stop codon. The SEQ ID NO: 30 primer was further designed to contain an XhoI restriction site by addition of CTCGAG 3' to the TGA stop codon and then reverse-complemented to make the primer. Primer SEQ ID NO: 29, also adding a NcoI site, and primer SEQ ID NO: 30 were used to amplify, by PCR' the Bt.Met26.HPPD encoding sequence (SEQ ID NO: 11). The sequence of all polynucleotide primer molecules of the present invention are listed in FIG. 2.

Figure 3:
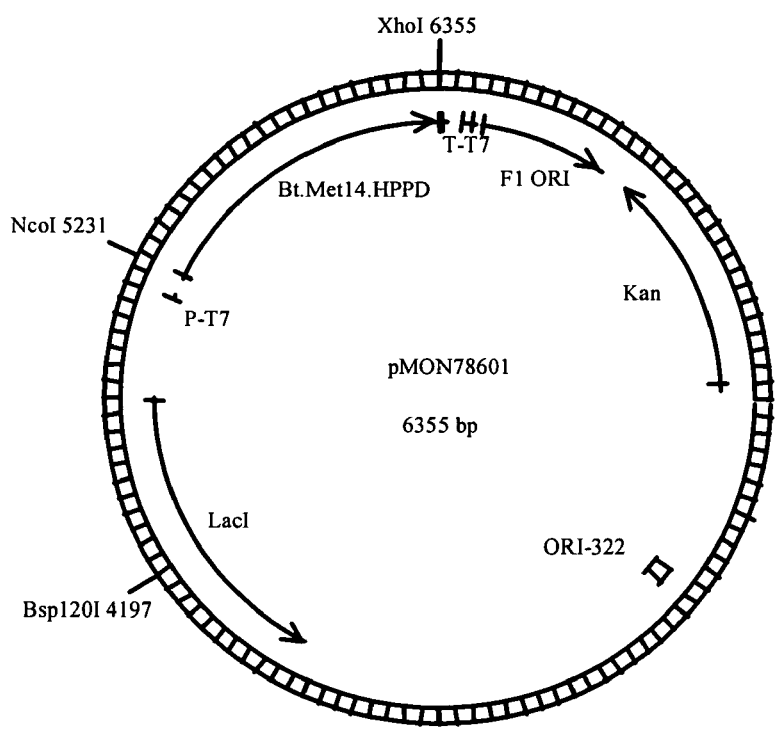
FIG. 3 illustrates the plasmid map of pMON78601.
Figure 4:
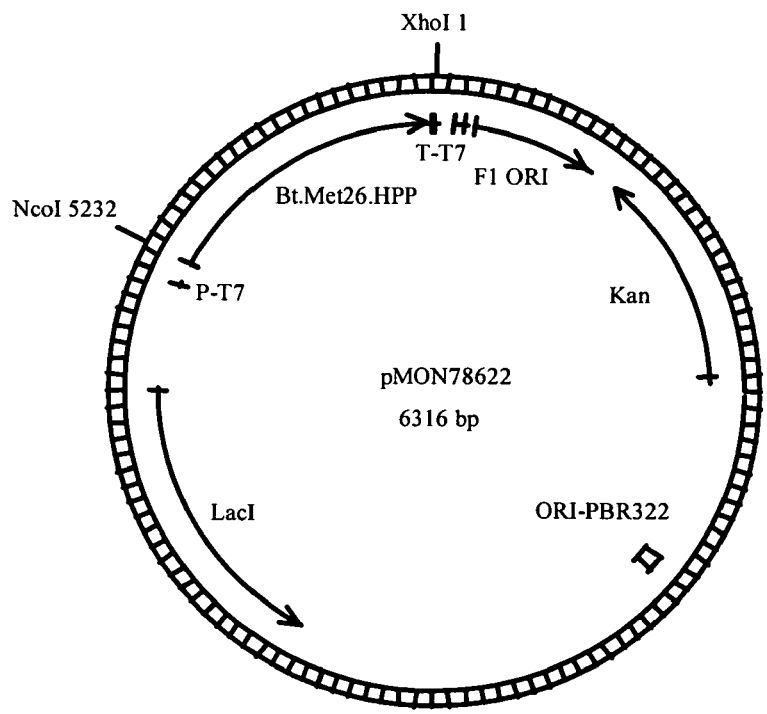
FIG. 4 illustrates the plasmid map of pMON78622.

The PCR was performed using genomic DNA isolated from Bt strain EG10650 and the SEQ ID NOs: 28 and 30 primer pairs, and separately, the SEQ ID NOs: 29 and 30 primer pairs, using Expand Hi-Fidelity DNA polymerase (Boehringer-Mannheim Corp., Indianapolis, Ind.), and the reagents and directions provided by the manufacturer. The PCR conditions were as follows: 95° C. for 2 minutes, followed by 25 cycles of 30 seconds at 94° C., 45 seconds at 45° C., 90 seconds at 72° C., and finally 5 minutes at 72° C. Polynucleotide products of approximately 1.2 kb were obtained, and after enzymatic digestion with NcoI/XhoI, were cloned into a similarly digested pET24d plasmid (Novagen, Madison, Wis.). The pET24d plasmid is a T7 promoter based *E. coli* expression vector. The resulting plasmids containing the Bt HPPD sequences were named pMON78601 (FIG. 3) and pMON78622 (FIG. 4). The polynucleotide sequences of the inserts in these plasmids were confirmed as SEQ ID NOs: 11 and 44, respectively. HPPD activity was measured qualitatively by colorimetric reaction or quantitatively by RP-HPLC analysis of HPPD reaction products as described in Example 2.

Using the tBLASTn protocol, two cotton HPPD genes were identified from the cotton seed and leaf EST libraries, which contained full-length coding sequences. The full-length sequences of these clones are shown in SEQ ID NOs: 15 and 17. Analysis of the deduced amino acid sequences identified two ORFs encoding proteins of 436 amino acids each (SEQ ID NOs: 16 and 18). Cotton HPPD SEQ ID NOs: 15 and 17 were 98.3% identical to each other at the DNA level. Their respective predicted amino acid sequences, SEQ ID NOs: 16 and 18 were 98.6% identical to each other. The two cotton HPPD DNA sequences were designated as cotton Gh1.HPPD (SEQ ID NO: 15) and cotton Gh2.HPPD (SEQ ID NO: 17). Analysis of the deduced amino acid sequences using the ChloroP program (Emanuelson et al., *Protein Science*, 8:978–984, 1999) indicated that the first 23 amino acids in both sequences are likely chloroplast transit peptides (CTP). Such CTPs have not been noted in other plant HPPDs. In fact, the *Arabidopsis* and carrot genes, which are targeted to the cytoplasm, do not contain a CTP (Garcia et al., *Biochem. J.*, 325:761–769, 1997; Garcia et al., *Plant Phys.*, 119:1507–1516, 1999).

The coding regions for cotton Gh1.HPPD (SEQ ID NO: 15) and Gh2.HPPD (SEQ ID NO: 17) were amplified using the identified cotton EST clones as the template DNA source. For expression in *E. coli*, PCR was performed using SEQ ID NOs: 31 and 32 as primers, using Expand Hi-Fidelity DNA polymerase (Boehringer-Mannheim Corp., Indianapolis, Ind.), and the reagents and directions provided by the manufacturer. The SEQ ID NO: 31 primer was designed to add a NcoI restriction site, an ATG start side, and a GCC codon for alanine, followed by codon 24 of either sequence (i.e., following the predicted CTP cleavage site). The SEQ ID NO: 32 primer was designed to put an XhoI restriction site immediately following the TGA stop codon at the 3' end of the gene. The PCR conditions were as follows: 95° C. for 2 minutes, followed by 25 cycles of 30 seconds at 94° C., 45 seconds at 45° C., 90 seconds at 72° C., and finally 5 minutes at 72° C. The resulting products of the reaction were purified and isolated using standard methodologies well known in the art and cloned into a NcoI and XhoI restriction enzyme digested pET24d plasmid for transformation into *E. coli*. The resulting plasmids containing the mature cotton HPPD sequences were named pMON78602 (FIG. 5) and pMON78603 (FIG. 6). HPPD activity was measured as described in Example 2.

Figure 7:
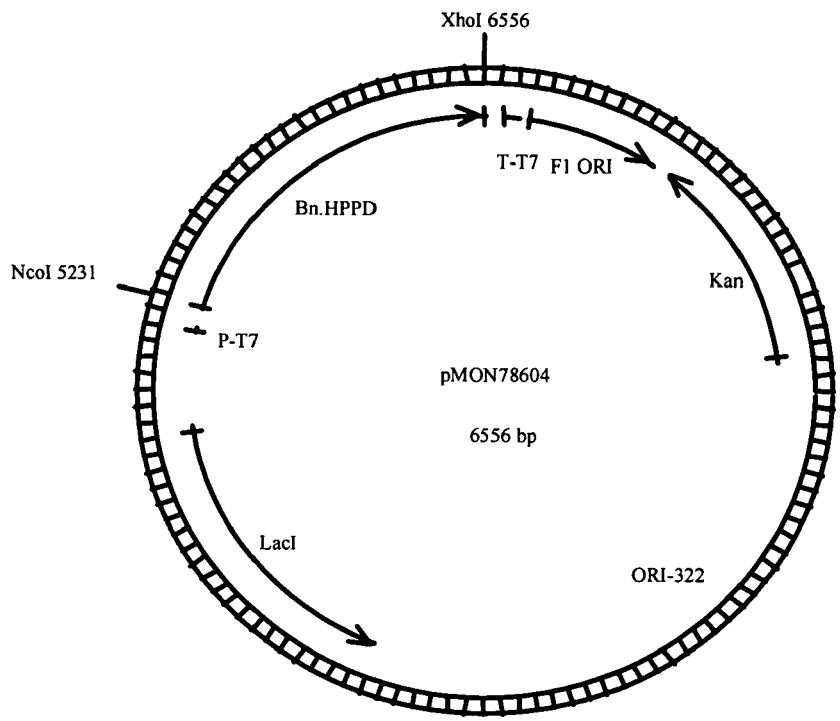
FIG. 7 illustrates the plasmid map of pMON78604.

Using the tBLASTn protocol, a *Brassica* HPPD gene was also identified from a cDNA library. The full-length sequence of this clone is shown in SEQ ID NO: 19. Analysis of the deduced amino acid sequence shows an ORF encoding a protein of 440 amino acids (SEQ ID NO: 20). Analysis of the predicted amino acid sequence (SEQ ID NO: 20) from the *Brassica* HPPD using the ChloroP program did not detect an N-terminal CTP sequence on the protein. The full-length coding region for the *Brassica* HPPD was amplified by PCR using *Brassica* cDNA and SEQ ID NOs: 33 and 34 as primers, and using Expand Hi-Fidelity DNA polymerase (Boehringer-Mannheim Corp., Indianapolis, Ind.), and the reagents and directions provided by the manufacturer. The PCR conditions were as follows: 95° C. for 2 minutes, followed by 25 cycles of 30 seconds at 94° C., 45 seconds at 45° C., 90 seconds at 72° C., and finally 5 minutes at 72° C. The resulting products of the reaction were purified and isolated using standard methodologies well known in the art, restriction enzyme digested with NcoI and XhoI, and subsequently cloned into the similarly digested plasmid, pET24d. The resulting plasmid was named pMON78604 (FIG. 7). HPPD activity was measured as described in Example 2.

Figure 8:
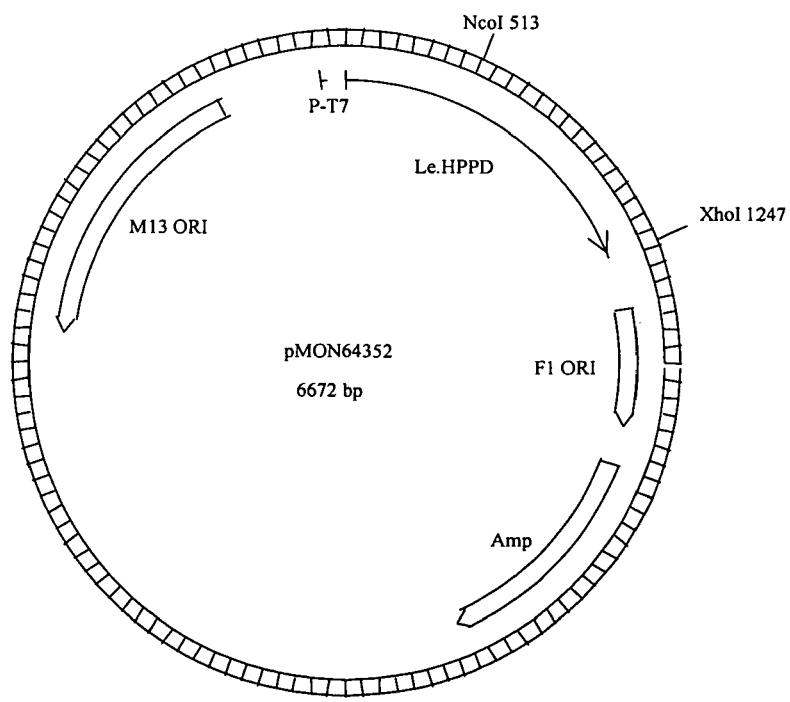
FIG. 8 illustrates the plasmid map of pMON64352.
Figure 9:
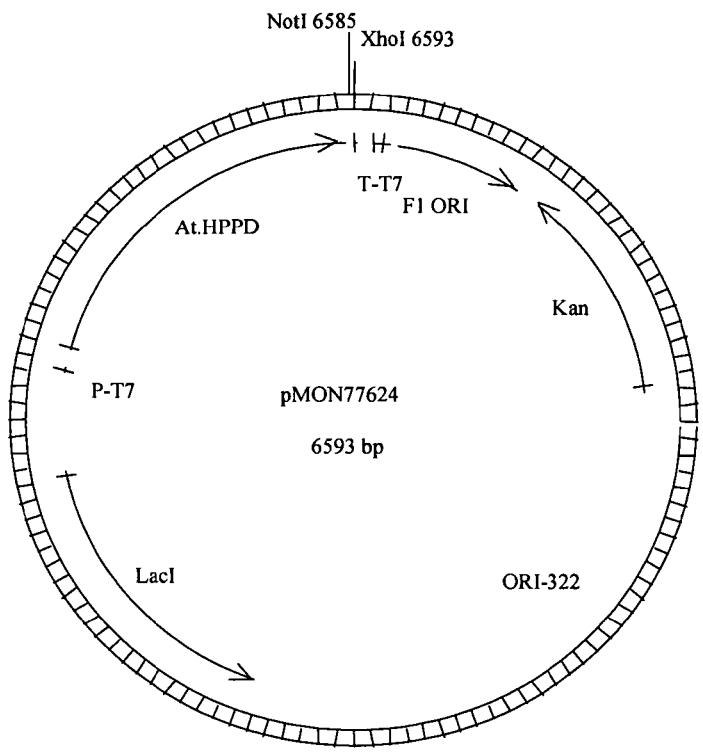
FIG. 9 illustrates the plasmid map of pMON77624.

Using the tBLASTn protocol, a tomato HPPD gene was also identified from a cDNA library. The full-length sequence of this clone is shown in SEQ ID NO: 21. Analysis of the deduced amino acid sequence shows an ORF encoding a protein of 437 amino acids (SEQ ID NO: 22). The initiator methionine codon is absent in this clone, although the predicted N-terminal sequence was determined to contain a CTP when analyzed using the ChloroP program. The coding region for the mature tomato HPPD (i.e., following the predicted CTP cleavage site) was amplified by PCR using tomato cDNA, and SEQ ID NOs: 35 and 36 as primers and the conditions set forth in Table 2. The resulting fragments were digested with NdeI and XhoI, and subsequently cloned into the similarly NdeI/XhoI digested pET24a plasmid resulting in plasmid pMON64352 (FIG. 8). Plasmid pMON64352 was transformed into an *E. coli* expression host Tuner (DE3) (Novagen, Wis.) and HGA activity as described in Example 2.

TABLE 2

| PCR conditions used for isolation of the Tomato HPPD gene | | |
|---|---|---|
| Step | Temp/Degrees Centigrade | Time |
| 1 | 94 | 2 minutes |
| 2 | 94 | 15 seconds |
| 3 | 50 | 30 seconds |
| 4 | 72 | 1 minute |
| 5 | Go to step 2 nine times (total of 10 cycles of steps 2–4) | |
| 6 | 94 | 15 seconds |
| 7 | 50 | 30 seconds |
| 8 | 72 | 1 minute + 5 seconds/cycle |
| 9 | Go to step 6 nineteen times (for a total of 20 cycles of steps 6–8) | |
| 10 | 72 | 7 minutes |
| 11 | 4 | Hold |

Using the tBLASTn protocol, a *Sphingomonas* HPPD gene was also identified from a compilation of sequence contigs derived from a *Sphingomonas* genomic library. The less than full length sequence of this HPPD gene is shown in SEQ ID NO: 23 (Sph.HPPD). Analysis of the deduced polypeptide sequence shows an open-reading frame encoding a protein of 337 amino acids (SEQ ID NO: 24).

Example 2

This example sets forth the analysis of HPPD activity in cell free extracts of transformed *E. coli* cells. Polynucleotide sequences encoding HPPD enzymes from *Arabidopsis* (SEQ ID NO: 2), Bt (SEQ ID NO: 7), *Brassica* (SEQ ID NO: 19), cotton (SEQ ID NOs. 15 and 17), *Synechocystis* (SEQ ID NO: 1), and tomato (SEQ ID NO: 21), were expressed in *E. coli* and their resulting HPPD enzyme activity measured qualitatively by colorimetric reaction or analytically by reverse phase-high performance liquid chromatography (RP-HPLC). In the case of SEQ ID NOs: 15, 17, and 21, the 5' sequences encoding the CTPs were removed as described in Example 1.

Enzymatically active HPPDs, isolated from a number of plant and bacterial sources, have been shown to cause a brown coloration to the broth when expressed in heterologous expression systems such as *E. coli*. The brown coloration is due to a melanin-related pigment that results from the accumulation and cellular excretion of homogentisic acid (HGA), and its subsequent non-enzymatic oxidation and polymerization (Denoya et al., *J. Bacteriol.*, 176:5312–5319, 1994).

To determine HPPD activity colormetrically, *E. coli* cell free extracts of select HPPD constructs were prepared by transformation of *E. coli* Tuner (DE3) cells with a pET-expression plasmid containing a recombinant HPPD using standard heat shock transformation procedures as described by Sambrook et al., 2001. The transformed cells were then grown at 37° C. on LB agar media containing 50 μg/mL kanamycin. Single colonies were chosen to inoculate an overnight LB preculture. Three mL of this preculture were used to inoculate a 125 mL LB culture with 50 µg/mL kanamycin. This culture was incubated at 37° C. and shaken at 225 revolutions per minute (rpm) until an Optical Density $(OD)_{600}$ of 0.6 to 0.8 was obtained. Subsequently, the culture was induced with 0.5 mM isopropyl-β-D-thiogalactoside (IPTG) (final concentration) and the incubation was continued for 4 hours at 25° C. Induced cells were harvested by centrifugation (20,000 X g) for 10 minutes and the pellet was resuspended in 6 mL of buffer A (50 mM $KP_i$ at pH 7.4, 1 mM DTT, 100 µm Pefablock (Boehringer-Mannheim, Germany), 1 µM Leupeptin (Boehringer-Mannheim, Germany), 0.1 µM Aprotinin (Boehringer-Mannheim), 50 mM NaCl and 1 mM $MgCl_2$). All other reagents were from Sigma-Aldrich Chemical Company, St. Louis, Mo.). Cells were lysed in the presence of 50 units of DNAase by two passages through a French Press at a pressure of 130 MPa. The extracts were then centrifuged at 100,000 X g for 1 hour to yield a cell-free extract.

After growth and induction, followed by 24 hr. incubation at 30° C., culture broths containing HPPD expressing cells transformed with single gene constructs of *Arabidopsis thaliana* (SEQ ID NO: 2), Bt (SEQ ID NO: 7), Brassica (SEQ ID NO: 19), cotton (SEQ ID NOs: 15 and 17), *Synechocystis* (SEQ ID NO: 1), or tomato (SEQ ID NO: 21) produced a characteristic brown coloration with a broad absorption maximum at 400 nM showing that the HPPD genes encoded active HPPD enzymes. See Table 3.

TABLE 3

The mean absorbance at 400 nanometers of culture supernatants of *E. coli* expressing recombinant HPPD

| HPPD Source | Plasmid | N | Mean | Std Dev | Std Err Mean | Significance |
|---|---|---|---|---|---|---|
| Empty vector | pET21d | 6 | 0.00 | 0.04 | 0.02 | |
| *Arabidopsis* | pMON77624 | 5 | 0.63 | 0.01 | 0.00 | A |
| *Brassica* | pMON78604 | 5 | 0.05 | 0.02 | 0.01 | A |
| *Bt* (Met-14) | pMON78601 | 5 | 0.57 | 0.03 | 0.01 | A |
| Cotton Gh1.HPPD | pMON78602 | 5 | 0.57 | 0.01 | 0.00 | A |
| Cotton Gh2.HPPD | pMON78603 | 5 | 0.58 | 0.01 | 0.00 | A |
| *Synechocystis* | pMON77612 | 5 | 0.39 | 0.04 | 0.02 | A |
| Tomato | pMON64352 | 5 | 0.56 | 0.02 | 0.01 | A |

Comparisons with a control (empty vector) using Dunnett's Method, Alpha = 0.05.
Means followed by a significance of "A" are significantly different from the pET empty vector control.
A mean of 0.00 results from rounding error.
N denotes the number of replicate assays used to calculate mean absorbance.
The mean optical density for each HPPD source was observed at an absorbance of 400 nm.

A quantitative method of determining HPPD enzyme activity is based on spectrophotometric analysis of HPLC purified HPPD metabolites, in particular HGA, according to a modified method as described (Secor, J., *Plant Physiol.*, 106:1429–1433, 1994; Garcia et al., *Plant Physiol.*, 119: 1507–1516, 1999). The assay was performed in 50 mM potassium phosphate, pH 7.4, containing 50 mM ascorbic acid, 5000 units of catalase, 100 µM ferrous sulfate, 0.1 to 0.5 mM 4-hydoxyphenylpyruvic acid (HPPA), and an empirically determined volume of cell free bacterial extract containing recombinant expressed HPPD. The final assay volume was 200 µL. A HPPA stock solution (2.5–10 mM) was freshly prepared in potassium phosphate buffer, pH 7.4, and allowed to equilibrate for 2 hours at room temperature prior to each assay. The HPPD reaction was initiated by addition of HPPA and incubated for 15 minutes at 30° C. The reaction was terminated by adding 20 µL of 70% (w/v) perchloric acid. Precipitated salt and proteins were removed by 5 minutes centrifugation in an Eppendorff desktop centrifuge at 14,000 rpm. The assay supernatant was filtered through a 0.22 µm PTFE syringe filter and used for HPLC analysis.

Quantification of HGA was performed by RP-HPLC analysis using a Hewlett Packard 1100 series HPLC with HP interface 35900E. HGA and HPPA were identified by comparison with pure standards (Aldrich-Sigma Chemical Company, Missouri). HGA was quantified by comparison with a HGA standard curve in the range of 0.5 to 1000 µM at 288 nm. Samples (90 µL) were loaded onto a Waters Pico Tag (C18, 4µ, 3.9×150 mm) column for separation (Waters Corporation, Milford, Mass.). Buffers A (0.1% (v/v) trifluoroacetic acid (TFA) in $H_2O$) and B (0.07% (v/v) TFA in 80% $CH_3CN$) were used at a flow rate of 1 mL/min to create linear gradients of 0 to 40% B from 0 min to 10 min, followed by an increase of buffer B from 40 to 100% in 1 min, and 100 to 0% B in 1 min, followed by 0% B for 3 minutes.

Protein concentrations were determined using the Bio-Rad Protein Assay (Bio-Rad Laboratories, Inc., Hercules, Calif.). Bovine serum albumin (BSA) was used as the protein standard. HPPD activity was calculated based on the amount of detectable homogentisic acid (HGA) in the assay supernatant. The results are shown in Table 4 below with specific activity expressed as nanomoles HGA produced minute$^{-1}$ milligram protein$^{-1}$. Data was analyzed using JMP statistical software (SAS Institute, Cary, N.C.). Data was first tested for homogeneity of variances using Levene's test and then the means were compared using the standard least squares method with planned contrasts. Any HPPD Source mean with a Prob>|t| of 0.05 or smaller is considered significantly different from the vector control.

TABLE 4

The specific activity of HPPD in cell free extracts of recombinant HPPDs expressed in *E. coli*

| HPPD Source | Plasmid | N | Mean Specific Activity | Std Dev | Std Err Mean | Significance |
|---|---|---|---|---|---|---|
| Vector control (Pet21d) | Empty vector | 10 | 0.00 | 0.00 | 0.00 | |
| *Arabidopsis* | pMON77624 | 3 | 570.28 | 51.40 | 29.68 | 3.00E−19 |
| *Brassica* | pMON78604 | 3 | 0.78 | 0.34 | 0.20 | 0.9629 |
| *Bt* (Met-14) | pMON78601 | 3 | 1429.49 | 54.10 | 31.24 | 3.00E−27 |
| Cotton Gh1.HPPD | pMON78602 | 2 | 116.65 | 38.56 | 27.27 | 7.40E−06 |

TABLE 4-continued

The specific activity of HPPD in cell free extracts of recombinant HPPDs expressed in E. coli

| HPPD Source | Plasmid | N | Mean Specific Activity | Std Dev | Std Err Mean | Significance |
|---|---|---|---|---|---|---|
| Synechocystis | pMON77612 | 2 | 10.97 | 0.92 | 0.65 | 0.5793 |
| Tomato | pMON64352 | 3 | 11.93 | 1.45 | 0.83 | 0.479 |

Variances not equal, Levene's method, P < 0.0001.
There is an effect due to treatment, SLS, P < 0.0001.
Means with a Prob > |t| value <0.05 are significantly different from the empty vector, Planned Contrasts.
N denotes the number of replicate assays used to calculate each specific activity.

Example 3

Figure 11:
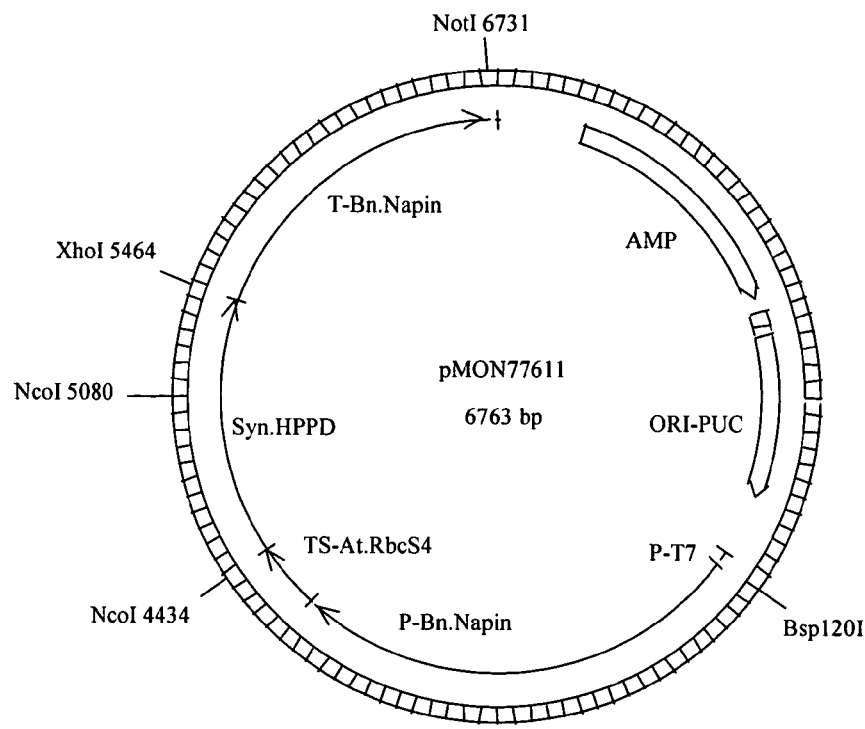
FIG. 11 illustrates the plasmid map of pMON77611.
Figure 12:
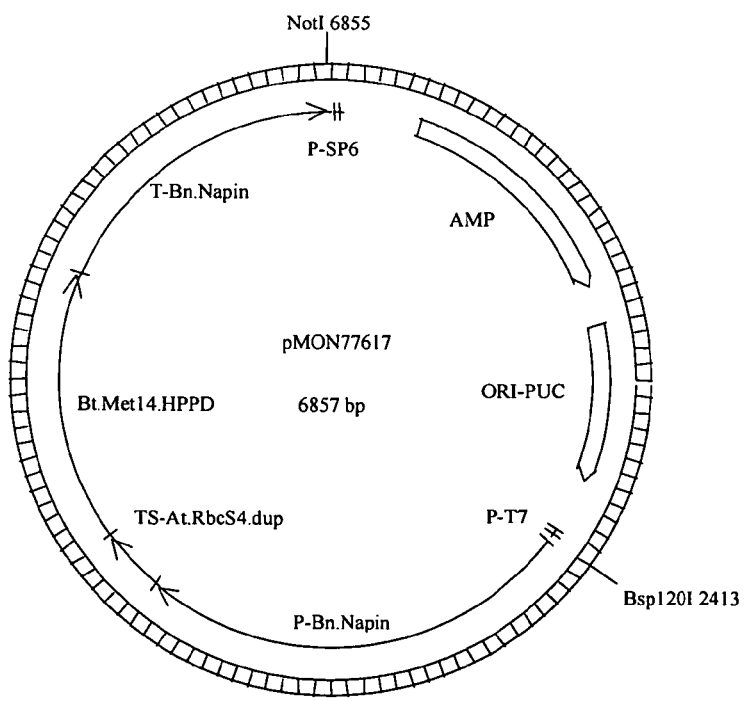
FIG. 12 illustrates the plasmid map of pMON77617.
Figure 13:
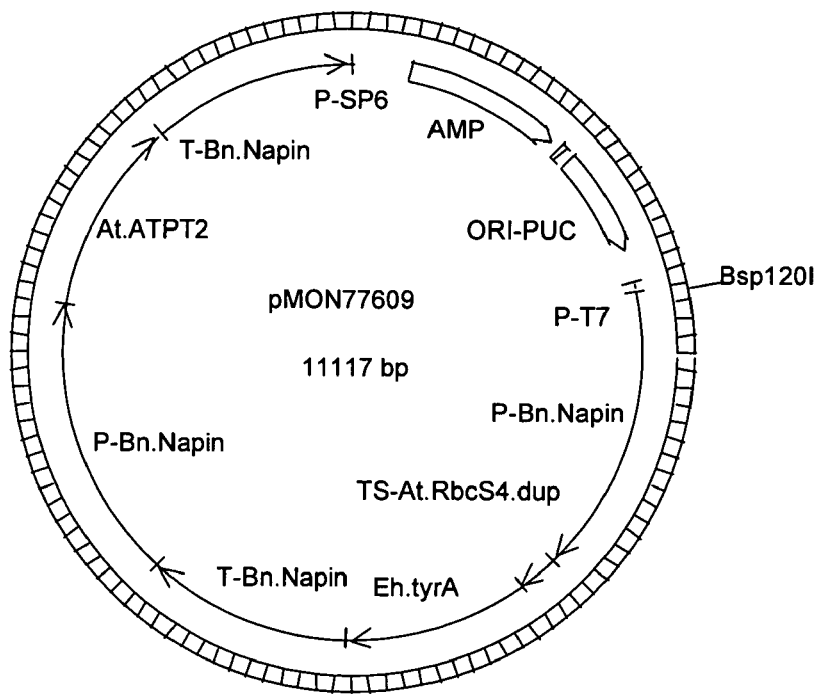
FIG. 13 illustrates the plasmid map of pMON77609.
Figure 14:
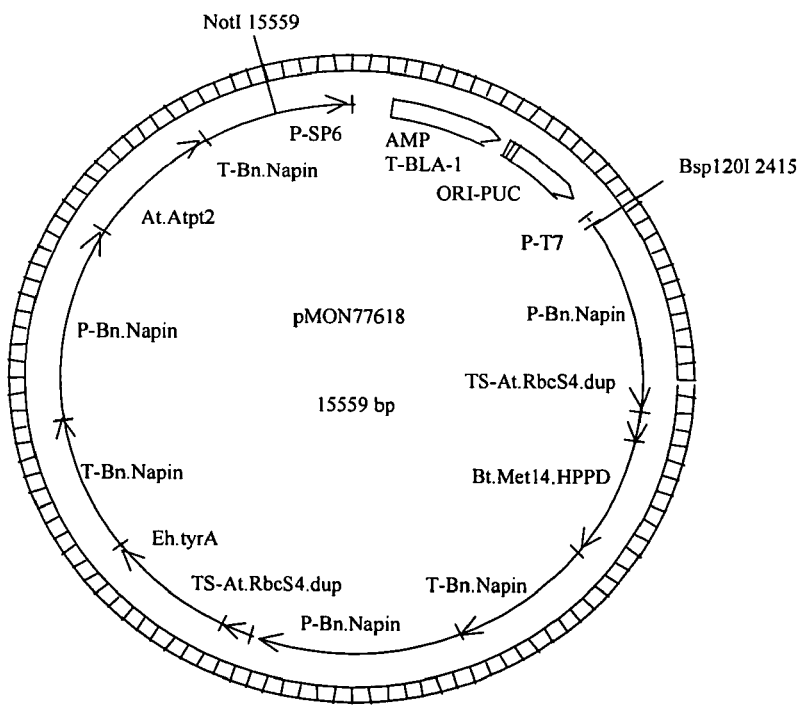
FIG. 14 illustrates the plasmid map of pMON77618.
Figure 15:
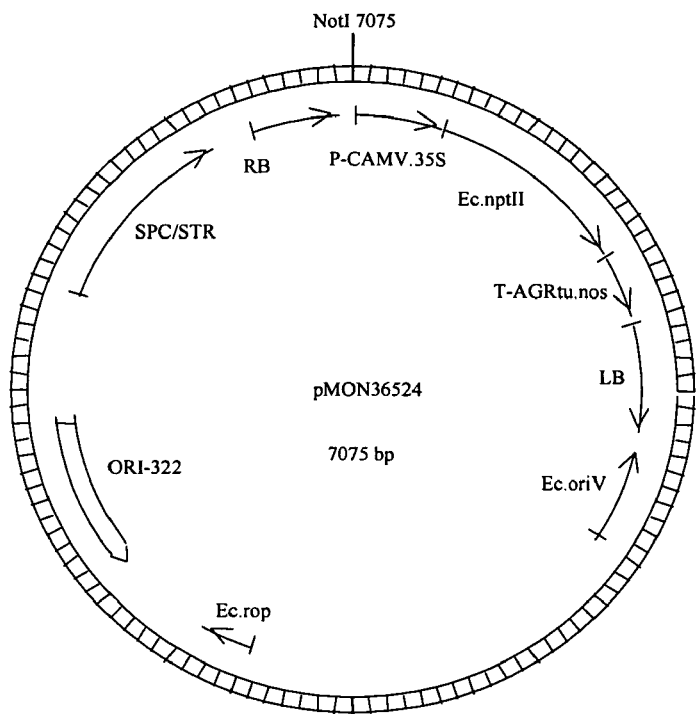
FIG. 15 illustrates the plasmid map of pMON36524.
Figure 16:
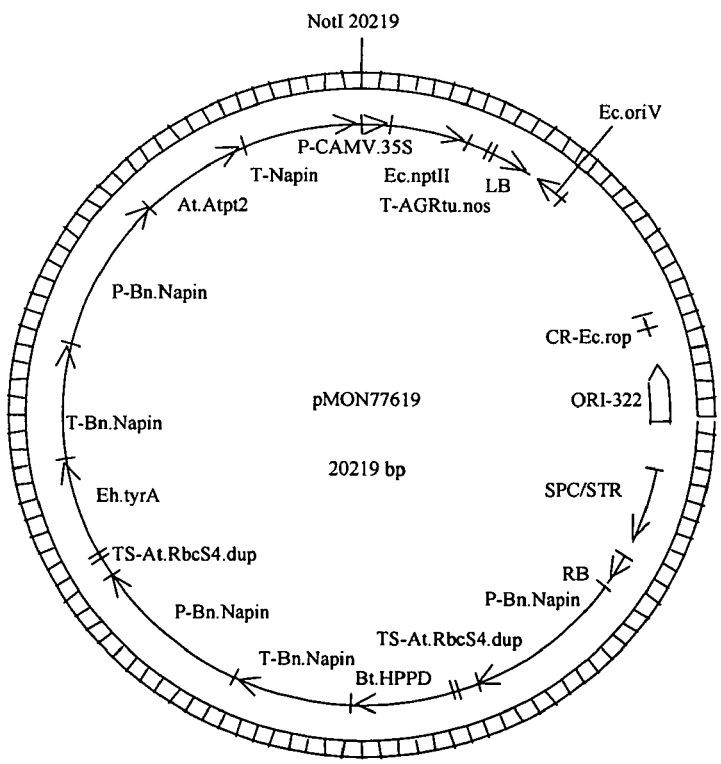
FIG. 16 illustrates the plasmid map of pMON77619.

This example sets forth the construction of plant transformation vectors containing tocopherol pathway genes in combination with HPPD genes to increase seed tocopherol levels. To test the in planta performance of HPPD sequences from *Arabidopsis thaliana, Bacillus thuringiensis, Gossypium hirsutum*, and *Synechocystis* sp. PCC6803, the aforementioned genes were cloned under the control of a napin promoter (U.S. Pat. No. 5,420,034, herein incorporated by reference) in a 3-gene vector containing an HPPD, a bifunctional prephenate dehydrogenase (Eh.tyrA) (SEQ ID NO: 25), and a homogentisate phytyltransferase (At.Atpt2) (SEQ ID NO: 26). The 3-gene vector containing the *Bacillus thuringiensis* HPPD (Bt.Met14.HPPD) (SEQ ID NO: 7) was generated as follows: pMON78601 (FIG. 3) was subjected to a double restriction enzyme digest with NcoI and XhoI, and the 1124 bp fragment containing the coding region of the Bt.HPPD-gene was subsequently gel-purified, using a Qiagen spin column kit and the manufacturers directions (Qiagen Inc., Valencia, Calif.). In parallel, a vector containing a napin promoter and a napin 3'-UTR flanked by a NotI restriction site and a Bsp120I restriction site (pMON77611) (FIG. 11) was digested with NcoI and XhoI, and the 5733 bp vector backbone containing a napin promoter, TS-At.RbcS4 (CTP2), and a napin 3'-UTR was gel purified using Qiagen spin columns. The purified fragments were ligated with Ligase (New England Biolabs, Beverly, Mass.), resulting in the formation of pMON77617 (FIG. 12). This vector contained the Bt.Met14.HPPD flanked by a napin promoter at the 5'-end, TS-At.Rbsc4, and by a napin 3'-UTR at the 3'-end. This expression cassette was excised by a restriction digest of pMON77617 using NotI and Bsp120I restriction enzymes. The 4442 bp fragment encoding the Bt.HPPD expression cassette was gel purified as described above. In parallel, pMON77609 (FIG. 13), a shuttle vector containing napin promoter driven expression cassettes for the *Erwinia herbicola* tyrA, and the *A. thaliana* HPT (At.Atpt2) was digested with a Bsp 120I restriction enzyme, dephosphorylated with calf intestinal alkaline phosphatase (Roche Applied Science, Indianapolis, Ind.), and gel purified using a Qiagen spin column kit. The purified dephosphorylated vector was ligated with the purified napin promoter driven HPPD expression cassette to form the triple gene shuttle vector pMON77618 (FIG. 14). The latter vector served as a source for the three napin promoter driven expression cassettes for Bt.Met14.HPPD, Eh.tyrA, and At.Atpt2, which were isolated from pMON77618 as a single 13144-bp fragment via a Bsp120I/NotI double restriction digest. The large fragment was gel purified as described, and ligated with NotI digested, dephosphorylated (as described) and gel purified pMON36524 (FIG. 15). The resulting plant binary vector containing the three napin promoter controlled expression constructs was designated pMON77619 (FIG. 16).

Figure 5:
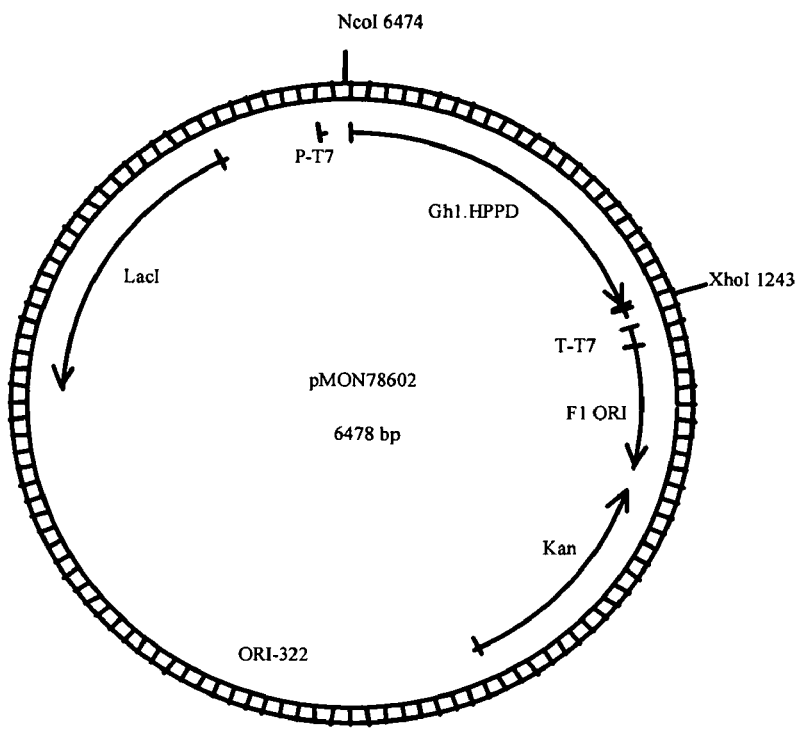
FIG. 5 illustrates the plasmid map of pMON78602.
Figure 6:
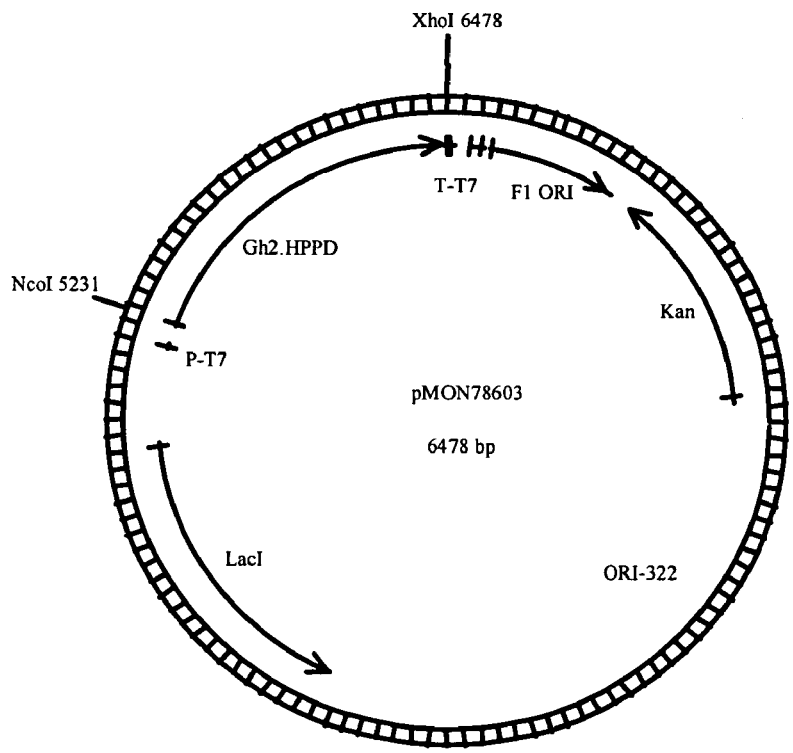
FIG. 6 illustrates the plasmid map of pMON78603.
Figure 17:
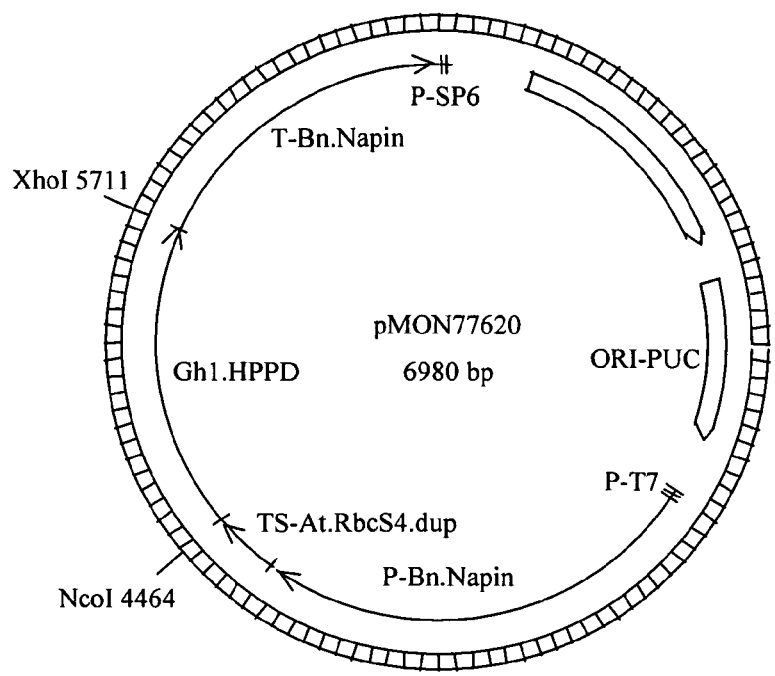
FIG. 17 illustrates the plasmid map of pMON77620.
Figure 18:
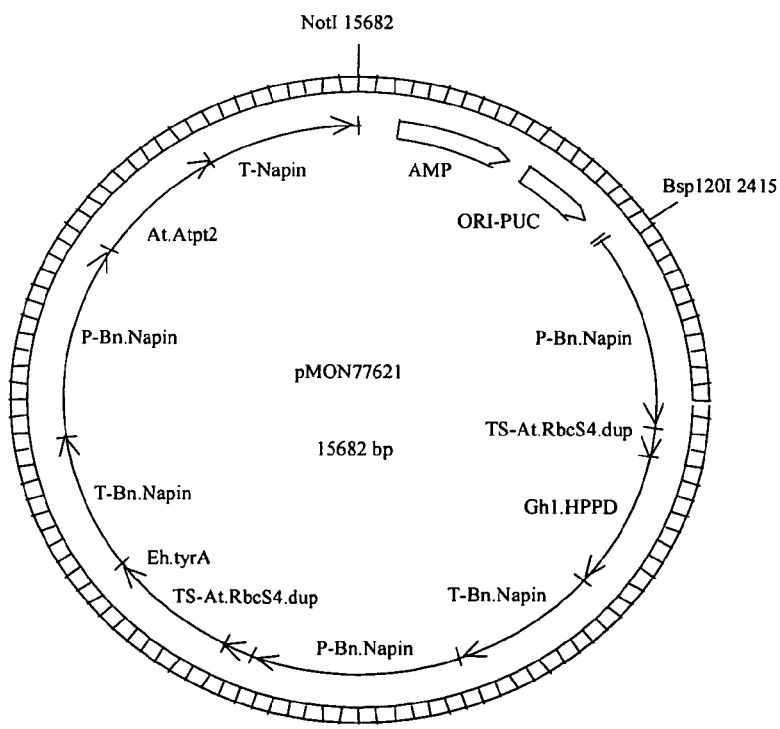
FIG. 18 illustrates the plasmid map of pMON77621.
Figure 19:
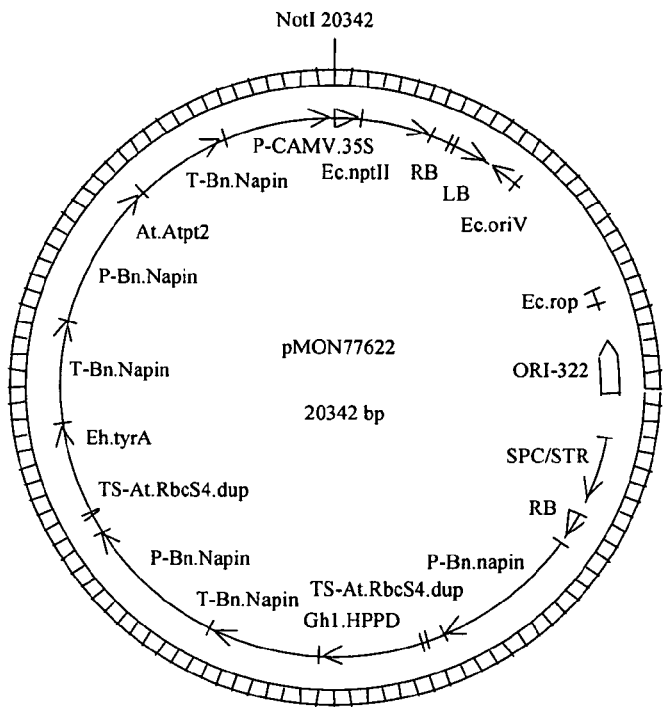
FIG. 19 illustrates the plasmid map of pMON77622.

Similarly, a triple gene vector containing a napin promoter driven cotton HPPD construct in addition to a napin promoter driven HPT and tyrA expression cassette was constructed as follows: the cotton HPPD (Gh1.HPPD) (SEQ ID NO: 15) was isolated by NcoI and XhoI restriction enzyme digestion of pMON78602 (FIG. 5). The 1247-bp fragment was gel purified using Qiagen spin columns, and ligated into the XhoI and NcoI restriction enzyme, digested, and gel purified backbone of plasmid, pMON77611 (FIG. 11). The resulting 6980-bp vector was designated pMON77620 (FIG. 17), where the coding region of mature Gh1.HPPD is connected to the TS-At.RbcS4 CTP and the napin promoter. The latter vector was digested with Bsp120I and NotI restriction enzymes and the resulting 4565-bp Gh1.HPPD-expression cassette gel purified as described, and ligated into a Bsp120I restriction enzyme digested, CIP treated, and gel purified pMON77609 (FIG. 13) vector backbone, resulting in the formation of pMON77621 (FIG. 18). The three expression cassettes for Gh1.HPPD, Eh.tyrA, and At.Atpt2 present in pMON77621 were released as a single 13267-bp-fragment by a Bsp120I and NotI double restriction enzyme digest, gel purified as described, and ligated into a NotI-digested, CIP treated, and gel purified pMON36524 (FIG. 13), resulting in the formation of pMON77622 (FIG. 19).

Figure 10:
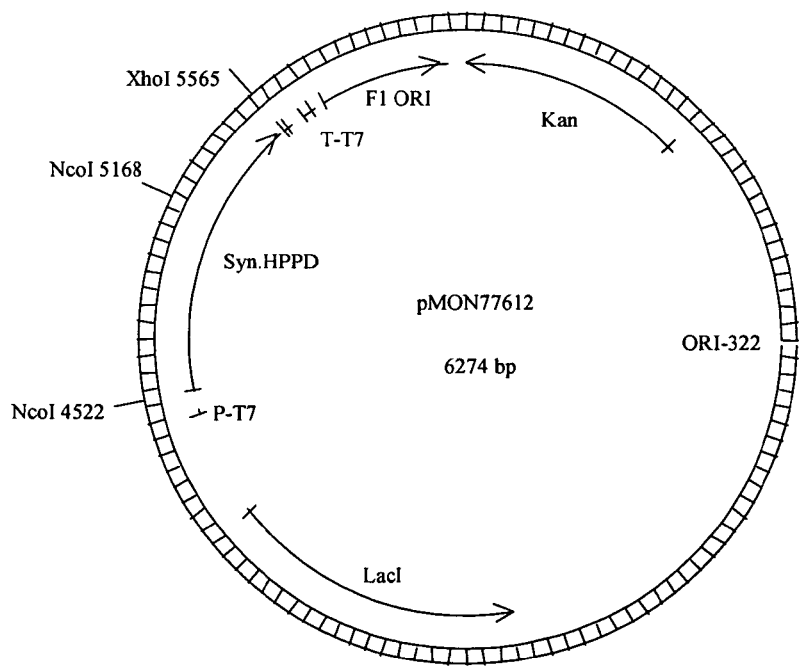
FIG. 10 illustrates the plasmid map of pMON77612.
Figure 20:
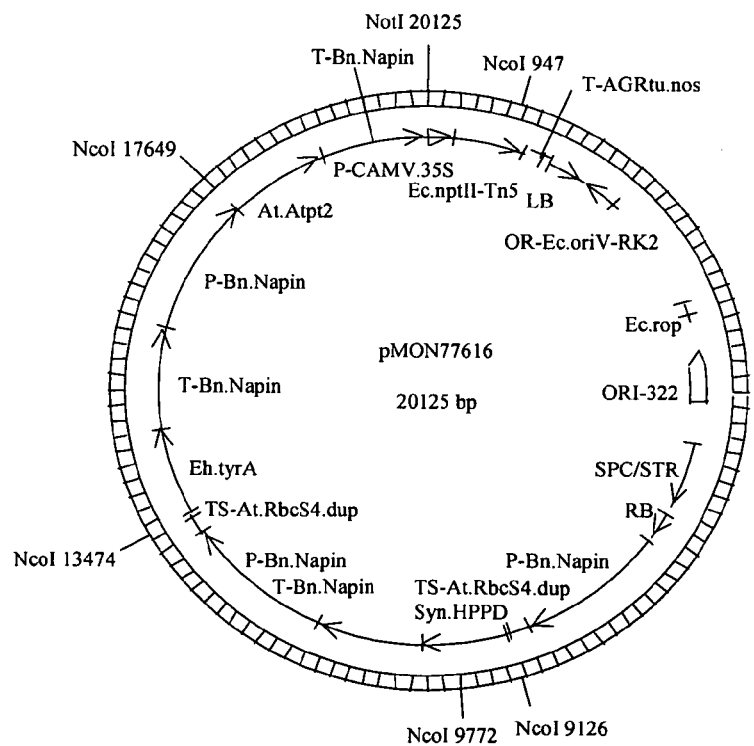
FIG. 20 illustrates the plasmid map of pMON77616.

Following the same procedures described for construction of the triple gene vectors pMON77622 and pMON77619, a triple gene vector containing a napin promoter driven expression cassette for the *Synechocystis* HPPD (SEQ ID NO: 1), the *Erwinia herbicola* tyrA, and the *Arabidopsis thaliana* At.Atpt2 was constructed using pMON77612 (FIG. 10) as the gene source. The resulting binary vector was designated pMON77616 (FIG. 20).

Figure 21:
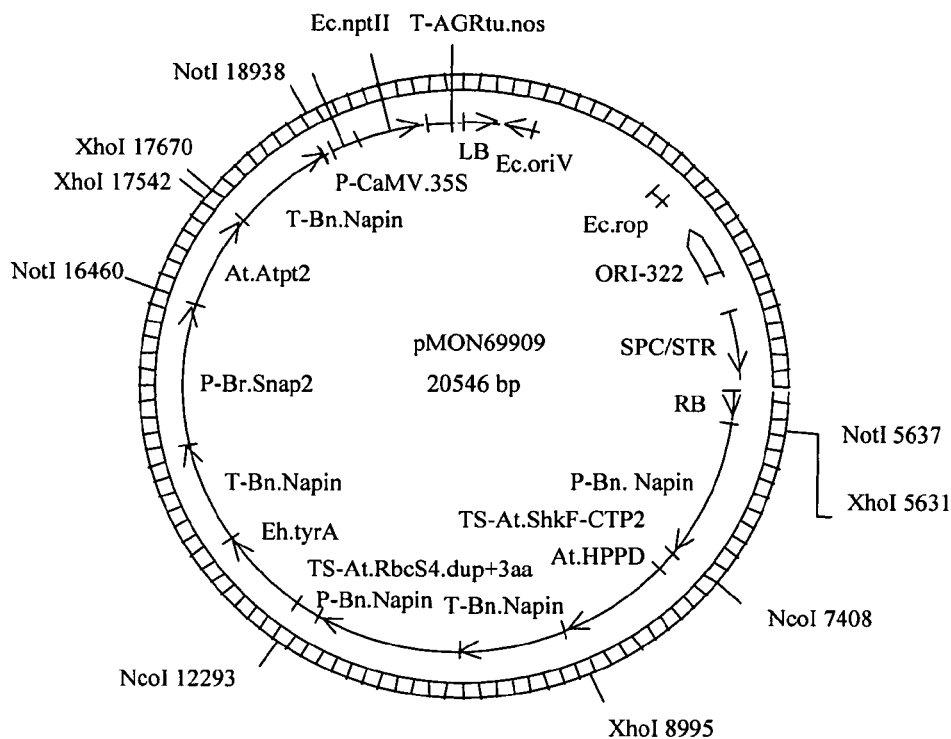
FIG. 21 illustrates the plasmid map of pMON69909.

A triple gene binary vector containing a napin promoter driven expression cassette of the *Arabidopsis thaliana* HPPD (SEQ ID NO: 2), plus the napin promoter driven expression cassettes for the *Erwinia herbicola* tyrA, and the *Arabidopsis thaliana* At.Atpt2 (pMON69909, FIG. 21), and a double gene vector containing a napin promoter driven expression cassette for Eh.tyrA, and At.Atpt2 (pMON69907, FIG. 15) were used as control vectors.

Figure 22:
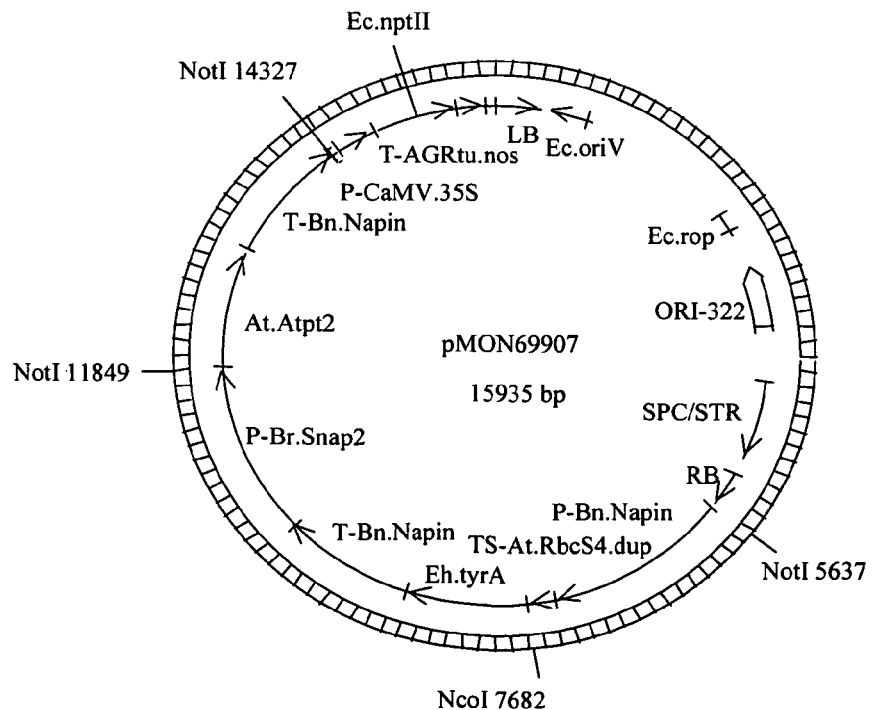
FIG. 22 illustrates the plasmid map of pMON69907.
Figure 23:
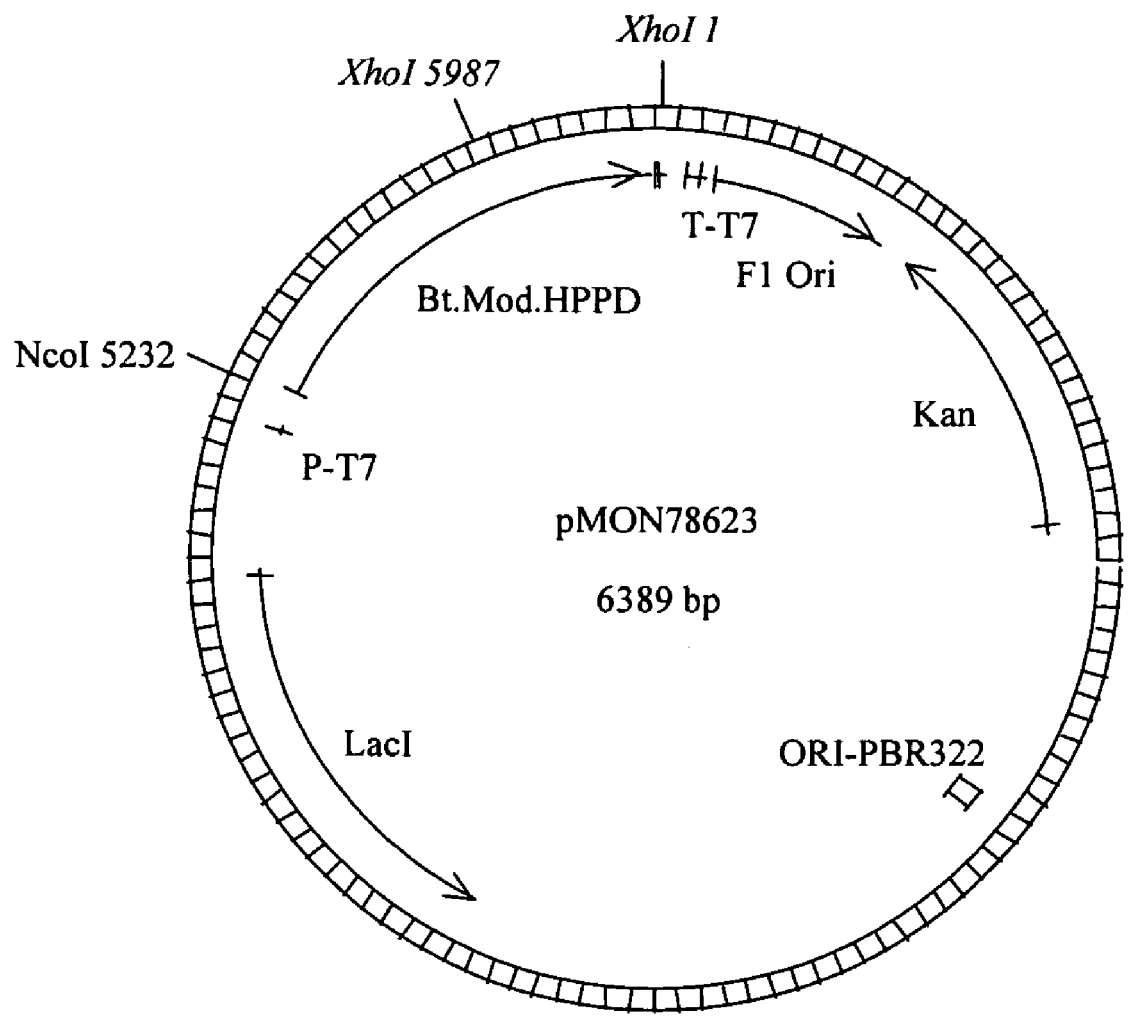
FIG. 23 illustrates the plasmid map of pMON78623.

The binary vectors pMON69907 (FIG. 22), pMON69909 (FIG. 21), pMON77616 (FIG. 20), pMON77619 (FIG. 16), and pMON77622 (FIG. 19) were transformed into *Arabidopsis thaliana*, using the *Agrobacterium*-mediated method described in Example 4. Ti seed from transformed *Arabidopsis* plants were germinated under kanamycin antibiotic selection, and subsequently T2 seed from the *Arabidopsis* transformation events were used for tocopherol analysis. The total tocopherol level of any one event was divided by the mean tocopherol content of the control population and expressed as the fold increase in tocopherol level of the event relative to their respective control population. Data were analyzed using JMP statistical software (SAS Institute, Cary, N.C.). Data was first tested for homogeneity of variances using Levene's test and then the means were compared using the standard least squares method with planned contrasts. Any mean with a Prob>|t| of 0.05 or smaller is considered significantly different from the pMON69907 control. These results are summarized in Table 5. This data shows that additional expression of an HPPD enzyme in the tyrA and At.Atpt2 double gene vector resulted in an increase in the average seed tocopherol content. The most dramatic effects were obtained when the *Arabidopsis* or the cotton HPPD was used in the triple gene combination.

Briefly, the method is a direct germline transformation into individual soybean cells in the meristem of an excised soybean embryo. The soybean embryo is removed after surface sterilization and germination of the seed. The explants are then plated on OR media, a standard MS medium as modified according to Barwale et al., *Plants*, 167:473–481, 1986, plus 3 mg/L BAP, 200 mg/L Carbenicillin, 62.5 mg/L Cefotaxime, 60 mg/L Benomyl, and stored at 15° C. overnight in the dark. The following day the explants are wounded with a scalpel blade and inoculated with the *Agrobacterium* culture prepared as described above. The inoculated explants are then cultured for 3 days at room temperature.

Following the post-transformation culture, the meristematic region is then cultured on standard plant tissue culture media in the presence of the herbicide glyphosate (Monsanto Company, St. Louis, Mo.), which acts as both a selection agent and a shoot-inducing hormone. Media compositions and culture lengths are detailed in the aforementioned U.S. Pat. No. 6,384,301. After 5 to 6 weeks, the surviving

TABLE 5

Tocopherol content of transgenic *Arabidopsis* seed obtained by transformation with pMON69907, pMON69909, pMON77616, pMON77619, or pMON77622.

| pMON | Gene Combinations | N | Mean | Std Dev | Std Err Mean | Prob > |t| |
|---|---|---|---|---|---|---|
| pMON69907 | Eh.tyrA::At.Atpt2 | 30 | 1.80 | 0.38 | 0.07 | |
| pMON69909 | At.HPPD::Eh.tyrA::At.Atpt2 | 20 | 2.97 | 0.72 | 0.16 | 6.00E−11 |
| pMON77616 | Syn.HPPD::Eh.tyrA::At.Atpt2 | 36 | 2.06 | 0.47 | 0.08 | 0.0685 |
| pMON77619 | Bt.Met14.HPPD::Eh.tyrA::At.Atpt2 | 35 | 2.07 | 0.41 | 0.07 | 0.0631 |
| pMON77622 | Gh1.HPPD::Eh.tyrA::At.Atpt2 | 32 | 2.66 | 0.84 | 0.15 | 2.80E−08 |

Variances not equal, Levene's method, P < 0.0001.
There is an effect due to treatment, SLS, P < 0.0001.
Means with a Prob > |t| value <0.05 are significantly different from pMON69907, Planned Contrasts.
Species abbreviations are as follows: At. is *Arabidopsis thaliana*; Bt. is *Bacillus thuringiensis*; Eh. is *Erwinia herbicola*; Gh. is *Gossypium hirsutum* and Syn is *Synechocystis*. Enzyme abbreviations are in Table 1.

Example 4

This example sets forth the transformation of plants with DNA constructs that provide enhanced tocopherol levels. The DNA constructs include but are not limited to pMON69907, pMON69909, pMON77616, pMON77618, pMON77619, pMON77621, and pMON77622. Transgenic *Arabidopsis thaliana* plants may be obtained by *Agrobacterium*-mediated transformation as described by Valverkens et al., *Proc. Nat. Acad. Sci. (U.S.A.)*, 85:5536–5540, 1988, oras described by Bent et al., *Science*, 265:1856–1860, 1994; or Bechtold et al., *C.R. Acad. Sci., Life Sciences*, 316:1194–1199, 1993. Other plant species may be similarly transformed using related techniques. Alternatively, microprojectile bombardment methods, such as described by Klein et al., *Bio/Technology*, 10:286–291, 1992, may also be used to obtain nuclear transformed plants.

Soybean plants are transformed using an *Agrobacterium*-mediated transformation method, as described (U.S. Pat. No. 6,384,301, herein incorporated by reference). For this method, overnight cultures of *Agrobacterium tumefaciens* containing the plasmid that includes a gene of interest, are grown to log phase and then diluted to a final optical density of 0.3 to 0.6 using standard methods known to one skilled in the art. These cultures are used to inoculate the soybean embryo explants prepared as described below.

explants that have a positive phenotype are transferred to soil and grown under greenhouse conditions. Plants are grown to maturity; seed is collected and analyzed for increased tocopherol levels as described in Example 5.

Example 5

This example sets forth the analysis of plant tissues for enhanced tocopherol production. Plants transformed with constructs for the sense or antisense expression of the tocopherol pathway enzymes, including HPPD, are analyzed by HPLC for altered levels of total tocopherols and tocotrienols, as well as altered levels of specific tocopherols and tocotrienols (e.g., $\alpha$, $\beta$, $\gamma$, and $\delta$-tocopherol/tocotrienol).

Extracts of seeds are prepared for HPLC as follows. For *Arabidopsis* seeds, 12 mg of seeds is added to a 1.4 mL Screen Mates tube with a ⅛" steel ball. The tubes are capped and the plate frozen at −80° C. for one hour. The plate, with up to 96 tubes, is shaken for 60 seconds on the 'Megagrinder' at 1000 rpm. As used herein, a 'Megagrinder' is a tissue pulverizer, developed in-house, that operates by use of high speed shaking ball bearings. For soybean seeds, 5 seeds are placed in a 30 mL polypropylene tube with a ¾ inch steel ball, and ground on the Megagrinder for 30 seconds at 1200 rpm. Twenty-five to forty mg of ground soybean seeds is placed in each 1.4 mL Screen Mates tube. For either type of seed the preparation continues as follows.

To each tube is added 500 μL 1% pyrogallol ethanol (Sigma-Aldrich Chemical Company, St. Louis, Mo.), and the plate is shaken on a multitube vortexer (VWR #58816–115) for 15 minutes at speed 10. The extracts are filtered through a 0.2 μm well plate filter into an autosampler well plate. The filtered extracts are then used in HPLC analysis described below.

Leaf extracts are prepared by mixing 30–50 mg of leaf tissue with 1 g microbeads and freezing in liquid nitrogen until extraction. For extraction, 500 μl 1% pyrogallol in ethanol is added to the leaf/bead mixture and shaken for 2×45 seconds using a FastPrep shaker at speed 6.5. The resulting mixture is centrifuged for 4 minutes at 14,000 rpm and filtered through a 0.2 um PTFE filter prior to HPLC analysis.

HPLC is performed on a Zorbax silica HPLC column (4.6 mm×250 mm) (Bodman Industries, Aston, Pa.), using a fluorescent detection monitor, with excitation and emission spectra set at 290 nm and 336 nm, respectively. Solvent A is hexane and solvent B is methyl-t-butyl ether. The injection volume is 20 μL, the flow rate is 1.5 mL/min, the run time is 12 min (40° C.) as described in Table 6.

TABLE 6

Solvent and run-time conditions for HPLC analysis of tocopherols and tocotrienols.

| Time | Solvent A | Solvent B |
| --- | --- | --- |
| 0 minutes | 90% | 10% |
| 10 minutes | 90% | 10% |
| 11 minutes | 25% | 75% |
| 12 minutes | 90% | 10% |

Tocopherol and tocotrienol standards in 1% pyrogallol/ethanol are also run for comparison (α-tocopherol, γ-tocopherol, β-tocopherol, δ-tocopherol, and corresponding tocotrienols (all from Calbiochem, La Jolla, Calif.).

Standard curves for α, β, δ, and γ-tocopherol and α, β, γ, and δ-tocotrienol are calculated using Chemstation software (Agilent Technologies, Palo Alto, Calif.). Tocopherol and tocotrienol values are expressed as ng/mg tissue.

Example 6

This example sets forth the design and construction of a Bt.Mod.HPPD polynucleotide molecule modified for expression in soybean. It is well known in the art that native Bt protein encoding sequences do not express well in plants (U.S. Pat. No. 5,880,275, herein incorporated by reference). Therefore, using a native Bt.Met14.HPPD polypeptide sequence (SEQ ID NO: 8), an artificial Bt protein encoding DNA sequence is designed and constructed by 1) using a codon usage bias similar to that of highly expressed soybean seed proteins, and 2) removal of RNA destabilizing elements previously characterized and known to affect mRNA stability in planta (U.S. Pat. No. 5,880,275). The resulting modified Bt HPPD (SEQ ID NO: 13), designated Bt.Mod.HPPD, encodes a polypeptide designated SEQ ID NO: 14, which is identical in sequence to Bt.Met14.HPPD (SEQ ID NO: 8).

An artificial DNA sequence for Bt.Mod.HPPD (SEQ ID NO: 13) is assembled by methods known in the art (e.g., Withers-Martinez et al., *PCR-based gene synthesis as an efficient approach for expression of the A+T-rich malaria genome, Protein Engineering,* 12:1113–1120, 1999), or is ordered commercially (Blue Heron Biotechnology, Bothell, Wash.). The DNA sequence is cloned as an NcoI-EcoRI restriction fragment into the *E. coli* expression vector pET24d(+) (Novagen, Madison, Wis.) to create pMON78623 (FIG. 23). For assembly into a plant expression cassette, the recombinant plasmid is digested with EcoRI, the EcoRI overhang blunted with a fill-in reaction with T4 DNA polymerase (Sambrook et al., 2001), the plasmid subsequently digested with NcoI, and the approximately 1.1 kilobase insert isolated. In parallel, a vector containing a napin promoter, TS-At.RbcS4, and a napin 3'-UTR flanked by a NotI restriction site and a Bspl20I restriction site (pMON77611) (FIG. 11) is digested with XhoI, the XhoI overhang blunted with T4 DNA polymerase, the plasmid subsequently digested with NcoI, and the approximately 5.7 kb vector backbone containing a napin promoter plus a napin 3'-UTR gel purified using Qiagen spin columns as described in Example 3. The purified fragments are ligated with Ligase (New England Biolabs, Beverly, Mass.) and transformed into *E. coli*, and the correct construct identified and verified by restriction mapping.

To construct a multigene plant transformation vector, the expression cassette, containing the Bt.Mod.HPPD gene driven by the napin promoter at its 5'-end and by a napin 3'-UTR, is excised by a restriction digest of the plasmid using NotI and Bsp120I restriction enzymes. The fragment encoding the Bt.Mod.HPPD expression cassette is gel purified as described in Example 3. In parallel, pMON77609 (FIG. 13), a shuttle vector containing a napin promoter driven expression cassette for the *Erwinia herbicola* tyrA (SEQ ID NO: 25), and the *A. thaliana* HPT (At.Atpt2) (SEQ ID NO: 26) is digested with a Bsp120I restriction enzyme, dephosphorylated with calf intestinal alkaline phosphatase (Roche Applied Science, Indianapolis, Ind.), and gel purified using a Qiagen spin column kit as described in Example 3. The purified dephosphorylated vector is ligated with the purified napin promoter driven HPPD expression cassette to form the triple gene shuttle vector, with the genes in the desired orientation, preferably all head-to-tail. The latter vector serves as a source for the three napin promoter driven expression cassettes for Bt.Mod.HPPD, Eh.tyrA, and At.Atpt2, which are isolated from the plasmid as a single fragment via a Bsp1201NotI double restriction digest. The large fragment is gel purified as described above, and ligated with NotI digested, dephosphorylated and gel purified pMON36524 (FIG. 15). The resulting plant binary vector containing the three napin promoter controlled expression constructs is used for transformation as described in Example 4, plants are grown to maturity, seed is collected, and analyzed for increased tocopherol levels as described in Example 5.

Example 7

This example sets forth the environmental stress tests for drought tolerance, cold tolerance, and salt tolerance, each of which is used alone or in combination to show that plants transformed with tocopherol pathway genes such as HPPD (SEQ ID NOs: 3, 5, 7, 9, 11, 13, 15, 17, 19, 21, and 23) alone or in combination with other tocopherol pathway genes such as tyrA (SEQ ID NO: 25), HPT (SEQ ID NO: 26), and GGH (SEQ ID NO: 27), under the control of a constitutive promoter, e.g., CAMV.35S, are more tolerant to environmental stresses relative to control plants that were not transformed with HPPD genes. The aforementioned HPPD polynucleotide sequences and other tocopherol pathway sequences are cloned into plant binary vectors that contain the glufosinate resistance selection marker. The study design for the stress assays is a single factor design, with the HPPD construct being the factor, where all experimental plants are exposed to a period of drought stress during flowering.

For the drought tolerance test, seeds are stratified in 0.1% phytagar at 4° C. in the dark for 3 days and then sown in flats filled with Metro-Mix® 200 (The Scotts® Company, U.S.A.). Humidity domes are then added to each flat and flats are assigned locations and placed in climate-controlled growth chambers. Plants are grown under a temperature regime of 22° C. day and 20° C. night, with a photoperiod of 16 hours and average light intensity of 170 μmol/m$^2$/s.

After the first true leaves appear, humidity domes are removed and the plants are sprayed with BASTA™ herbicide in Silwet™ L-77 (OSI Specialties Inc., U.S.A.) at a mixture rate of 8.28 mL BASTA™ containing 18.2% active ingredient and 1 mL Silwet diluted to 20 L. After spraying, plants are put back in the growth chamber for 3 additional days. Flats are watered for 1 hour the week following the BASTA™ treatment. Watering is continued every seven days until the flower bud primordia become apparent (growth stage 5.10), at which time plants are watered for the last time. After the last watering, plants are covered with ARACON® (DuPont Company, U.S.A.) sleeves and placed on growth chamber drying racks.

Beginning ten days after the last watering, plants are examined daily until 4 plants/line are wilted. The proportions of wilted and non-wilted HPPD transgenic and control plants are compared over each of the next six days and an overall log rank test is performed to compare the two survival curves using S-PLUS statistical software (S-PLUS 6, Guide to Statistics, Insightful, Seattle, Wash.). The results of that analysis show that the HPPD plants are significantly more tolerant to drought than the control plants, which are not transformed with HPPD genes.

For the cold tolerance test, resistance to cold stress is determined based on the HPPD transformed plant's rate of development, root growth, and chlorophyll accumulation under low temperature conditions relative to control plants that were not transformed with the HPPD genes.

All seedlings used in the experiment are grown at 8° C. Seeds are first surface disinfested using chlorine gas and then seeded on assay plates containing an aqueous solution of 1/2× Gamborg's B-5 Basal Salt Mixture (Sigma-Aldrich Corp., St. Louis, Mo. O G-5788), 1% Phytagel™ (Sigma-Aldrich, P-8169), and 10 ug/ml BASTA™ (Bayer Crop Science, Frankfurt, Germany), with the final pH adjusted to 5.8 using KOH. BASTA™ serves as the selection agent for positively transformed plants. Test plates are held vertically for 28 days at a constant temperature of 8° C., a photoperiod of 16 hr, and average light intensity of approximately 100 μmol/m$^2$/s. Racks holding the plates vertically are rotated daily within the growth chamber. At 28 days post germination, root length is measured, the visual color is assessed, and a whole plate photograph is taken. The results show plants transformed with HPPD gene constructs are significantly resistant to cold stress.

For the salt tolerance test, resistance to high salt stress is based on the plant's rate of development, root growth, and chlorophyll accumulation under high salt conditions relative to control plants that were not transformed with HPPD genes.

All seedlings used in the experiment are grown at a temperature of 22° C. day and 20° C. night, a 16-hour photoperiod, an average light intensity of approximately 120 μmol/m$^2$ and a high salinity level (90 mM NaCl). Seeds are seeded onto BASTA™ plates and selected as described in above. The test lasts 11 days. On day 14 (including 3 days of seed stratification) plants are scored for primary root length, growth stage, visual color, and fresh weight. A photograph of the whole plate is also taken on day 14. The results show that under high salinity conditions, seedlings not transformed with HPPD become stunted, chlorotic, and have less biomass accumulation when compared to transformed plants expressing HPPD genes.

Example 8

This example sets forth the production of HPPD peptide antigens and antibodies. Polyclonal antibodies (pAb), with specificity for select HPPD antigens, were made by a commercial antisera service, Sigma-Genosys (Sigma-Aldrich, Woodlands, Tex.). Sigma-Genosys performed custom peptide synthesis, conjugation, immunization, and sera collection. The custom peptides were made as follows and are described in Table 7. The polypeptide sequence for *Arabidopsis thaliana* HPPD (SEQ ID NO: 37) was analyzed by Sigma-Genosys to identify the peptide antigens SEQ ID NOs: 38 and 39. The peptide antigen, SEQ ID NO: 38, contained a native N-terminal cysteine. The peptide antigen, SEQ ID NO: 39, did not contain an N-terminal cysteine so one was added. Both peptide antigens were produced by the m-Maleimidobenzoyl-N-hydroxysuccinimide ester (MBS) method. (Antigen Design & Sera Purification Tech Sheet, Sigma-Genosys).

TABLE 7

Target HPPD polypeptides, antigen sequences and methods used for their production.

| Target HPPD Polypeptide | | Antigen Sequence | | Method |
| --- | --- | --- | --- | --- |
| *Arabidopsis thaliana* HPPD | (SEQ ID NO: 37) | CMMKDEEGKAYQSGG | (SEQ ID NO: 38) | MBS |
| *Arabidopsis thaliana* HPPD | (SEQ ID NO: 37) | CRTLREMRKRSSIGG | (SEQ ID NO: 39) | MBS |
| *Bacillus thuringiensis* HPPD | (SEQ ID NO: 8) | GILVDRDDEGYLLQIFTKPC | (SEQ ID NO: 42) | KLH/MBS |
| *Synechocystis sp.* HPPD | (SEQ ID NO: 40) | EILLDDQDNTGERLL | (SEQ ID NO: 41) | EDC |
| UNI-HPPD-1 | (SEQ ID NOs: 37, 18, 20, and 22) | GILVDRDDQGTLLQIFTKPC | (SEQ ID NO: 43) | KLH/MBS |

The polypeptide sequence for *Synechocystis* sp. HPPD (SEQ ID NO: 40) was analyzed by Sigma-Genosys to identify the peptide antigen (SEQ ID NO: 41). The peptide antigen was produced by the 1-ethyl-3-(3-dimethylaminopropyl)carbodiimide hydrochloride (EDC) method.

The sequence for the *Bacillus thuringiensis* peptide antigen (SEQ ID NO: 42) was based on a *Bacillus thuringiensis*

HPPD polypeptide sequence (SEQ ID NO: 8). The peptide antigen was produced by the m-Maleimidobenzoyl-N-hydroxysuccinimide ester (MBS) method. An N-terminal cysteine amino acid was added to the native peptide sequence.

The sequence for the Uni-HPPD peptide antigen (SEQ ID NO: 43) was made by identification of a peptide fragment common to the polypeptide sequences of *Arabidopsis thaliana* HPPD (SEQ ID NO: 37), *Brassica napus* HPPD (SEQ ID NO: 20), *Gossypium hirsutum* HPPD (SEQ ID NO: 18), and *Lycopersicon esculentum* (SEQ ID NO: 22). A C-terminal cysteine was added to the peptide antigen. The peptide was produced by the m-Maleimidobenzoyl-N-hydroxysuccinimide ester (MBS) method.

The protocol for antigen synthesis and conjugation as described by the manufacturer is provided below. Approximately 10 mg of each peptide antigen (SEQ ID NOs: 38, 39, 41, 42, and 43) was synthesized. The synthesized peptide antigens were analyzed by mass spectral and HPLC analyses to ensure sequence integrity and purity prior to conjugation. The peptides were conjugated to 2–3 mg of Keyhole Limpet Hemocyanin (KLH) or Bovine Serum Albumin (BSA). The pepyide-protein conjugates were purified by gel filtration and freeze dried. Rabbits were then immunized by subcutaneous injection of the conjugated peptides (Table 8). The initial immunization was given in Complete Freund's Adjuvant with all subsequent immunizations given in Incomplete Freund's Adjuvant. The unconjugated peptides, the pre-immune bleeds and the first production bleeds were obtained and used in the experiments described below. Antisera were unpurified and contained a number of different isotypes (IgG, IgM, IgA). Total sera of 15–25 mL per rabbit per bleed were obtained (~120 mL of total sera).

TABLE 8

The Immunization and Bleed Protocol.

| Day | Procedure |
| --- | --- |
| 0 | Pre-bleed, Antigen injection |
| 14 | Antigen injection |
| 28 | Antigen injection |
| 42 | Antigen injection |
| 49 | Bleed |
| 56 | Antigen injection |
| 63 | Bleed |
| 70 | Antigen injection |
| 77 | Bleed |
| End of standard protocol | |

The aforementioned antibodies were used in a Western blot analysis to test for expression of HPPD protein in *E. coli* bacteria, and in *Arabidopsis thaliana* and *Glycine max* plants transformed to express HPPD polynucleotide sequences. Total protein extracts from *E. coli* were obtained by boiling induced cells in 1X Laemelli gel sample buffer. Total protein from *A. thaliana* seeds was obtained by pulverizing the seeds in a BIO101/Savant FastPrep™ FP120 high-speed reciprocating cell membrane disruptor (Qbiogene, Inc., Carlsbad, Calif.) Total protein from *Glycine max* was obtained from lyophilized seed powder prepared as described Example 5. In all cases, the crude protein extracts were solubilized in 300 to 500 μL of 100 mM potassium phosphate buffer, pH 7.0, or Tris buffered saline (TBS), pH 8.0. Solubilized extracts contained a proteinase inhibitor cocktail added according to the manufacturer's specification (Complete™ Protease Inhibitor Cocktail, Boehringer Mannheim, Mannheim, Germany). Between 6 and 20 μg of extracted total protein from *A. thalina* or soybean seed was separated by electrophoresis (Proteins and Proteomics: A Laboratory Manual, 2002. Simpson and Hotchkiss, eds.) using a 4 to 15% or 4 to 20% polyacrylamide gradient gel containing SDS.

The HPPD polynucleotide sequences expressed in *E. coli* included *Arabidopsis thaliana* (SEQ ID NO: 2), *Bacillus thuringiensis* (SEQ ID NO: 7), *Brassica napus* (SEQ ID NO: 19), *Gossypium hirsutum* (SEQ ID NO: 15), *Synechocystis* sp.(SEQ ID NO: 1), *Lycopersicon esculentum* (SEQ ID NO: 21), a *Bacillus thuringiensis* (SEQ ID NO: 7)/TyrA (SEQ ID NO: 25) fusion protein and a *Gossypium hirsutum* (SEQ ID NO: 15)/TyrA (SEQ ID NO: 25) fusion protein. Empty vector and TyrA (SEQ ID NO: 25) constructs were included as controls. After electrophoresis, the proteins were transferred to a polyvinylidene fluoride (PVDF) membrane (Millipore, Immobilon-P, #IPVH304F0, Bedford, Mass.) and the membrane probed with a primary antibody (1:5000 dilution) produced from a rabbit injected with a combination of *Bacillus thuringiensis* (SEQ ID NO: 42) and UNI-HPPD-1 (SEQ ID NO: 43) peptide fragments. An anti-rabbit IgG secondary antibody (Sigma-Aldrich, #A3687) was used to visualize HPPD-proteins. The results of the Western analysis are shown in Table 9.

TABLE 9

Detection of HPPD protein in extracts of *E. coli* expressed

| HPPD Source | HPPD detected |
| --- | --- |
| *Arabidopsis thaliana* (SEQ ID NO: 2) | Yes |
| *Bacillus thuringiensis* (SEQ ID NO: 7) | Yes |
| *Brassica napus* (SEQ ID NO: 19) | No |
| *Gossypium hirsutum* (SEQ ID NO: 15) | Yes |
| *Synechocystis* (SEQ ID NO: 1) | No |
| *Bacillus thuringiensis* (SEQ ID NO: 7)/ TyrA (SEQ ID NO: 25) fusion protein | Yes |
| *Gossypium hirsutum* (SEQ ID NO: 15)/ TyrA (SEQ ID NO: 25) fusion protein | Yes |
| *Lycopersicon esculentum* (SEQ ID NO: 21) | Yes |
| TyrA (SEQ ID NO: 25) | No |
| Empty vector | No |

The *Arabidopsis* HPPD polynucleotide sequence (SEQ ID NO: 2) was also expressed in transformed *A. thaliana* and *G. max* plants. After isolation as described in Example 5, the electrophoresed proteins were blotted onto PVDF membrane, and probed with the anti-*Arabidopsis* HPPD rabbit primary antibody described above. Sixteen transformed *Arabidopsis* lines were tested using the anti-*Arabidopsis* HPPD antibody. One line, as well as the wild-type untransformed control, tested negative for HPPD protein. Fifteen lines produced a positive response. Similarly, seven *Glycine max* lines transformed with the *Arabidopsis thaliana* HPPD (SEQ ID NO: 2) were tested using the anti-*Arabidopsis* HPPD antibody. One line, as well as the wild-type untransformed control, tested negative for the HPPD protein. Six lines tested positive for the HPPD protein.

Having illustrated and described the principles of the present invention, it should be apparent to persons skilled in the art that the present invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A substantially purified polynucleotide molecule comprising:
   (a) a polynucleotide molecule comprising a nucleotide sequence selected from the group consisting of: SEQ ID NO: 15 and SEQ ID NO: 17;
   (b) a polynucleotide molecule encoding a 4-hydroxyphenylpyruvate dioxygenase ("HPPD") polypeptide or polypeptide having HPPD activity comprising a sequence selected from the group consisting of:
   a nucleotide sequence having at least 95% indentity to SEQ ID NO: 15 and a nucleotide sequence having at least 95% indentity to SEQ ID NO: 17;
   (c) a polynucleotide molecule comprising a polynucleotide sequence encoding a polypeptide comprising a sequence selected from the group consisting of:
   SEQ ID NO: 16 and SEQ ID NO: 18; or
   (d) a polynucleotide molecule comprising a polynucleotide sequence encoding a 4-hydroxyphenylpyruvate dioxygenase ("HPPD") polypeptide or polypeptide having HPPD activity comprising a sequence selected from the group consisting of:
   a polypeptide sequence having at least 95% identity to SEQ ID NO: 16 and a polypeptide sequence having at least 95% identity to SEQ ID NO: 18.

2. A DNA construct comprising the substantially purified polynucleotide molecule of claim 1.

3. The DNA construct of claim 2, further comprising a seed-preferred promoter operably linked to the polynucleotide molecule.

4. The DNA construct of claim 3, wherein the seed-preferred promoter is selected from the group consisting of: napin, 7S alpha, 7S alpha', 7S beta, USP 88, enhanced USP 88, Arcelin 5, and oleosin.

5. The DNA construct of claim 2, further comprising a polynucleotide encoding a chloroplast transit peptide.

6. A plant cell transformed with the DNA construct of claim 2.

7. The DNA construct of claim 2 wherein the substantially purified polynucleotide molecule comprises the polynucleotide sequence of SEQ ID NO: 15.

8. A method of producing a 4-hydroxyphenylpyruvate dioxygenase ("HPPD") polypeptide, comprising expressing the nucleic acid of claim 1 in a transgenic plant cell or bacterial cell.

9. The method of claim 8, wherein the cell is a plant cell.

10. The method of claim 9, wherein the plant cell is selected from the group consisting of Brassica campestris, canola, oilseed rape, and soybean.

11. The substantially purified polynucleotide molecule of claim 1, wherein the polynucleotide molecule encodes SEQ ID NO: 16.

12. The substantially purified polynucleotide molecule of claim 1, wherein the polynucleotide molecule encodes SEQ ID NO: 18.

13. The substantially purified polynucleotide molecule of claim 1, wherein the polynucleotide molecule comprises SEQ ID NO: 15.

14. The substantially purified polynucleotide molecule of claim 1, wherein the polynucleotide molecule comprises SEQ ID NO: 17.

15. The substantially purified polynucleotide molecule of claim 1, wherein the polynucleotide molecule encodes a polypeptide sequence having at least 95% identity to SEQ ID NO: 16.

16. The substantially purified polynucleotide molecule of claim 1, wherein the polynucleotide molecule encodes a polypeptide sequence having at least 95% identity to SEQ ID NO: 18.

17. The substantially purified polynucleotide molecule of claim 1, wherein the polynucleotide molecule comprises a nucleotide sequence having at least 95% identity to SEQ ID NO: 15.

18. The substantially purified polynucleotide molecule of claim 1, wherein the polynucleotide molecule comprises a nucleotide sequence having at least 96% identity to SEQ ID NO: 17.

* * * * *

UNITED STATES PATENT AND TRADEMARK OFFICE
CERTIFICATE OF CORRECTION

PATENT NO. : 7,297,541 B2
APPLICATION NO. : 11/043542
DATED : November 20, 2007
INVENTOR(S) : Moshiri et al.

It is certified that error appears in the above-identified patent and that said Letters Patent is hereby corrected as shown below:

In claim 18, column 110, line 50, delete "96" and insert --95--.

Signed and Sealed this

Twenty-ninth Day of April, 2008

JON W. DUDAS
*Director of the United States Patent and Trademark Office*

SEQUENCE LISTING

<160> NUMBER OF SEQ ID NOS: 44

<210> SEQ ID NO 1
<211> LENGTH: 1020
<212> TYPE: DNA
<213> ORGANISM: Synechocystis PCC6803

<400> SEQUENCE: 1

```
atggaattcg actatcttca tttatacgtt gacgattatc agtcagctca tcgttgttat      60
caacgtcaat ggggtttcac ttgcgtaaat aaaattatta ctgaccaagg aattactggc     120
atctaccaac aggggcaaat acttctgcta atttcggcat cggaatctag tttgagtaga     180
tatgccgact atctccagaa acatccccce ggcgtaggtg aagtcgcttg caggtggcc      240
aattggcaaa aaattcagca tcaattatca gaattacaga tagaaaccac accagttatt     300
catcctctga ctaaagcaga aggattaact tttttgctct ggggagatgt gcaccatagc     360
atttatcctg ttcgttctga gctaaatcag aataaaacat tgcatggtgt tggtttaacg     420
accatcgacc atgtggtgct aaacattgcc gccgatcaat ttacccaggc ttcccaatgg     480
tatcaacagg tgtttggctg gtcggtgcag cagagtttta ctgtcaatac gccccattct     540
ggtctgtata gcgaagccct ggccagtgcc aatgggaaag tccaatttaa cctcaattgt     600
cccaccaata acagttccca aattcaaact ttttagcca ataaccatgg ggctggtatt      660
caacatgtcg cttttttccac tacgagtatt acgcgaactg tggctcatct gcgggaaagg    720
ggcgtaaatt ttttaaaaat ccccactggc tattatcaac agcaaagaaa cagtagctat     780
tttaattatg caagtttgga ttgggatacc ttacagtgcc tagaaatttt gctggatgat    840
caagataata cggggagcg attactgcta caaattttta gtcagccttg ctatggagta     900
ggcactctat tttgggaaat tattgaacgc gccaccggg caaaaggatt tggtcaagga    960
aactttcaag ctctctatga agcggtggag actttagaaa acagttaga agtgccataa   1020
```

<210> SEQ ID NO 2
<211> LENGTH: 1338
<212> TYPE: DNA
<213> ORGANISM: Arabidopsis thaliana

<400> SEQUENCE: 2

```
atgggccacc aaaacgccgc cgtttcagag aatcaaaacc atgatgacgg cgctgcgtcg     60
tcgccgggat tcaagctcgt cggatttttcc aagttcgtaa gaaagaatcc aaagtctgat   120
aaattcaagg ttaagcgctt ccatcacatc gagttctggt gcggcgacgc aaccaacgtc   180
gctcgtcgct tctcctgggg tctggggatg agattctccg ccaaatccga tctttccacc   240
ggaaacatgg ttcacgcctc ttacctactc acctccggtg acctccgatt ccttttcact   300
gctccttact ctccgtctct ctccgccgga gagattaaac cgacaaccac agcttctatc   360
ccaagtttcg atcacggctc ttgtcgttcc ttcttctctt cacatggtct cggtgttaga   420
gccgttgcga ttgaagtaga agacgcagag tcagctttct ccatcagtgt agctaatggc   480
gctattcctt cgtcgcctcc tatcgtcctc aatgaagcag ttacgatcgc tgaggttaaa   540
ctatacggcg atgttgttct ccgatatgtt agttacaaag cagaagatac cgaaaaatcc   600
gaattcttgc cagggttcga gcgtgtagag gatgcgtcgt cgttcccatt ggattatggt   660
atccggcggc ttgaccacgc cgtgggaaac gttcctgagc ttggtccggc tttaacttat   720
gtagcgggt tcactggttt tcaccaattc gcagagttca cagcagacga cgttggaacc   780
```

-continued

```
gccgagagcg gtttaaattc agcggtcctg gctagcaatg atgaaatggt tcttctaccg    840
attaacgagc cagtgcacgg aacaaagagg aagagtcaga ttcagacgta tttggaacat    900
aacgaaggcg cagggctaca acatctggct ctgatgagtg aagacatatt caggaccctg    960
agagagatga ggaagaggag cagtattgga ggattcgact tcatgccttc tcctccgcct   1020
acttactacc agaatctcaa gaaacgggtc ggcgacgtgc tcagcgatga tcagatcaag   1080
gagtgtgagg aattagggat tcttgtagac agagatgatc aagggacgtt gcttcaaatc   1140
ttcacaaaac cactaggtga caggccgacg atatttatag agataatcca gagagtagga   1200
tgcatgatga aagatgagga agggaaggct taccagagtg gaggatgtgg tggttttggc   1260
aaaggcaatt tctctgagct cttcaagtcc attgaagaat acgaaaagac tcttgaagcc   1320
aaacagttag tgggatga                                                 1338
```

<210> SEQ ID NO 3
<211> LENGTH: 1686
<212> TYPE: DNA
<213> ORGANISM: Bacillus thuringiensis

<400> SEQUENCE: 3

```
cagcattcat ggctaattaa acgctgcggt tgaaacttga ttcaacgaat aatcaaaaag     60
ccactgaata aaatcccgct ttatttcaaa gagaaaaaag tcgaatttta tatgtaagaa    120
aaaaagagga atttgacaga aaagatagaa aattttaaag gtcagaattt gttagcttgc    180
taactaattt ctattaatta atgttggaag cgttttcggt tggttttaag tatggaccat    240
ttaatctatt tacaggggga tgaagatatt atgaaacaaa aatctatgga tacgctagct    300
gcacaaatgg aggacttttt tccagtacgt gatgtagatc atttggaatt ttacgtaggg    360
aatgcaaagc aatcgagtta ttatcttgcg agagcgttcg gattcaaaat tgtagcttac    420
tctggattag aaactggaaa ccgtgaaaag gtatcttatg ttcttgtgca aaaaaatatg    480
cgtttcgttg tgtctggagc tttaagtagt gaaaatcgta ttgcagagtt tgtaaagact    540
catggtgatg gcgtgaagga tgtggcacta cttgttgatg atgttgataa agcatactca    600
gaagcagtga aacgtggtgc cgtcgcaatt gctccaccgc aggaattaac agatgaggac    660
ggtacattga aaaaagcagt tattggtacg tatggtgata caattcatac gcttgtagag    720
cgtaaaaatt ataaaggggc atttatgcca ggattccaaa aggtagaatt taatattcca    780
tttgaggagt ctggtttaat tgctgttgat catgtagttg gtaatgttga aaaaatggaa    840
gagtgggtta gttattacga gaatgttatg ggctttaaac aaatgattca ttttgatgat    900
gacgatatta gtacagagta ttcggcgtta atgtcaaaag ttatgacgaa tggaagtcgt    960
attaagtttc ctattaacga accagcagac ggaaagagaa agtcacaaat tcaagagtat   1020
ctagaattct ataatggagc tggtgtacaa catcttgctt tattaacaag tgatattgtt   1080
aaaacagttg aagcgcttcg tgcaaatggg gtggagtttt tagatacacc tgatacttat   1140
tacgatgagc taactgcacg agttggaaaa atcgatgaag aaattgataa gttaaaagaa   1200
ttaaagatct tagtagatcg tgatgatgaa ggttacttac tacaaatctt tacgaaacca   1260
attgtagatc gtccgacttt atttattgaa atcattcaac gtaaaggttc tcgtggattt   1320
ggtgaaggaa actttaaagc gttattcgaa tcaattgaaa gagaacaaga gcgtcgcgga   1380
aacttataag atttgtatcc accagcaaaa gtccctttgc tggtggaaat ttcattttta   1440
taaggaggaa tcaggatgaa atttgttaca tttcgtcttc cttcaaaaga actacgggct   1500
```

```
ggatggcttg aaggtgacaa agtaatagat atgaatcttg ctagtgaagg gaaaatccct   1560
tcttctatga tagatttttt agagaaagcg gatgagtatg tagaagtagt gcggaatatt   1620
aagaatccaa ataagggtat atatgcttta gaagaagtac aattgacagc tgctcttcct   1680
aatccg                                                              1686

<210> SEQ ID NO 4
<211> LENGTH: 385
<212> TYPE: PRT
<213> ORGANISM: Bacillus thuringiensis

<400> SEQUENCE: 4

Met Asp His Leu Ile Tyr Leu Gln Gly Asp Glu Asp Ile Met Lys Gln
1               5                   10                  15

Lys Ser Met Asp Thr Leu Ala Ala Gln Met Glu Asp Phe Phe Pro Val
                20                  25                  30

Arg Asp Val Asp His Leu Glu Phe Tyr Val Gly Asn Ala Lys Gln Ser
            35                  40                  45

Ser Tyr Tyr Leu Ala Arg Ala Phe Gly Phe Lys Ile Val Ala Tyr Ser
        50                  55                  60

Gly Leu Glu Thr Gly Asn Arg Glu Lys Val Ser Tyr Val Leu Val Gln
65                  70                  75                  80

Lys Asn Met Arg Phe Val Val Ser Gly Ala Leu Ser Ser Glu Asn Arg
                85                  90                  95

Ile Ala Glu Phe Val Lys Thr His Gly Asp Gly Val Lys Asp Val Ala
            100                 105                 110

Leu Leu Val Asp Asp Val Asp Lys Ala Tyr Ser Glu Ala Val Lys Arg
        115                 120                 125

Gly Ala Val Ala Ile Ala Pro Pro Gln Glu Leu Thr Asp Glu Asp Gly
130                 135                 140

Thr Leu Lys Lys Ala Val Ile Gly Thr Tyr Gly Asp Thr Ile His Thr
145                 150                 155                 160

Leu Val Glu Arg Lys Asn Tyr Lys Gly Ala Phe Met Pro Gly Phe Gln
                165                 170                 175

Lys Val Glu Phe Asn Ile Pro Phe Glu Glu Ser Gly Leu Ile Ala Val
            180                 185                 190

Asp His Val Val Gly Asn Val Glu Lys Met Glu Glu Trp Val Ser Tyr
        195                 200                 205

Tyr Glu Asn Val Met Gly Phe Lys Gln Met Ile His Phe Asp Asp Asp
210                 215                 220

Asp Ile Ser Thr Glu Tyr Ser Ala Leu Met Ser Lys Val Met Thr Asn
225                 230                 235                 240

Gly Ser Arg Ile Lys Phe Pro Ile Asn Glu Pro Ala Asp Gly Lys Arg
                245                 250                 255

Lys Ser Gln Ile Gln Glu Tyr Leu Glu Phe Tyr Asn Gly Ala Gly Val
            260                 265                 270

Gln His Leu Ala Leu Leu Thr Ser Asp Ile Val Lys Thr Val Glu Ala
        275                 280                 285

Leu Arg Ala Asn Gly Val Glu Phe Leu Asp Thr Pro Asp Thr Tyr Tyr
290                 295                 300

Asp Glu Leu Thr Ala Arg Val Gly Lys Ile Asp Glu Glu Ile Asp Lys
305                 310                 315                 320

Leu Lys Glu Leu Lys Ile Leu Val Asp Arg Asp Asp Glu Gly Tyr Leu
                325                 330                 335
```

Leu Gln Ile Phe Thr Lys Pro Ile Val Asp Arg Pro Thr Leu Phe Ile
            340                 345                 350

Glu Ile Ile Gln Arg Lys Gly Ser Arg Gly Phe Gly Glu Gly Asn Phe
        355                 360                 365

Lys Ala Leu Phe Glu Ser Ile Glu Arg Glu Gln Glu Arg Arg Gly Asn
    370                 375                 380

Leu
385

<210> SEQ ID NO 5
<211> LENGTH: 1158
<212> TYPE: DNA
<213> ORGANISM: Bacillus thuringiensis

<400> SEQUENCE: 5
atggaccatt taatctattt acaggggat gaagatatta tgaaacaaaa atctatggat        60
acgctagctg cacaaatgga ggactttttt ccagtacgtg atgtagatca tttggaattt       120
tacgtaggga atgcaaagca atcgagttat tatcttgcga gagcgttcgg attcaaaatt       180
gtagcttact ctggattaga aactggaaac cgtgaaaagg tatcttatgt tcttgtgcaa       240
aaaaatatgc gtttcgttgt gtctggagct ttaagtagtg aaaatcgtat tgcagagttt       300
gtaaagactc atggtgatgg cgtgaaggat gtggcactac ttgttgatga tgttgataaa       360
gcatactcag aagcagtgaa acgtggtgcc gtcgcaattg ctccaccgca ggaattaaca       420
gatgaggacg gtacattgaa aaaagcagtt attggtacgt atggtgatac aattcatacg       480
cttgtagagc gtaaaaatta taagggggca tttatgccag gattccaaaa ggtagaattt       540
aatattccat ttgaggagtc tggtttaatt gctgttgatc atgtagttgg taatgttgaa       600
aaaatggaag agtgggttag ttattacgag aatgttatgg gctttaaaca aatgattcat       660
tttgatgatg acgatattag tacagagtat tcggcgttaa tgtcaaaagt tatgacgaat       720
ggaagtcgta ttaagtttcc tattaacgaa ccagcagacg gaaagagaaa gtcacaaatt       780
caagagtatc tagaattcta taatggagct ggtgtacaac atcttgcttt attaacaagt       840
gatattgtta aaacagttga agcgcttcgt gcaaatgggg tggagttttt agatacacct       900
gatacttatt acgatgagct aactgcacga gttggaaaaa tcgatgaaga aattgataag       960
ttaaaagaat taaagatctt agtagatcgt gatgatgaag gttacttact acaaatcttt      1020
acgaaaccaa ttgtagatcg tccgactta tttattgaaa tcattcaacg taaaggttct      1080
cgtggatttg gtgaaggaaa ctttaaagcg ttattcgaat caattgaaag agaacaagag      1140
cgtcgcggaa acttataa                                                  1158

<210> SEQ ID NO 6
<211> LENGTH: 385
<212> TYPE: PRT
<213> ORGANISM: Bacillus thuringiensis

<400> SEQUENCE: 6

Met Asp His Leu Ile Tyr Leu Gln Gly Asp Glu Asp Ile Met Lys Gln
1               5                   10                  15

Lys Ser Met Asp Thr Leu Ala Ala Gln Met Glu Asp Phe Phe Pro Val
            20                  25                  30

Arg Asp Val Asp His Leu Glu Phe Tyr Val Gly Asn Ala Lys Gln Ser
        35                  40                  45

Ser Tyr Tyr Leu Ala Arg Ala Phe Gly Phe Lys Ile Val Ala Tyr Ser
    50                  55                  60

```
Gly Leu Glu Thr Gly Asn Arg Glu Lys Val Ser Tyr Val Leu Val Gln
 65                  70                  75                  80

Lys Asn Met Arg Phe Val Ser Gly Ala Leu Ser Ser Glu Asn Arg
                 85                  90                  95

Ile Ala Glu Phe Val Lys Thr His Gly Asp Gly Val Lys Asp Val Ala
            100                 105                 110

Leu Leu Val Asp Val Asp Lys Ala Tyr Ser Glu Ala Val Lys Arg
            115                 120                 125

Gly Ala Val Ala Ile Ala Pro Pro Gln Glu Leu Thr Asp Glu Asp Gly
        130                 135                 140

Thr Leu Lys Lys Ala Val Ile Gly Thr Tyr Gly Asp Thr Ile His Thr
145                 150                 155                 160

Leu Val Glu Arg Lys Asn Tyr Lys Gly Ala Phe Met Pro Gly Phe Gln
                165                 170                 175

Lys Val Glu Phe Asn Ile Pro Phe Glu Glu Ser Gly Leu Ile Ala Val
            180                 185                 190

Asp His Val Val Gly Asn Val Glu Lys Met Glu Glu Trp Val Ser Tyr
        195                 200                 205

Tyr Glu Asn Val Met Gly Phe Lys Gln Met Ile His Phe Asp Asp Asp
    210                 215                 220

Asp Ile Ser Thr Glu Tyr Ser Ala Leu Met Ser Lys Val Met Thr Asn
225                 230                 235                 240

Gly Ser Arg Ile Lys Phe Pro Ile Asn Glu Pro Ala Asp Gly Lys Arg
                245                 250                 255

Lys Ser Gln Ile Gln Glu Tyr Leu Glu Phe Tyr Asn Gly Ala Gly Val
            260                 265                 270

Gln His Leu Ala Leu Leu Thr Ser Asp Ile Val Lys Thr Val Glu Ala
        275                 280                 285

Leu Arg Ala Asn Gly Val Glu Phe Leu Asp Thr Pro Asp Thr Tyr Tyr
    290                 295                 300

Asp Glu Leu Thr Ala Arg Val Gly Lys Ile Asp Glu Ile Asp Lys
305                 310                 315                 320

Leu Lys Glu Leu Lys Ile Leu Val Asp Arg Asp Asp Glu Gly Tyr Leu
                325                 330                 335

Leu Gln Ile Phe Thr Lys Pro Ile Val Asp Arg Pro Thr Leu Phe Ile
            340                 345                 350

Glu Ile Ile Gln Arg Lys Gly Ser Arg Gly Phe Gly Glu Gly Asn Phe
        355                 360                 365

Lys Ala Leu Phe Glu Ser Ile Glu Arg Glu Gln Glu Arg Arg Gly Asn
    370                 375                 380

Leu
385

<210> SEQ ID NO 7
<211> LENGTH: 1119
<212> TYPE: DNA
<213> ORGANISM: Bacillus thuringiensis

<400> SEQUENCE: 7
atgaaacaaa aatctatgga tacgctagct gcacaaatgg aggactttt tccagtacgt    60 gatgtagatc atttggaatt ttacgtaggg aatgcaaagc aatcgagtta ttatcttgcg   120
agagcgttcg gattcaaaat tgtagcttac tctggattag aaactggaaa ccgtgaaaag   180
gtatcttatg ttcttgtgca aaaaaatatg cgtttcgttg tgtctggagc tttaagtagt   240
```

-continued

```
gaaaatcgta ttgcagagtt tgtaaagact catggtgatg gcgtgaagga tgtggcacta    300
cttgttgatg atgttgataa agcatactca gaagcagtga aacgtggtgc cgtcgcaatt    360
gctccaccgc aggaattaac agatgaggac ggtacattga aaaaagcagt tattggtacg    420
tatggtgata caattcatac gcttgtagag cgtaaaaatt ataaaggggc atttatgcca    480
ggattccaaa aggtagaatt taatattcca tttgaggagt ctggtttaat tgctgttgat    540
catgtagttg gtaatgttga aaaaatggaa gagtgggtta gttattacga gaatgttatg    600
ggctttaaac aaatgattca ttttgatgat gacgatatta gtacagagta ttcggcgtta    660
atgtcaaaag ttatgacgaa tggaagtcgt attaagtttc ctattaacga accagcagac    720
ggaaagagaa agtcacaaat tcaagagtat ctagaattct ataatggagc tggtgtacaa    780
catcttgctt tattaacaag tgatattgtt aaaacagttg aagcgcttcg tgcaaatggg    840
gtggagtttt tagatacacc tgatacttat tacgatgagc taactgcacg agttggaaaa    900
atcgatgaag aaattgataa gttaaaagaa ttaaagatct tagtagatcg tgatgatgaa    960
ggttacttac tacaaatctt tacgaaacca attgtagatc gtccgacttt atttattgaa   1020
atcattcaac gtaaaggttc tcgtggattt ggtgaaggaa actttaaagc gttattcgaa   1080
tcaattgaaa gagaacaaga gcgtcgcgga aacttataa                          1119
```

<210> SEQ ID NO 8
<211> LENGTH: 372
<212> TYPE: PRT
<213> ORGANISM: Bacillus thuringiensis

<400> SEQUENCE: 8

```
Met Lys Gln Lys Ser Met Asp Thr Leu Ala Ala Gln Met Glu Asp Phe
1               5                   10                  15

Phe Pro Val Arg Asp Val Asp His Leu Glu Phe Tyr Val Gly Asn Ala
            20                  25                  30

Lys Gln Ser Ser Tyr Tyr Leu Ala Arg Ala Phe Gly Phe Lys Ile Val
        35                  40                  45

Ala Tyr Ser Gly Leu Glu Thr Gly Asn Arg Glu Lys Val Ser Tyr Val
    50                  55                  60

Leu Val Gln Lys Asn Met Arg Phe Val Val Ser Gly Ala Leu Ser Ser
65                  70                  75                  80

Glu Asn Arg Ile Ala Glu Phe Val Lys Thr His Gly Asp Gly Val Lys
                85                  90                  95

Asp Val Ala Leu Leu Val Asp Asp Val Asp Lys Ala Tyr Ser Glu Ala
            100                 105                 110

Val Lys Arg Gly Ala Val Ala Ile Ala Pro Pro Gln Glu Leu Thr Asp
        115                 120                 125

Glu Asp Gly Thr Leu Lys Lys Ala Val Ile Gly Thr Tyr Gly Asp Thr
    130                 135                 140

Ile His Thr Leu Val Glu Arg Lys Asn Tyr Lys Gly Ala Phe Met Pro
145                 150                 155                 160

Gly Phe Gln Lys Val Glu Phe Asn Ile Pro Phe Glu Glu Ser Gly Leu
                165                 170                 175

Ile Ala Val Asp His Val Val Gly Asn Val Glu Lys Met Glu Glu Trp
            180                 185                 190

Val Ser Tyr Tyr Glu Asn Val Met Gly Phe Lys Gln Met Ile His Phe
        195                 200                 205

Asp Asp Asp Asp Ile Ser Thr Glu Tyr Ser Ala Leu Met Ser Lys Val
```

-continued

```
    210                 215                 220

Met Thr Asn Gly Ser Arg Ile Lys Phe Pro Ile Asn Glu Pro Ala Asp
225                 230                 235                 240

Gly Lys Arg Lys Ser Gln Ile Gln Glu Tyr Leu Glu Phe Tyr Asn Gly
                245                 250                 255

Ala Gly Val Gln His Leu Ala Leu Leu Thr Ser Asp Ile Val Lys Thr
            260                 265                 270

Val Glu Ala Leu Arg Ala Asn Gly Val Glu Phe Leu Asp Thr Pro Asp
        275                 280                 285

Thr Tyr Tyr Asp Glu Leu Thr Ala Arg Val Gly Lys Ile Asp Glu Glu
    290                 295                 300

Ile Asp Lys Leu Lys Glu Leu Lys Ile Leu Val Asp Arg Asp Asp Glu
305                 310                 315                 320

Gly Tyr Leu Leu Gln Ile Phe Thr Lys Pro Ile Val Asp Arg Pro Thr
                325                 330                 335

Leu Phe Ile Glu Ile Ile Gln Arg Lys Gly Ser Arg Gly Phe Gly Glu
            340                 345                 350

Gly Asn Phe Lys Ala Leu Phe Glu Ser Ile Glu Arg Glu Gln Glu Arg
        355                 360                 365

Arg Gly Asn Leu
    370

<210> SEQ ID NO 9
<211> LENGTH: 1104
<212> TYPE: DNA
<213> ORGANISM: Bacillus thuringiensis

<400> SEQUENCE: 9
atggatacgc tagctgcaca aatggaggac ttttttccag tacgtgatgt agatcatttg      60
gaattttacg tagggaatgc aaagcaatcg agttattatc ttgcgagagc gttcggattc     120
aaaattgtag cttactctgg attagaaact ggaaaccgtg aaaaggtatc ttatgttctt     180
gtgcaaaaaa atatgcgttt cgttgtgtct ggagctttaa gtagtgaaaa tcgtattgca     240
gagtttgtaa agactcatgg tgatggcgtg aaggatgtgg cactacttgt tgatgatgtt     300
gataaagcat actcagaagc agtgaaacgt ggtgccgtcg caattgctcc accgcaggaa     360
ttaacagatg aggacggtac attgaaaaaa gcagttattg gtacgtatgg tgatacaatt     420
catacgcttg tagagcgtaa aaattataaa ggggcattta tgccaggatt ccaaaaggta     480
gaatttaata ttccatttga ggagtctggt ttaattgctg ttgatcatgt agttggtaat     540
gttgaaaaaa tggaagagtg ggttagttat tacgagaatg ttatgggctt taaacaaatg     600
attcattttg atgatgacga tattagtaca gagtattcgg cgttaatgtc aaaagttatg     660
acgaatggaa gtcgtattaa gtttcctatt aacgaaccag cagacggaaa gagaaagtca     720
caaattcaag agtatctaga attctataat ggagctggtg tacaacatct tgctttatta     780
acaagtgata ttgttaaaac agttgaagcg cttcgtgcaa atggggtgga gtttttagat     840
acacctgata cttattacga tgagctaact gcacgagttg gaaaaatcga tgaagaaatt     900
gataagttaa aagaattaaa gatcttagta gatcgtgatg atgaaggtta cttactacaa     960
atctttacga aaccaattgt agatcgtccg actttattta ttgaaatcat tcaacgtaaa    1020
ggttctcgtg gatttggtga aggaaacttt aaagcgttat tcgaatcaat tgaaagagaa    1080
caagagcgtc gcggaaactt ataa                                           1104
```

<210> SEQ ID NO 10
<211> LENGTH: 367
<212> TYPE: PRT
<213> ORGANISM: Bacillus thuringiensis

<400> SEQUENCE: 10

Met Asp Thr Leu Ala Ala Gln Met Glu Asp Phe Phe Pro Val Arg Asp
1               5                   10                  15

Val Asp His Leu Glu Phe Tyr Val Gly Asn Ala Lys Gln Ser Ser Tyr
            20                  25                  30

Tyr Leu Ala Arg Ala Phe Gly Phe Lys Ile Val Ala Tyr Ser Gly Leu
        35                  40                  45

Glu Thr Gly Asn Arg Glu Lys Val Ser Tyr Val Leu Val Gln Lys Asn
    50                  55                  60

Met Arg Phe Val Val Ser Gly Ala Leu Ser Ser Glu Asn Arg Ile Ala
65                  70                  75                  80

Glu Phe Val Lys Thr His Gly Asp Gly Val Lys Asp Val Ala Leu Leu
                85                  90                  95

Val Asp Asp Val Asp Lys Ala Tyr Ser Glu Ala Val Lys Arg Gly Ala
            100                 105                 110

Val Ala Ile Ala Pro Pro Gln Glu Leu Thr Asp Glu Asp Gly Thr Leu
        115                 120                 125

Lys Lys Ala Val Ile Gly Thr Tyr Gly Asp Thr Ile His Thr Leu Val
    130                 135                 140

Glu Arg Lys Asn Tyr Lys Gly Ala Phe Met Pro Gly Phe Gln Lys Val
145                 150                 155                 160

Glu Phe Asn Ile Pro Phe Glu Glu Ser Gly Leu Ile Ala Val Asp His
                165                 170                 175

Val Val Gly Asn Val Glu Lys Met Glu Glu Trp Val Ser Tyr Tyr Glu
            180                 185                 190

Asn Val Met Gly Phe Lys Gln Met Ile His Phe Asp Asp Asp Asp Ile
        195                 200                 205

Ser Thr Glu Tyr Ser Ala Leu Met Ser Lys Val Met Thr Asn Gly Ser
    210                 215                 220

Arg Ile Lys Phe Pro Ile Asn Glu Pro Ala Asp Gly Lys Arg Lys Ser
225                 230                 235                 240

Gln Ile Gln Glu Tyr Leu Glu Phe Tyr Asn Gly Ala Gly Val Gln His
                245                 250                 255

Leu Ala Leu Leu Thr Ser Asp Ile Val Lys Thr Val Glu Ala Leu Arg
            260                 265                 270

Ala Asn Gly Val Glu Phe Leu Asp Thr Pro Asp Thr Tyr Tyr Asp Glu
        275                 280                 285

Leu Thr Ala Arg Val Gly Lys Ile Asp Glu Ile Asp Lys Leu Lys
    290                 295                 300

Glu Leu Lys Ile Leu Val Asp Arg Asp Glu Gly Tyr Leu Leu Gln
305                 310                 315                 320

Ile Phe Thr Lys Pro Ile Val Asp Arg Pro Thr Leu Phe Ile Glu Ile
                325                 330                 335

Ile Gln Arg Lys Gly Ser Arg Gly Phe Gly Glu Gly Asn Phe Lys Ala
            340                 345                 350

Leu Phe Glu Ser Ile Glu Arg Glu Gln Glu Arg Arg Gly Asn Leu
        355                 360                 365

<210> SEQ ID NO 11
<211> LENGTH: 1083

<212> TYPE: DNA
<213> ORGANISM: Bacillus thuringiensis

<400> SEQUENCE: 11

```
atggaggact tttttccagt acgtgatgta gatcatttgg aatttacgt agggaatgca      60
aagcaatcga gttattatct tgcgagagcg ttcggattca aaattgtagc ttactctgga     120
ttagaaactg gaaccgtga aaaggtatct tatgttcttg tgcaaaaaaa tatgcgtttc     180
gttgtgtctg gagctttaag tagtgaaaat cgtattgcag agtttgtaaa gactcatggt     240
gatggcgtga aggatgtggc actacttgtt gatgatgttg ataaagcata ctcagaagca     300
gtgaaacgtg gtgccgtcgc aattgctcca ccgcaggaat taacagatga ggacggtaca     360
ttgaaaaaag cagttattgg tacgtatggt gatacaattc atacgcttgt agagcgtaaa     420
aattataaag gggcatttat gccaggattc caaaaggtag aatttaatat tccatttgag     480
gagtctggtt taattgctgt tgatcatgta gttggtaatg ttgaaaaaat ggaagagtgg     540
gttagttatt acgagaatgt tatgggcttt aaacaaatga ttcattttga tgatgacgat     600
attagtacag agtattcggc gttaatgtca aaagttatga cgaatggaag tcgtattaag     660
tttcctatta cgaaccagc agacggaaag agaaagtcac aaattcaaga gtatctagaa     720
ttctataatg gagctggtgt acaacatctt gctttattaa caagtgatat tgttaaaaca     780
gttgaagcgc ttcgtgcaaa tggggtggag tttttagata cacctgatac ttattacgat     840
gagctaactg cacgagttgg aaaaatcgat gaagaaattg ataagttaaa agaattaaag     900
atcttagtag atcgtgatga tgaaggttac ttactacaaa tctttacgaa accaattgta     960
gatcgtccga ctttatttat tgaaatcatt caacgtaaag gttctcgtgg atttggtgaa    1020
ggaaacttta agcgttatt cgaatcaatt gaaagagaac aagagcgtcg cggaaactta    1080
taa                                                                  1083
```

<210> SEQ ID NO 12
<211> LENGTH: 360
<212> TYPE: PRT
<213> ORGANISM: Bacillus thuringiensis

<400> SEQUENCE: 12

Met Glu Asp Phe Phe Pro Val Arg Asp Val Asp His Leu Glu Phe Tyr
1               5                  10                  15

Val Gly Asn Ala Lys Gln Ser Ser Tyr Tyr Leu Ala Arg Ala Phe Gly
            20                  25                  30

Phe Lys Ile Val Ala Tyr Ser Gly Leu Glu Thr Gly Asn Arg Glu Lys
        35                  40                  45

Val Ser Tyr Val Leu Val Gln Lys Asn Met Arg Phe Val Val Ser Gly
    50                  55                  60

Ala Leu Ser Ser Glu Asn Arg Ile Ala Glu Phe Val Lys Thr His Gly
65                  70                  75                  80

Asp Gly Val Lys Asp Val Ala Leu Leu Val Asp Asp Val Asp Lys Ala
                85                  90                  95

Tyr Ser Glu Ala Val Lys Arg Gly Ala Val Ala Ile Ala Pro Pro Gln
            100                 105                 110

Glu Leu Thr Asp Glu Asp Gly Thr Leu Lys Lys Ala Val Ile Gly Thr
        115                 120                 125

Tyr Gly Asp Thr Ile His Thr Leu Val Glu Arg Lys Asn Tyr Lys Gly
    130                 135                 140

Ala Phe Met Pro Gly Phe Gln Lys Val Glu Phe Asn Ile Pro Phe Glu

-continued 145 150 155 160

Glu Ser Gly Leu Ile Ala Val Asp His Val Val Gly Asn Val Glu Lys
165 170 175

Met Glu Glu Trp Val Ser Tyr Tyr Glu Asn Val Met Gly Phe Lys Gln
180 185 190

Met Ile His Phe Asp Asp Asp Asp Ile Ser Thr Glu Tyr Ser Ala Leu
195 200 205

Met Ser Lys Val Met Thr Asn Gly Ser Arg Ile Lys Phe Pro Ile Asn
210 215 220

Glu Pro Ala Asp Gly Lys Arg Lys Ser Gln Ile Gln Glu Tyr Leu Glu
225 230 235 240

Phe Tyr Asn Gly Ala Gly Val Gln His Leu Ala Leu Leu Thr Ser Asp
245 250 255

Ile Val Lys Thr Val Glu Ala Leu Arg Ala Asn Gly Val Glu Phe Leu
260 265 270

Asp Thr Pro Asp Thr Tyr Tyr Asp Glu Leu Thr Ala Arg Val Gly Lys
275 280 285

Ile Asp Glu Glu Ile Asp Lys Leu Lys Glu Leu Lys Ile Leu Val Asp
290 295 300

Arg Asp Asp Glu Gly Tyr Leu Leu Gln Ile Phe Thr Lys Pro Ile Val
305 310 315 320

Asp Arg Pro Thr Leu Phe Ile Glu Ile Ile Gln Arg Lys Gly Ser Arg
325 330 335

Gly Phe Gly Glu Gly Asn Phe Lys Ala Leu Phe Glu Ser Ile Glu Arg
340 345 350

Glu Gln Glu Arg Arg Gly Asn Leu
355 360

<210> SEQ ID NO 13
<211> LENGTH: 1122
<212> TYPE: DNA
<213> ORGANISM: Artificial
<220> FEATURE:
<223> OTHER INFORMATION: Polynucleotide Sequence encoding modified Bacillus Thuringiensis HPPD

<400> SEQUENCE: 13
atggctaagc agaagtctat ggacaccctt gctgcacaga tggaagactt cttcccagtg 60
agggacgtag accacttgga gttctacgtt ggcaacgcta agcaatccag ctactatctc 120
gcgagggcat tcgggttcaa gattgttgca tactcaggat tggagacagg caaccgtgag 180
aaggtgtcct atgttctggt ccagaagaac atgcgctttg tggtgagtgg agctctgtcc 240
agtgagaatc gtatcgcaga gtttgtcaag actcatggag atggtgtcaa agatgtggct 300
ttgcttgttg atgacgttga taaggcatac tctgaagctg tcaaacgtgg agctgttgcc 360
atagcaccac ctcaagagtt gaccgatgag gatggtacgt tgaagaaggc tgttatcggc 420
acttatggtg ataccataca cacgctcgtt gaacgcaaga attacaaagg agctttcatg 480
ccagggttcc agaaggtgga gtttaacatt ccatttgagg aatctgggct catcgcagtt 540
gaccatgtgg ttgggaacgt tgagaagatg gaggaatggg ttagttacta tgagaatgtc 600
atgggcttca aacagatgat ccacttcgac gatgacgata tcagcactga atactctgcc 660
cttatgtcca aagtgatgac taacgggtct aggatcaaat tccctatcaa cgagccagca 720
gatggcaaac gcaagagcca aattcaggaa tacctcgagt tctacaacgg tgccggagtg 780
caacacttgg ctcttctcac aagcgacatt gtgaagaccg tggaagccct tagagccaac 840

-continued

```
ggtgtggagt tctcgacac acctgacacc tactacgacg aactaaccgc cagagtggga    900
aagattgacg aagagattga caaactcaag gaacttaaga ttctcgtgga cagagacgat    960
gaaggatacc tgctccaaat ctttaccaag cctattgtgg acagacccac cctgtttatc   1020
gagattattc aacgaaaggg ttcaagaggt ttcggagagg gaaacttcaa agccctattc   1080
gagagcatag aacgagaaca agagcgcaga ggcaacctgt ga                      1122
```

<210> SEQ ID NO 14
<211> LENGTH: 373
<212> TYPE: PRT
<213> ORGANISM: Artificial
<220> FEATURE:
<223> OTHER INFORMATION: Modified Bacillus Thuringiensis HPPD
      polypeptide

<400> SEQUENCE: 14

```
Met Ala Lys Gln Lys Ser Met Asp Thr Leu Ala Ala Gln Met Glu Asp
  1               5                  10                  15

Phe Phe Pro Val Arg Asp Val Asp His Leu Glu Phe Tyr Val Gly Asn
                 20                  25                  30

Ala Lys Gln Ser Ser Tyr Tyr Leu Ala Arg Ala Phe Gly Phe Lys Ile
             35                  40                  45

Val Ala Tyr Ser Gly Leu Glu Thr Gly Asn Arg Glu Lys Val Ser Tyr
 50                  55                  60

Val Leu Val Gln Lys Asn Met Arg Phe Val Val Ser Gly Ala Leu Ser
 65                  70                  75                  80

Ser Glu Asn Arg Ile Ala Glu Phe Val Lys Thr His Gly Asp Gly Val
                 85                  90                  95

Lys Asp Val Ala Leu Leu Val Asp Val Asp Lys Ala Tyr Ser Glu
            100                 105                 110

Ala Val Lys Arg Gly Ala Val Ala Ile Ala Pro Pro Gln Glu Leu Thr
            115                 120                 125

Asp Glu Asp Gly Thr Leu Lys Lys Ala Val Ile Gly Thr Tyr Gly Asp
130                 135                 140

Thr Ile His Thr Leu Val Glu Arg Lys Asn Tyr Lys Gly Ala Phe Met
145                 150                 155                 160

Pro Gly Phe Gln Lys Val Glu Phe Asn Ile Pro Phe Glu Glu Ser Gly
                165                 170                 175

Leu Ile Ala Val Asp His Val Val Gly Asn Val Glu Lys Met Glu Glu
            180                 185                 190

Trp Val Ser Tyr Tyr Glu Asn Val Met Gly Phe Lys Gln Met Ile His
            195                 200                 205

Phe Asp Asp Asp Ile Ser Thr Glu Tyr Ser Ala Leu Met Ser Lys
210                 215                 220

Val Met Thr Asn Gly Ser Arg Ile Lys Phe Pro Ile Asn Glu Pro Ala
225                 230                 235                 240

Asp Gly Lys Arg Lys Ser Gln Ile Gln Glu Tyr Leu Glu Phe Tyr Asn
                245                 250                 255

Gly Ala Gly Val Gln His Leu Ala Leu Leu Thr Ser Asp Ile Val Lys
            260                 265                 270

Thr Val Glu Ala Leu Arg Ala Asn Gly Val Glu Phe Leu Asp Thr Pro
            275                 280                 285

Asp Thr Tyr Tyr Asp Glu Leu Thr Ala Arg Val Gly Lys Ile Asp Glu
        290                 295                 300
```

| Glu | Ile | Asp | Lys | Leu | Lys | Glu | Leu | Lys | Ile | Leu | Val | Asp | Arg | Asp | Asp |
|---|---|---|---|---|---|---|---|---|---|---|---|---|---|---|---|
| 305 | | | | 310 | | | | 315 | | | | 320 | | | |

| Glu | Gly | Tyr | Leu | Leu | Gln | Ile | Phe | Thr | Lys | Pro | Ile | Val | Asp | Arg | Pro |
|---|---|---|---|---|---|---|---|---|---|---|---|---|---|---|---|
| | | | 325 | | | | | 330 | | | | 335 | | | |

| Thr | Leu | Phe | Ile | Glu | Ile | Ile | Gln | Arg | Lys | Gly | Ser | Arg | Gly | Phe | Gly |
|---|---|---|---|---|---|---|---|---|---|---|---|---|---|---|---|
| | | | 340 | | | | 345 | | | | | 350 | | | |

| Glu | Gly | Asn | Phe | Lys | Ala | Leu | Phe | Glu | Ser | Ile | Glu | Arg | Glu | Gln | Glu |
|---|---|---|---|---|---|---|---|---|---|---|---|---|---|---|---|
| | | 355 | | | | 360 | | | | 365 | | | | | |

| Arg | Arg | Gly | Asn | Leu |
|---|---|---|---|---|
| 370 | | | | |

<210> SEQ ID NO 15
<211> LENGTH: 1489
<212> TYPE: DNA
<213> ORGANISM: Gossypium hirsutum

<400> SEQUENCE: 15

```
gtcgacccac gcgtccgcac cccacccgac ccctaaaaat ggtccagaca aaccagtccg      60
gttccggcaa tgatttcaag ctcgtcggat tctcgaattt cgtccggtcc aatccgaaat     120
ccgatcggtt caccgtcaaa cgtttccacc acatcgagtt ttggtgtacc gacgccacta     180
acgtcgctcg ccgttttca tggggtctcg gtatgcaatt tgtagctaaa tcggatttat      240
ccaccggaaa tttgacccat gcttcttatc tcctccgttc cggtgacctg aacttccttt     300
tcactgcccc ttattcccct tctatcgccg ttgctcaaaa cctctcccct caatctaccg     360
cttccatccc ttcttttgat cattcactct gccgctcctt cgctgccacc cacggcttag     420
gcgttcgcgc catcgccatc gaagtcgacg acgccgaaac cgctttcacc accagtgtca     480
cacacgcgcg gttacccttt tccctccta ccccactcgg cgacgtcgcc accatcgccg      540
aagtcaaaact ctatggcgac gtcgttttgc gttacgtcag ttacaccacc accataaaact   600
ccgaccatga tttctcgccg ggattcgaga aaatcgaaga cgccctttct taccctttag     660
attacggact ccgacgactc gaccacgccg ttggaaacgt cccagaactc ggtcccgctg     720
tttcgtacgt caaatccttc accggcttcc acgaattcgc tgaattcaca gctgaagacg     780
tcggaactag cgaaagtgga ctaaactccg tcgttttagc taacaacgaa gaaatggtat     840
tacttccgat gaacgaaccg gtgttcggaa caaaaggaa aagccaaatc caaacgtatt      900
tagaacacaa cgaaggtgcc ggagttcaac atttggcatt ggtgagtgaa gatatattca     960
agacgttaag agaaatgagg aagagaagct tcgtcggcgg ttttgagttc atgccgtcgc    1020
cgccgccgac ttattataaa aaattgaagc aaagggcagg ggatattttg agtgatgaac    1080
agattaaaga gtgtgaagaa ctggggattt tggttgatag agatgatcaa gggactttgc    1140
tgcaaatttt cactaagcca gttggtgata ggccaaccat cttcatagag ataatacaaa    1200
gaattgggtg cctggtgaag gatgaagaag gaaagcaata ccaaaaaggt ggatgtggtg    1260
gttttgggaa aggcaacttt tctgagctct tcaaatccat tgaagaatat gagaaatctc    1320
ttgaagccaa acagtcccag aatccatgac ttgattgaaa taaaaaaaaa ggggggcttc    1380
ttcttgctat atataaaact ttatgttacc catgttattc gaatttgaat ataaatatct    1440
aattgacata gttttgttt tttgaaaaaa aaaaaaaag gcggccgc                   1489
```

<210> SEQ ID NO 16
<211> LENGTH: 436
<212> TYPE: PRT
<213> ORGANISM: Gossypium hirsutum

<400> SEQUENCE: 16

```
Met Val Gln Thr Asn Gln Ser Gly Ser Gly Asn Asp Phe Lys Leu Val
1               5                   10                  15

Gly Phe Ser Asn Phe Val Arg Ser Asn Pro Lys Ser Asp Arg Phe Thr
            20                  25                  30

Val Lys Arg Phe His His Ile Glu Phe Trp Cys Thr Asp Ala Thr Asn
        35                  40                  45

Val Ala Arg Arg Phe Ser Trp Gly Leu Gly Met Gln Phe Val Ala Lys
    50                  55                  60

Ser Asp Leu Ser Thr Gly Asn Leu Thr His Ala Ser Tyr Leu Leu Arg
65                  70                  75                  80

Ser Gly Asp Leu Asn Phe Leu Phe Thr Ala Pro Tyr Ser Pro Ser Ile
                85                  90                  95

Ala Val Ala Gln Asn Leu Ser Pro Gln Ser Thr Ala Ser Ile Pro Ser
            100                 105                 110

Phe Asp His Ser Leu Cys Arg Ser Phe Ala Ala Thr His Gly Leu Gly
        115                 120                 125

Val Arg Ala Ile Ala Ile Glu Val Asp Asp Ala Glu Thr Ala Phe Thr
    130                 135                 140

Thr Ser Val Thr His Gly Ala Leu Pro Phe Ser Pro Pro Thr Pro Leu
145                 150                 155                 160

Gly Asp Val Ala Thr Ile Ala Glu Val Lys Leu Tyr Gly Asp Val Val
                165                 170                 175

Leu Arg Tyr Val Ser Tyr Thr Thr Thr Ile Asn Ser Asp His Asp Phe
            180                 185                 190

Ser Pro Gly Phe Glu Lys Ile Glu Asp Ala Leu Ser Tyr Pro Leu Asp
        195                 200                 205

Tyr Gly Leu Arg Arg Leu Asp His Ala Val Gly Asn Val Pro Glu Leu
    210                 215                 220

Gly Pro Ala Val Ser Tyr Val Lys Ser Phe Thr Gly Phe His Glu Phe
225                 230                 235                 240

Ala Glu Phe Thr Ala Glu Asp Val Gly Thr Ser Glu Ser Gly Leu Asn
                245                 250                 255

Ser Val Val Leu Ala Asn Asn Glu Glu Met Val Leu Leu Pro Met Asn
            260                 265                 270

Glu Pro Val Phe Gly Thr Lys Arg Lys Ser Gln Ile Gln Thr Tyr Leu
        275                 280                 285

Glu His Asn Glu Gly Ala Gly Val Gln His Leu Ala Leu Val Ser Glu
    290                 295                 300

Asp Ile Phe Lys Thr Leu Arg Glu Met Arg Lys Arg Ser Phe Val Gly
305                 310                 315                 320

Gly Phe Glu Phe Met Pro Ser Pro Pro Thr Tyr Tyr Lys Lys Leu
                325                 330                 335

Lys Gln Arg Ala Gly Asp Ile Leu Ser Asp Glu Gln Ile Lys Glu Cys
            340                 345                 350

Glu Glu Leu Gly Ile Leu Val Asp Arg Asp Asp Gln Gly Thr Leu Leu
        355                 360                 365

Gln Ile Phe Thr Lys Pro Val Gly Asp Arg Pro Thr Ile Phe Ile Glu
    370                 375                 380

Ile Ile Gln Arg Ile Gly Cys Leu Val Lys Asp Glu Glu Gly Lys Gln
385                 390                 395                 400

Tyr Gln Lys Gly Gly Cys Gly Gly Phe Gly Lys Gly Asn Phe Ser Glu
                405                 410                 415
```

Leu Phe Lys Ser Ile Glu Glu Tyr Glu Lys Ser Leu Glu Ala Lys Gln
        420                 425                 430

Ser Gln Asn Pro
        435

<210> SEQ ID NO 17
<211> LENGTH: 1527
<212> TYPE: DNA
<213> ORGANISM: Gossypium hirsutum

<400> SEQUENCE: 17

| | | | | | | |
|---|---|---|---|---|---|---|
| gtcgacccac | gcgtccgctc | aacggcaaca | cccgaccaga | cccgaaaaaa | tggtccagac | 60 |
| aaaccagtct | ggttccggca | atgatttcaa | gctcgtcgga | ttctcgaatt | tcgtccggtc | 120 |
| aaatccaaaa | tccgatcggt | tcaccgtcaa | acgtttccac | cacatcgagt | tttggtgtac | 180 |
| cgacgccact | aacgtcgctc | gccgtttttc | atgggggtctc | ggtatgcaat | ttgtagctaa | 240 |
| atcggattta | tccaccggaa | atttgaccca | tgcttcttat | ctcctccgtt | cccgtgacct | 300 |
| gaacttcctt | tcactgccc | cctattcccc | ttctattgcc | gttgctcaaa | acctctcccc | 360 |
| tcaatccacc | gcttcgatcc | cttcttttga | tcattcactc | tgccgctcct | tcgctgccac | 420 |
| ccacggctta | ggcgttcgcg | ccatcgccat | cgaagttgac | gatgccgaaa | ccgctttcac | 480 |
| caccagtgtc | acacatggcg | cgttacccctt | ttgccctcct | accccactcg | gcgacgtcgc | 540 |
| cactatcgcc | gaagtcaaac | tctacggcga | cgtcgttttg | cgttacgtca | gttacaccac | 600 |
| caccataaac | tccgaccatg | atttcttgcc | gggattcgag | aaaatagaag | acacccttc | 660 |
| ttacccttta | gattacggac | tccgacgact | cgaccacgcc | gtcggcaacg | tcccagaact | 720 |
| cggtcccgct | gtttcgtacg | ttaaatcctt | caccggcttc | cacgaattcg | ctgaattcac | 780 |
| agctgaagac | gtcggaacta | gcgaaagtgg | actaaactcc | gtcgttttag | ctaacaacga | 840 |
| agaaatggta | ttacttccga | tgaacgaacc | ggtgttcgga | acaaaaagga | aaagccaaat | 900 |
| ccaaacgtat | ttagaacaca | cgaaggtgc | cggagttcaa | catttggcat | tggtgagtga | 960 |
| agatatattc | aagacgttaa | gagaaatgag | gaagagaagc | ttcgtcggcg | gttttgagtt | 1020 |
| catgccgtcg | ccgccgccga | cttattataa | aaaattgaag | caaagggcag | gggatatttt | 1080 |
| gagtgatgaa | cagattaaag | agtgtgaaga | actggggatt | ctggttgata | gagatgatca | 1140 |
| agggactttg | ctgcaaattt | tcactaagcc | agttggtgat | aggccaacca | tcttcataga | 1200 |
| gataatacaa | agaattgggt | gcatggtgaa | ggatgaagaa | ggaaagcaat | accaaaaagg | 1260 |
| tggatgtggt | ggttttggga | aaggcaactt | ttctgagctc | ttcaaatcca | ttgaagaata | 1320 |
| tgagaaatct | cttgaagcca | aacaatctca | gaatccatga | cttgattgaa | aaagaaaaa | 1380 |
| gaaaaaaggc | ttcttcttgc | tttatataaa | actttatgtt | acctatgtta | ttcaaatttg | 1440 |
| aatataaata | tcttataaac | ataattttg | tttttgaat | aatttttatta | taggttttga | 1500 |
| ttaaaaaaaa | aaaaaaggg | cggccgc | | | | 1527 |

<210> SEQ ID NO 18
<211> LENGTH: 436
<212> TYPE: PRT
<213> ORGANISM: Gossypium hirsutum

<400> SEQUENCE: 18

Met Val Gln Thr Asn Gln Ser Gly Ser Gly Asn Asp Phe Lys Leu Val
1               5                   10                  15

Gly Phe Ser Asn Phe Val Arg Ser Asn Pro Lys Ser Asp Arg Phe Thr

```
                    20                  25                  30
Val Lys Arg Phe His His Ile Glu Phe Trp Cys Thr Asp Ala Thr Asn
             35                  40                  45
Val Ala Arg Arg Phe Ser Trp Gly Leu Gly Met Gln Phe Val Ala Lys
         50                  55                  60
Ser Asp Leu Ser Thr Gly Asn Leu Thr His Ala Ser Tyr Leu Leu Arg
 65                  70                  75                  80
Ser Arg Asp Leu Asn Phe Leu Phe Thr Ala Pro Tyr Ser Pro Ser Ile
                 85                  90                  95
Ala Val Ala Gln Asn Leu Ser Pro Gln Ser Thr Ala Ser Ile Pro Ser
            100                 105                 110
Phe Asp His Ser Leu Cys Arg Ser Phe Ala Ala Thr His Gly Leu Gly
            115                 120                 125
Val Arg Ala Ile Ala Ile Glu Val Asp Asp Ala Glu Thr Ala Phe Thr
        130                 135                 140
Thr Ser Val Thr His Gly Ala Leu Pro Phe Cys Pro Pro Thr Pro Leu
145                 150                 155                 160
Gly Asp Val Ala Thr Ile Ala Glu Val Lys Leu Tyr Gly Asp Val Val
                165                 170                 175
Leu Arg Tyr Val Ser Tyr Thr Thr Ile Asn Ser Asp His Asp Phe
            180                 185                 190
Leu Pro Gly Phe Glu Lys Ile Glu Asp Thr Leu Ser Tyr Pro Leu Asp
            195                 200                 205
Tyr Gly Leu Arg Arg Leu Asp His Ala Val Gly Asn Val Pro Glu Leu
    210                 215                 220
Gly Pro Ala Val Ser Tyr Val Lys Ser Phe Thr Gly Phe His Glu Phe
225                 230                 235                 240
Ala Glu Phe Thr Ala Glu Asp Val Gly Thr Ser Glu Ser Gly Leu Asn
                245                 250                 255
Ser Val Val Leu Ala Asn Asn Glu Glu Met Val Leu Leu Pro Met Asn
            260                 265                 270
Glu Pro Val Phe Gly Thr Lys Arg Lys Ser Gln Ile Gln Thr Tyr Leu
        275                 280                 285
Glu His Asn Glu Gly Ala Gly Val Gln His Leu Ala Leu Val Ser Glu
    290                 295                 300
Asp Ile Phe Lys Thr Leu Arg Glu Met Arg Lys Arg Ser Phe Val Gly
305                 310                 315                 320
Gly Phe Glu Phe Met Pro Ser Pro Pro Thr Tyr Tyr Lys Lys Leu
                325                 330                 335
Lys Gln Arg Ala Gly Asp Ile Leu Ser Asp Glu Gln Ile Lys Glu Cys
            340                 345                 350
Glu Glu Leu Gly Ile Leu Val Asp Arg Asp Gln Gly Thr Leu Leu
        355                 360                 365
Gln Ile Phe Thr Lys Pro Val Gly Asp Arg Pro Thr Ile Phe Ile Glu
    370                 375                 380
Ile Ile Gln Arg Ile Gly Cys Met Val Lys Asp Glu Glu Gly Lys Gln
385                 390                 395                 400
Tyr Gln Lys Gly Gly Cys Gly Gly Phe Gly Lys Gly Asn Phe Ser Glu
                405                 410                 415
Leu Phe Lys Ser Ile Glu Glu Tyr Glu Lys Ser Leu Glu Ala Lys Gln
            420                 425                 430
Ser Gln Asn Pro
            435
```

<210> SEQ ID NO 19
<211> LENGTH: 1479
<212> TYPE: DNA
<213> ORGANISM: Brassica napus

<400> SEQUENCE: 19

| | | |
|---|---|---|
| gtcgacccac gcgtccgaaa ctctatgggg cacgaaaacg ccgccgtttg cgaaactcag | 60 |
| cagcacgacg acgctgcgtc gcctggattc aagctcgtcg gattctccaa gttcgtgagg | 120 |
| aagaatccaa agtccgacaa gttcaaggta agcgcttcc accacatcga gttctggtgc | 180 |
| ggggacgcca ccaacgtctc ccgccgcttc tcgtggggac taggcatgcg attctccgcc | 240 |
| aaatccgatc tctccaccgg aaacatggtt cacgcctcct acctactcac ctccggcgac | 300 |
| ctccgattcc tcttcaccgc tccctactct ccctctctct ccgccggcga agctcaaccg | 360 |
| tccgctacag cctcaatccc atcgttcgat cacgcttctt gccgctcctt cttctcttcg | 420 |
| cacggactcg gcgtgagagc cgtagcgatc gaagtcgaag acgctgagtc agcattctca | 480 |
| atcagcgtag caaacggcgc cgttccttcc tccctccta acgtcctcaa cggagccgtt | 540 |
| acgatcgcgg aagttaaact atacggagac gtcgtcctcc gttacgttag ttattataac | 600 |
| ggaaccgtta gtttcctccc cggatttgaa tctgttgacg atacgtcgtc gtttccgcta | 660 |
| gattacggta tacgccgtct cgaccacgcg gtgggaaacg tccccgagct cggcccagct | 720 |
| ttaacttacc tcgcggggtt caccggcttc caccagttcg cggagttcac tgcagacgac | 780 |
| gtgggaacag ccgagagcgt attgaactcg gctgtgctag ccaacaacga cgagatggtt | 840 |
| ctgttgccga taaacgagcc ggttcacggg acgaagagga agagccagat ccagacgttt | 900 |
| cttgagcaca cgaaggagc cgggctgcag catttggctc tgatgagcga agatatattc | 960 |
| aggacgctga gggagatgag gaagaggagc ggcgttggag ggttcgactt catgccttct | 1020 |
| cctccgccta cttattacaa gaatctcaag aaaaggggttg gagatgtgct tagtgaggag | 1080 |
| cagattgagg agtgtgagga gttggggatt cttgtggata gagatgatca ggggacgttg | 1140 |
| cttcagatct ttacgaaacc acttggtgac aggccgacga tatttataga gataatacag | 1200 |
| agagtgggat gcatgaagag agatgaggaa gggaaggttt accagagtgg aggatgtggt | 1260 |
| gggtttggta aggtaacttt ctctgagctc tttaagtcta ttgaagagta tgagaagaca | 1320 |
| cttgaagcca aacagcttgt gggttgaatg aagaagaaga agaaccaaac taaaaggatt | 1380 |
| gtaattgata tgtaaaactg ttttatgtta tacaaaatag taaacgatga ttacagaaat | 1440 |
| gtcttctcat cacaaaaaaa aaaaaaaaag ggcggccgc | 1479 |

<210> SEQ ID NO 20
<211> LENGTH: 440
<212> TYPE: PRT
<213> ORGANISM: Brassica napus

<400> SEQUENCE: 20

Met Gly His Glu Asn Ala Ala Val Cys Glu Thr Gln Gln His Asp Asp
1               5                   10                  15

Ala Ala Ser Pro Gly Phe Lys Leu Val Gly Phe Ser Lys Phe Val Arg
            20                  25                  30

Lys Asn Pro Lys Ser Asp Lys Phe Lys Val Lys Arg Phe His His Ile
        35                  40                  45

Glu Phe Trp Cys Gly Asp Ala Thr Asn Val Ser Arg Arg Phe Ser Trp
    50                  55                  60

```
Gly Leu Gly Met Arg Phe Ser Ala Lys Ser Asp Leu Ser Thr Gly Asn
 65                  70                  75                  80

Met Val His Ala Ser Tyr Leu Leu Thr Ser Gly Asp Leu Arg Phe Leu
                 85                  90                  95

Phe Thr Ala Pro Tyr Ser Pro Ser Leu Ser Ala Gly Glu Ala Gln Pro
            100                 105                 110

Ser Ala Thr Ala Ser Ile Pro Ser Phe Asp His Ala Ser Cys Arg Ser
            115                 120                 125

Phe Phe Ser Ser His Gly Leu Gly Val Arg Ala Val Ala Ile Glu Val
    130                 135                 140

Glu Asp Ala Glu Ser Ala Phe Ser Ile Ser Val Ala Asn Gly Ala Val
145                 150                 155                 160

Pro Ser Ser Pro Pro Asn Val Leu Asn Gly Ala Val Thr Ile Ala Glu
                165                 170                 175

Val Lys Leu Tyr Gly Asp Val Val Leu Arg Tyr Val Ser Tyr Tyr Asn
            180                 185                 190

Gly Thr Val Ser Phe Leu Pro Gly Phe Glu Ser Val Asp Asp Thr Ser
            195                 200                 205

Ser Phe Pro Leu Asp Tyr Gly Ile Arg Arg Leu Asp His Ala Val Gly
    210                 215                 220

Asn Val Pro Glu Leu Gly Pro Ala Leu Thr Tyr Leu Ala Gly Phe Thr
225                 230                 235                 240

Gly Phe His Gln Phe Ala Glu Phe Thr Ala Asp Asp Val Gly Thr Ala
                245                 250                 255

Glu Ser Val Leu Asn Ser Ala Val Leu Ala Asn Asn Asp Glu Met Val
            260                 265                 270

Leu Leu Pro Ile Asn Glu Pro Val His Gly Thr Lys Arg Lys Ser Gln
            275                 280                 285

Ile Gln Thr Phe Leu Glu His Asn Glu Gly Ala Gly Leu Gln His Leu
    290                 295                 300

Ala Leu Met Ser Glu Asp Ile Phe Arg Thr Leu Arg Glu Met Arg Lys
305                 310                 315                 320

Arg Ser Gly Val Gly Gly Phe Asp Phe Met Pro Ser Pro Pro Pro Thr
                325                 330                 335

Tyr Tyr Lys Asn Leu Lys Lys Arg Val Gly Asp Val Leu Ser Glu Glu
            340                 345                 350

Gln Ile Glu Glu Cys Glu Glu Leu Gly Ile Leu Val Asp Arg Asp Asp
            355                 360                 365

Gln Gly Thr Leu Leu Gln Ile Phe Thr Lys Pro Leu Gly Asp Arg Pro
    370                 375                 380

Thr Ile Phe Ile Glu Ile Ile Gln Arg Val Gly Cys Met Lys Arg Asp
385                 390                 395                 400

Glu Glu Gly Lys Val Tyr Gln Ser Gly Gly Cys Gly Gly Phe Gly Lys
                405                 410                 415

Gly Asn Phe Ser Glu Leu Phe Lys Ser Ile Glu Glu Tyr Glu Lys Thr
            420                 425                 430

Leu Glu Ala Lys Gln Leu Val Gly
            435                 440

<210> SEQ ID NO 21
<211> LENGTH: 1495
<212> TYPE: DNA
<213> ORGANISM: Lycopersicon esculentum

<400> SEQUENCE: 21
```

```
aaagaattcg gcacgagcac agatacaacc ggcgctacct tcaagctagt tggcttcaat      60
aatttcatcc gtgctaatcc ccgttccgat ttcttctccg taaaacgctt ccaccatatc     120
gaattctggt gcggcgatgc aaccaataca tctcgtcgtt tctcttggtc tcttggcatg     180
ccgattacag caaaatcaga cctctccacc ggaaattcag ttcatgcgtc gtatctcctc     240
cgttctgttt caggcgaact tcaatttgtt ttcactgctc cttattcgcc gtcaatttca     300
gtaccgtcaa cggcaggtat acctagtttt tccaccccta cttatcggga ttttacggcg     360
aagcatggtc ttggtgttcg tgctgttgcg ttggaggtgg agaacgctta cctggcgttc     420
tccgctagtg tggctcgtgg ggcgaaaccc cggtttgaac ctgtaacgat tgatgagcat     480
gtggctgttg ctgaagttca tctatatggc gatgtcgttt tgcggtttgt gagtcttgtt     540
aaagatgcgg ataccctcat tttcctacca ggttttgagg ccatggatga acatcatca      600 ttcaaggaac tggattatgg gattcaccga ctggaccatg ccgttgggaa tgtgccggag     660
ttgggtcctg tagtggacta catcaaggca tttacggggt tcatgaatt tgcggagttt      720 acagctgaag atgttggaac tgctgagagc gggctgaact cagttgtgtt ggcaaacaat     780
gacgagacag tattgcttcc gttgaatgag ccggtatatg aactaaaag gaagagtcaa      840 attcagactt atttagagca taatgaaggg gcaggagtgc aacatttagc tttggttact     900
gaggatatat tcagaacatt gagggaaatg tggaaaagga gtggagttgg gggatttgaa     960
ttcatgcctg cacctccgcc tactattat aagaatttga gaagtagggc cggggatgta     1020
ctcagtgacg aacaaatcca ggcgtgtgaa gaattgggga tcttggttga cagggatgat    1080 cagggactc tgcttcagat atttaccaag cctgtgggag acaggccaac aatatttata     1140
gaaataattc agagaatcgg gtgcatgctc aaagatgaaa aaggacaagt ctatcagaag    1200
ggcggttgtg gaggcttcgg taagggaaac ttctctgagc tgtttagatc gatcgaggaa    1260
tacgagaaga tgcttgaagc caaacatgtt aatcaagtag ctgctgtcga atgaatatat    1320
acgagcatta gcttgcaatc taattgaaat ttgaaggggg catctaagct tccatttgat    1380 cttttctacaa ttaattatga aataaaaaat agctgttgtg taaatagcat ggagggaaac    1440
aaagtcaagt aatttaagta taatgttgat cataaaaaaa aaaaaaaaaa aaaac          1495
```

<210> SEQ ID NO 22
<211> LENGTH: 437
<212> TYPE: PRT
<213> ORGANISM: Lycopersicon esculentum

<400> SEQUENCE: 22

```
Lys Glu Phe Gly Thr Ser Thr Asp Thr Thr Gly Ala Thr Phe Lys Leu
1               5                   10                  15

Val Gly Phe Asn Asn Phe Ile Arg Ala Asn Pro Arg Ser Asp Phe Phe
            20                  25                  30

Ser Val Lys Arg Phe His His Ile Glu Phe Trp Cys Gly Asp Ala Thr
        35                  40                  45

Asn Thr Ser Arg Arg Phe Ser Trp Ser Leu Gly Met Pro Ile Thr Ala
    50                  55                  60

Lys Ser Asp Leu Ser Thr Gly Asn Ser Val His Ala Ser Tyr Leu Leu
65                  70                  75                  80

Arg Ser Val Ser Gly Glu Leu Gln Phe Val Phe Thr Ala Pro Tyr Ser
                85                  90                  95

Pro Ser Ile Ser Val Pro Ser Thr Ala Gly Ile Pro Ser Phe Ser Thr
            100                 105                 110
```

-continued

```
Pro Thr Tyr Arg Asp Phe Thr Ala Lys His Gly Leu Gly Val Arg Ala
        115                 120                 125
Val Ala Leu Glu Val Glu Asn Ala Tyr Leu Ala Phe Ser Ala Ser Val
    130                 135                 140
Ala Arg Gly Ala Lys Pro Arg Phe Glu Pro Val Thr Ile Asp Glu His
145                 150                 155                 160
Val Ala Val Ala Glu Val His Leu Tyr Gly Asp Val Val Leu Arg Phe
                165                 170                 175
Val Ser Leu Val Lys Asp Ala Asp Thr Leu Ile Phe Leu Pro Gly Phe
            180                 185                 190
Glu Ala Met Asp Glu Thr Ser Ser Phe Lys Glu Leu Asp Tyr Gly Ile
        195                 200                 205
His Arg Leu Asp His Ala Val Gly Asn Val Pro Glu Leu Gly Pro Val
    210                 215                 220
Val Asp Tyr Ile Lys Ala Phe Thr Gly Phe His Glu Phe Ala Glu Phe
225                 230                 235                 240
Thr Ala Glu Asp Val Gly Thr Ala Glu Ser Gly Leu Asn Ser Val Val
                245                 250                 255
Leu Ala Asn Asn Asp Glu Thr Val Leu Leu Pro Leu Asn Glu Pro Val
            260                 265                 270
Tyr Gly Thr Lys Arg Lys Ser Gln Ile Gln Thr Tyr Leu Glu His Asn
        275                 280                 285
Glu Gly Ala Gly Val Gln His Leu Ala Leu Val Thr Glu Asp Ile Phe
    290                 295                 300
Arg Thr Leu Arg Glu Met Trp Lys Arg Ser Gly Val Gly Gly Phe Glu
305                 310                 315                 320
Phe Met Pro Ala Pro Pro Thr Tyr Tyr Lys Asn Leu Arg Ser Arg
                325                 330                 335
Ala Gly Asp Val Leu Ser Asp Glu Gln Ile Gln Ala Cys Glu Glu Leu
            340                 345                 350
Gly Ile Leu Val Asp Arg Asp Gln Gly Thr Leu Leu Gln Ile Phe
        355                 360                 365
Thr Lys Pro Val Gly Asp Arg Pro Thr Ile Phe Ile Glu Ile Ile Gln
    370                 375                 380
Arg Ile Gly Cys Met Leu Lys Asp Glu Lys Gly Gln Val Tyr Gln Lys
385                 390                 395                 400
Gly Gly Cys Gly Gly Phe Gly Lys Gly Asn Phe Ser Glu Leu Phe Arg
                405                 410                 415
Ser Ile Glu Glu Tyr Glu Lys Met Leu Glu Ala Lys His Val Asn Gln
            420                 425                 430
Val Ala Ala Val Glu
        435
```

<210> SEQ ID NO 23
<211> LENGTH: 1202
<212> TYPE: DNA
<213> ORGANISM: Sphingomonas elodea

<400> SEQUENCE: 23

```
gctctaaggg cttcgagttc gtcgagttca cctcgcccga tccggacgcg atggcgcgcc    60
agttcgagca gctgggcttc gttgccagcc accgccaccc gcgcaagaac atcacgcgct   120
acaagcaggg ccgcatcaac ctgatgctca accgcgacga tgccggccgc gtcgccgcct   180
tccgcggcga gcatggccct tcggccagcg cgatggcgtt ccgcgtagcg gacccgaaaa   240
```

```
aggcgatgga atggcgctc gcccacggcg ccaagcctac ggacgaggac gacaccgtca    300
tccagggcat cggcggctcc tatctctatt tcatccagga cgagatcgac ctctatgccg    360
actgggccga gttccccggc tggcgcgagg cagaggcggc gaacagcgtc gggctcgacc    420
tgctcgacca cctcacccac aatgtccgcc gcggccagat gcgggtgtgg agcgaattct    480
accgcacgct cttcggcttc gaggagcaga agtatttcga catcaaggcg aaggcgaccg    540
gcctgttcag ccaggcgatg atcgcgcccg acaaggcgat ccgcatcccg ctgaacgaga    600
gccaggacga cgccagccag atcgaggaat tcatccgcga atacaacggc gaaggcatcc    660
agcacctcgc gctgaccacg gacgacatct acgacacggt cgagcgcctg cgcgcccgcg    720
gcgtgcggct gcaggacacg atcgagacct attacgagct ggtcgacaag cgtgtccccg    780
gccacggcga ggacctcgag cggctgcgca gaaccgcat cttgatcgac ggttcggtag    840
agaatgacga gggcatcctg ctccagatct tcaccgagac gatgttcggg ccgatcttct    900
tcgagatcat ccagcgcaag ggcaatgaag gcttcggcaa cggcaatttc caggcgctgt    960
tcgagagcat cgagctcgac cagatccgcc gcggcgtgat caaggtcgac gcctgacgag   1020
ttcggagagg gagagagccg ggggtgccgt cgcaggaaca gtggcatacc ccggccccac   1080
cgaacgtccc ccctcccctt tcgatcgaca aggggagtcg tgctggagag gacgagcctt   1140
gtgaccacct atttccccgg cttcggcaac catgtctcca ccgaagcggt gcccggcgcg   1200
ct                                                                  1202
```

<210> SEQ ID NO 24
<211> LENGTH: 337
<212> TYPE: PRT
<213> ORGANISM: Sphingomonas elodea

<400> SEQUENCE: 24

```
Ser Lys Gly Phe Glu Phe Val Glu Phe Thr Ser Pro Asp Pro Asp Ala
 1               5                  10                  15

Met Ala Arg Gln Phe Glu Gln Leu Gly Phe Val Ala Ser His Arg His
                20                  25                  30

Pro Arg Lys Asn Ile Thr Arg Tyr Lys Gln Gly Arg Ile Asn Leu Met
            35                  40                  45

Leu Asn Arg Asp Asp Ala Gly Arg Val Ala Ala Phe Arg Gly Glu His
        50                  55                  60

Gly Pro Ser Ala Ser Ala Met Ala Phe Arg Val Ala Asp Pro Lys Lys
 65                 70                  75                  80

Ala Met Glu Trp Ala Leu Ala His Gly Ala Lys Pro Thr Asp Glu Asp
                85                  90                  95

Asp Thr Val Ile Gln Gly Ile Gly Gly Ser Tyr Leu Tyr Phe Ile Gln
               100                 105                 110

Asp Glu Ile Asp Leu Tyr Ala Asp Trp Ala Glu Phe Pro Gly Trp Arg
            115                 120                 125

Glu Ala Glu Ala Ala Asn Ser Val Gly Leu Asp Leu Leu Asp His Leu
        130                 135                 140

Thr His Asn Val Arg Arg Gly Gln Met Arg Val Trp Ser Glu Phe Tyr
145                 150                 155                 160

Arg Thr Leu Phe Gly Phe Glu Glu Gln Lys Tyr Phe Asp Ile Lys Gly
                165                 170                 175

Lys Ala Thr Gly Leu Phe Ser Gln Ala Met Ile Ala Pro Asp Lys Ala
            180                 185                 190
```

```
Ile Arg Ile Pro Leu Asn Glu Ser Gln Asp Asp Ala Ser Gln Ile Glu
        195                 200                 205

Glu Phe Ile Arg Glu Tyr Asn Gly Glu Gly Ile Gln His Leu Ala Leu
    210                 215                 220

Thr Thr Asp Asp Ile Tyr Asp Thr Val Glu Arg Leu Arg Ala Arg Gly
225                 230                 235                 240

Val Arg Leu Gln Asp Thr Ile Glu Thr Tyr Tyr Glu Leu Val Asp Lys
                245                 250                 255

Arg Val Pro Gly His Gly Glu Asp Leu Glu Arg Leu Arg Lys Asn Arg
            260                 265                 270

Ile Leu Ile Asp Gly Ser Val Glu Asn Asp Glu Gly Ile Leu Leu Gln
        275                 280                 285

Ile Phe Thr Glu Thr Met Phe Gly Pro Ile Phe Phe Glu Ile Ile Gln
    290                 295                 300

Arg Lys Gly Asn Glu Gly Phe Gly Asn Gly Asn Phe Gln Ala Leu Phe
305                 310                 315                 320

Glu Ser Ile Glu Leu Asp Gln Ile Arg Arg Gly Val Ile Lys Val Asp
                325                 330                 335

Ala
```

<210> SEQ ID NO 25
<211> LENGTH: 1122
<212> TYPE: DNA
<213> ORGANISM: Erwinia herbicola

<400> SEQUENCE: 25

```
atggtggctg aactgaccgc gttacgcgat caaattgaca gtgtagataa agcgctgctg      60
gatctgctgg ctaagcgact ggaactggtg gccgagtag gtgaggtgaa gagccgttac     120
ggcctgccta tctatgtgcc tgagcgtgag gcgtcgatgc tggcttcgcg tcgcaaagag     180
gccgaagcgc tcggcgtacc accggatctg attgaggatg tgctgcgtcg cgtgatgcgg     240
gaatcctata ccagcgagaa tgataaaggc tttaaaaccc tctgtcctga actgcgcccg     300
gtggtgattg tcggtggtaa gggccagatg ggccggctgt ttgaaaaaat gctcgggcta     360
tcaggctaca cggttaaaac gctggataaa gaggactggc tcaggctga gactctgctc      420
agcgatgccg gaatggtgat cattagcgtg ccgattcacc tgaccgagca ggtgattgcc     480
caactgccac cactgccgga agattgtatt ctggtcgatc tggcgtcagt caaaaaccgg     540
cctctgcagg caatgctggc tgcccataac gggcctgtac tgggtctgca tccgatgttt     600
ggcccggaca gcggcagcct ggcaaaacag gtggtggtct ggtgtgatgg aagacaaccg     660
gaagcgtatc agtggttcct ggagcagatt caggtctggg gtgcgcgtct gcatcgtatc     720
agcgctgttg agcatgacca gaacatggca ttcattcagg cgctgcgtca ctttgctacc     780
ttcgcttatg tctgcatttt agccgaagag aacgtcaatc tggatcagct gctggcgctc     840
tcgtcgccca tttaccggct tgaactggcg atggtggggc ggttgttcgc tcaggatccg     900
caactctatg cggatatcat catgtcttca gagagtaatc tggcgctgat aaaacgctat     960
taccagcggt ttggtgaagc gattgcgctg ctggagcagg gcgacaagca ggcgtttatc    1020
gccagcttta accgggttga acagtggttt ggcgatcacg caaaacgctt cctggtcgaa    1080
agccgaagcc tgttgcgatc ggccaatgac agccgcccat aa                       1122
```

<210> SEQ ID NO 26
<211> LENGTH: 1182
<212> TYPE: DNA

<210> SEQ ID NO 26
<211> LENGTH: 1182
<212> TYPE: DNA
<213> ORGANISM: Arabidopsis thaliana

<400> SEQUENCE: 26

| | | | | | |
|---|---|---|---|---|---|
| atggagtctc | tgctctctag | ttcttctctt | gtttccgctg | ctggtgggtt | ttgttggaag | 60 |
| aagcagaatc | taaagctcca | ctctttatca | gaaatccgag | ttctgcgttg | tgattcgagt | 120 |
| aaagttgtcg | caaaaccgaa | gtttaggaac | aatcttgtta | ggcctgatgg | tcaaggatct | 180 |
| tcattgttgt | tgtatccaaa | acataagtcg | agatttcggg | ttaatgccac | tgcgggtcag | 240 |
| cctgaggctt | tcgactcgaa | tagcaaacag | aagtctttta | gagactcgtt | agatgcgttt | 300 |
| tacaggtttt | ctaggcctca | tacagttatt | ggcacagtgc | ttagcatttt | atctgtatct | 360 |
| ttcttagcag | tagagaaggt | ttctgatata | tctcctttac | ttttcactgg | catcttggag | 420 |
| gctgttgttg | cagctctcat | gatgaacatt | tacatagttg | ggctaaatca | gttgtctgat | 480 |
| gttgaaatag | ataaggttaa | caagccctat | cttccattgg | catcaggaga | atattctgtt | 540 |
| aacaccggca | ttgcaatagt | agcttccttc | tccatcatga | gtttctggct | tgggtggatt | 600 |
| gttggttcat | ggccattgtt | ctgggctctt | tttgtgagtt | tcatgctcgg | tactgcatac | 660 |
| tctatcaatt | tgccactttt | acggtggaaa | agatttgcat | tggttgcagc | aatgtgtatc | 720 |
| ctcgctgtcc | gagctattat | tgttcaaatc | gccttttatc | tacatattca | gacacatgtg | 780 |
| tttggaagac | caatcttgtt | cactaggcct | cttattttcg | ccactgcgtt | tatgagcttt | 840 |
| ttctctgtcg | ttattgcatt | gtttaaggat | atacctgata | tcgaagggga | taagatattc | 900 |
| ggaatccgat | cattctctgt | aactctgggt | cagaaacggg | tgttttggac | atgtgttaca | 960 |
| ctacttcaaa | tggcttacgc | tgttgcaatt | ctagttggag | ccacatctcc | attcatatgg | 1020 |
| agcaaagtca | tctcggttgt | gggtcatgtt | atactcgcaa | caactttgtg | ggctcgagct | 1080 |
| aagtccgttg | atctgagtag | caaaaccgaa | ataacttcat | gttatatgtt | catatggaag | 1140 |
| ctcttttatg | cagagtactt | gctgttacct | tttttgaagt | ga | | 1182 |

<210> SEQ ID NO 27
<211> LENGTH: 1404
<212> TYPE: DNA
<213> ORGANISM: Arabidopsis thaliana

<400> SEQUENCE: 27

| | | | | | |
|---|---|---|---|---|---|
| atggcgacga | cggttacact | caaatccttc | accggacttc | gtcaatcatc | aacggagcaa | 60 |
| acaaacttcg | tctctcatgt | accgtcatca | ctttctctcc | ctcaacgacg | gacctctctc | 120 |
| cgagtaaccg | cagccagggc | cactcccaaa | ctctccaacc | gtaaactccg | tgtcgccgtc | 180 |
| atcggtggtg | gaccagcagg | cggggcagct | gcagagactc | tagcacaagg | aggaatcgag | 240 |
| acgattctca | tcgagcgtaa | gatggacaat | tgcaagcctt | gcggtggcgc | gattcctctc | 300 |
| tgtatggtcg | gagaattcaa | cttgccgttg | gatattattg | atcggagagt | gacgaagatg | 360 |
| aagatgattt | cgccgtcgaa | cattgctgtt | gatattggtc | gtacgcttaa | ggagcatgag | 420 |
| tatataggta | tggtgagaag | agaagttctt | gatgcttatc | tgagagagag | agctgagaag | 480 |
| agtgagcca | ctgtgattaa | cggtctcttc | cttaagatgg | atcatccgga | gaattgggac | 540 |
| tcgccgtaca | ctttgcatta | cactgagtac | gatggtaaaa | ctggagctac | agggacgaag | 600 |
| aaaacaatgg | aggttgatgc | tgtcattgga | gctgatggag | ctaactctag | ggttgctaaa | 660 |
| tctattgatg | ctggtgatta | cgactacgca | attgcatttc | aggagaggat | taggattcct | 720 |
| gatgagaaaa | tgacttacta | tgaggattta | gctgagatgt | atgttggaga | tgatgtgtcg | 780 |
| ccggatttct | atggttgggt | gttccctaag | tgcgaccatg | tagctgttgg | aacaggtact | 840 |

-continued

```
gtgactcaca aaggtgacat caagaagttc cagctcgcga ccagaaacag agctaaggac    900
aagattcttg gagggaagat catccgtgtg gaggctcatc cgattcctga acatccgaga    960
ccacgtaggc tctcgaaacg tgtggctctt gtaggtgatg ctgcagggta tgtgactaaa   1020
tgctctggtg aagggatcta ctttgctgct aagagtggaa gaatgtgtgc tgaagccatt   1080
gtcgaaggtt cacagaatgg taagaagatg attgacgaag gggacttgag gaagtacttg   1140
gagaaatggg ataagacata cttgcctacc tacagggtac ttgatgtgtt gcagaaagtg   1200
ttttacagat caaatccggc tagagaagcg tttgtggaga tgtgtaatga tgagtatgtt   1260
cagaagatga cattcgatag ctatctgtac aagcgggttg cgccgggtag tcctttggag   1320
gatatcaagt tggctgtgaa caccattgga agtttggtta gggctaatgc tctaaggaga   1380
gagattgaga agcttagtgt ttaa                                          1404

<210> SEQ ID NO 28
<211> LENGTH: 35
<212> TYPE: DNA
<213> ORGANISM: Artificial
<220> FEATURE:
<223> OTHER INFORMATION: Bt-HX-1-f PCR primer sequence

<400> SEQUENCE: 28
gcgcagccat ggcgaaacaa aaatctatgg atacg                                35

<210> SEQ ID NO 29
<211> LENGTH: 29
<212> TYPE: DNA
<213> ORGANISM: Artificial
<220> FEATURE:
<223> OTHER INFORMATION: Bt-HX-2-f PCR primer sequence

<400> SEQUENCE: 29
gcgcagccat ggaggacttt ttccagtac                                       29

<210> SEQ ID NO 30
<211> LENGTH: 33
<212> TYPE: DNA
<213> ORGANISM: Artificial
<220> FEATURE:
<223> OTHER INFORMATION: Bt-HX-3-r PCR primer sequence

<400> SEQUENCE: 30
gcgcagctcg agtcataagt ttccgcgacg ctc                                  33

<210> SEQ ID NO 31
<211> LENGTH: 37
<212> TYPE: DNA
<213> ORGANISM: Artificial
<220> FEATURE:
<223> OTHER INFORMATION: Gh-1-f:5'PCR primer sequence

<400> SEQUENCE: 31
gcgcagccat ggccaatccg aaatccgatc ggttcac                              37

<210> SEQ ID NO 32
<211> LENGTH: 35
<212> TYPE: DNA
<213> ORGANISM: Artificial
<220> FEATURE:
<223> OTHER INFORMATION: Gh-1-r:5'PCR primer sequence

<400> SEQUENCE: 32
```

-continued gcgcagctcg agtcatggat tctgggactg tttgg                                                                    35

<210> SEQ ID NO 33
<211> LENGTH: 28
<212> TYPE: DNA
<213> ORGANISM: Artificial
<220> FEATURE:
<223> OTHER INFORMATION: Bn-1-f:5'PCR primer sequence

<400> SEQUENCE: 33
ggagctccat ggggcacgaa aacgccgc                                                                            28

<210> SEQ ID NO 34
<211> LENGTH: 33
<212> TYPE: DNA
<213> ORGANISM: Artificial
<220> FEATURE:
<223> OTHER INFORMATION: Bn-2-r:5'PCR primer sequence

<400> SEQUENCE: 34
ggagctctcg agtcaaccca caagctgttt ggc                                                                      33

<210> SEQ ID NO 35
<211> LENGTH: 33
<212> TYPE: DNA
<213> ORGANISM: Artificial
<220> FEATURE:
<223> OTHER INFORMATION: Tomato (f) primer sequence

<400> SEQUENCE: 35
ggagctcata tggctaatcc ccgttccgat ttc                                                                      33

<210> SEQ ID NO 36
<211> LENGTH: 33
<212> TYPE: DNA
<213> ORGANISM: Artificial
<220> FEATURE:
<223> OTHER INFORMATION: Tomato (r) primer sequence

<400> SEQUENCE: 36
ggagctctcg agtcattcga cagcagctac ttg                                                                      33

<210> SEQ ID NO 37
<211> LENGTH: 445
<212> TYPE: PRT
<213> ORGANISM: Arabidopsis thaliana

<400> SEQUENCE: 37

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45

His Ile Glu Phe Trp Cys Gly Asp Ala Thr Asn Val Ala Arg Arg Phe
        50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
                100                 105                 110

```
Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
                180                 185                 190

Lys Ala Glu Asp Thr Glu Lys Ser Glu Phe Leu Pro Gly Phe Glu Arg
                195                 200                 205

Val Glu Asp Ala Ser Ser Phe Pro Leu Asp Tyr Gly Ile Arg Arg Leu
210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
                260                 265                 270

Asn Asp Glu Met Val Leu Leu Pro Ile Asn Glu Pro Val His Gly Thr
                275                 280                 285

Lys Arg Lys Ser Gln Ile Gln Thr Tyr Leu Glu His Asn Glu Gly Ala
    290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Pro Thr Tyr Tyr Gln Asn Leu Lys Lys Arg Val Gly Asp
                340                 345                 350

Val Leu Ser Asp Asp Gln Ile Lys Glu Cys Glu Glu Leu Gly Ile Leu
                355                 360                 365

Val Asp Arg Asp Asp Gln Gly Thr Leu Leu Gln Ile Phe Thr Lys Pro
    370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
                420                 425                 430

Glu Tyr Glu Lys Thr Leu Glu Ala Lys Gln Leu Val Gly
                435                 440                 445

<210> SEQ ID NO 38
<211> LENGTH: 15
<212> TYPE: PRT
<213> ORGANISM: Arabidopsis thaliana

<400> SEQUENCE: 38

Cys Met Met Lys Asp Glu Glu Gly Lys Ala Tyr Gln Ser Gly Gly
1               5                   10                  15

<210> SEQ ID NO 39
<211> LENGTH: 15
<212> TYPE: PRT
<213> ORGANISM: Arabidopsis thaliana
```

```
<400> SEQUENCE: 39

Cys Arg Thr Leu Arg Glu Met Arg Lys Arg Ser Ser Ile Gly Gly
1               5                   10                  15

<210> SEQ ID NO 40
<211> LENGTH: 339
<212> TYPE: PRT
<213> ORGANISM: Synechocystis PCC6803

<400> SEQUENCE: 40

Met Glu Phe Asp Tyr Leu His Leu Tyr Val Asp Asp Tyr Gln Ser Ala
1               5                   10                  15

His Arg Cys Tyr Gln Arg Gln Trp Gly Phe Thr Cys Val Asn Lys Ile
            20                  25                  30

Ile Thr Asp Gln Gly Ile Thr Gly Ile Tyr Gln Gln Gly Gln Ile Leu
        35                  40                  45

Leu Leu Ile Ser Ala Ser Glu Ser Ser Leu Ser Arg Tyr Ala Asp Tyr
    50                  55                  60

Leu Gln Lys His Pro Pro Gly Val Gly Glu Val Ala Trp Gln Val Ala
65                  70                  75                  80

Asn Trp Gln Lys Ile Gln His Gln Leu Ser Glu Leu Gln Ile Glu Thr
                85                  90                  95

Thr Pro Val Ile His Pro Leu Thr Lys Ala Glu Gly Leu Thr Phe Leu
            100                 105                 110

Leu Trp Gly Asp Val His His Ser Ile Tyr Pro Val Arg Ser Glu Leu
        115                 120                 125

Asn Gln Asn Lys Thr Leu His Gly Val Gly Leu Thr Thr Ile Asp His
    130                 135                 140

Val Val Leu Asn Ile Ala Ala Asp Gln Phe Thr Gln Ala Ser Gln Trp
145                 150                 155                 160

Tyr Gln Gln Val Phe Gly Trp Ser Val Gln Gln Ser Phe Thr Val Asn
                165                 170                 175

Thr Pro His Ser Gly Leu Tyr Ser Glu Ala Leu Ala Ser Ala Asn Gly
            180                 185                 190

Lys Val Gln Phe Asn Leu Asn Cys Pro Thr Asn Ser Ser Gln Ile
        195                 200                 205

Gln Thr Phe Leu Ala Asn Asn His Gly Ala Gly Ile Gln His Val Ala
    210                 215                 220

Phe Ser Thr Thr Ser Ile Thr Arg Thr Val Ala His Leu Arg Glu Arg
225                 230                 235                 240

Gly Val Asn Phe Leu Lys Ile Pro Thr Gly Tyr Tyr Gln Gln Gln Arg
                245                 250                 255

Asn Ser Ser Tyr Phe Asn Tyr Ala Ser Leu Asp Trp Asp Thr Leu Gln
            260                 265                 270

Cys Leu Glu Ile Leu Leu Asp Asp Gln Asp Asn Thr Gly Glu Arg Leu
        275                 280                 285

Leu Leu Gln Ile Phe Ser Gln Pro Cys Tyr Gly Val Gly Thr Leu Phe
    290                 295                 300

Trp Glu Ile Ile Glu Arg Arg His Arg Ala Lys Gly Phe Gly Gln Gly
305                 310                 315                 320

Asn Phe Gln Ala Leu Tyr Glu Ala Val Glu Thr Leu Glu Lys Gln Leu
                325                 330                 335

Glu Val Pro
```

-continued

<210> SEQ ID NO 41
<211> LENGTH: 15
<212> TYPE: PRT
<213> ORGANISM: Synechocystis PCC6803

<400> SEQUENCE: 41

```
Glu Ile Leu Leu Asp Asp Gln Asp Asn Thr Gly Glu Arg Leu Leu
1               5                   10                  15
```

<210> SEQ ID NO 42
<211> LENGTH: 20
<212> TYPE: PRT
<213> ORGANISM: Bacillus thuringiensis

<400> SEQUENCE: 42

```
Gly Ile Leu Val Asp Arg Asp Asp Glu Gly Tyr Leu Leu Gln Ile Phe
1               5                   10                  15

Thr Lys Pro Cys
            20
```

<210> SEQ ID NO 43
<211> LENGTH: 20
<212> TYPE: PRT
<213> ORGANISM: Artificial
<220> FEATURE:
<223> OTHER INFORMATION: Uni-HPPD polypeptide antigen

<400> SEQUENCE: 43

```
Gly Ile Leu Val Asp Arg Asp Asp Gln Gly Thr Leu Leu Gln Ile Phe
1               5                   10                  15

Thr Lys Pro Cys
            20
```

<210> SEQ ID NO 44
<211> LENGTH: 1128
<212> TYPE: DNA
<213> ORGANISM: Artificial
<220> FEATURE:
<223> OTHER INFORMATION: Modified Bt.Met14.HPPD

<400> SEQUENCE: 44

```
atggcgaaac aaaaatctat ggatacgcta gctgcacaaa tggaggactt ttttccagta     60
cgtgatgtag atcatttgga attttacgta gggaatgcaa agcaatcgag ttattatctt    120
gcgagagcgt tcggattcaa aattgtagct tactctggat tagaaactgg aaaccgtgaa    180
aaggtatctt atgttcttgt gcaaaaaaat atgcgtttcg ttgtgtctgg agctttaagt    240
agtgaaaatc gtattgcaga gtttgtaaag actcatggtg atggcgtgaa ggatgtggca    300
ctacttgttg atgatgttga taaagcatac tcagaagcag tgaaacgtgg tgccgtcgca    360
attgctccac cgcaggaatt aacagatgag gacggtacat tgaaaaaagc agttattggt    420
acgtatggtg atacaattca tacgcttgta gagcgtaaaa attataaagg ggcatttatg    480
ccaggattcc aaaaggtaga atttaatatt ccatttgagg agtctggttt aattgctgtt    540
gatcatgtag ttggtaatgt tgaaaaaatg gaagagtggg ttagttatta cgagaatgtt    600
atgggcttta aacaaatgat tcattttgat gatgacgata ttagtacaga gtattcggcg    660
ttaatgtcaa aagttatgac gaatggaagt cgtattaagt ttcctattaa cgaaccagca    720
gacggaaaga gaaagtcaca aattcaagag tatctagaat tctataatgg agctggtgta    780
caacatcttg ctttattaac aagtgatatt gttaaaacag ttgaagcgct tcgtgcaaat    840
```

```
gggtggagt ttttagatac acctgatact tattacgatg agctaactgc acgagttgga        900
aaaatcgatg aagaaattga taagttaaaa gaattaaaga tcttagtaga tcgtgatgat        960
gaaggttact tactacaaat ctttacgaaa ccaattgtag atcgtccgac tttatttatt       1020
gaaatcattc aacgtaaagg ttctcgtgga tttggtgaag gaaactttaa agcgttattc       1080
gaatcaattg aaagagaaca agagcgtcgc ggaaacttat gactcgag                    1128
```